United States Patent
Sun et al.

(10) Patent No.: US 10,077,436 B2
(45) Date of Patent: Sep. 18, 2018

(54) BETA-GLUCOSIDASE ENZYMES FOR INCREASED BIOMASS SACCHARIFICATION

(71) Applicant: Edeniq, Inc., Visalia, CA (US)

(72) Inventors: Lan Sun, Visalia, CA (US); Ngim Muy Ung Ferrell, Clovis, CA (US); Deepak Singh, Fresno, CA (US); Jennifer Headman, Oceanside, CA (US); Mei-Hua Chu, San Diego, CA (US); Michael Guerini, Gilroy, CA (US); Sandra Jacobson, Three Rivers, CA (US)

(73) Assignee: EDENIQ, INC., Visalia, CA (US)

( * ) Notice: Subject to any disclaimer, the term of this patent is extended or adjusted under 35 U.S.C. 154(b) by 142 days.

(21) Appl. No.: 15/022,903

(22) PCT Filed: Sep. 16, 2014

(86) PCT No.: PCT/US2014/055927
§ 371 (c)(1),
(2) Date: Mar. 17, 2016

(87) PCT Pub. No.: WO2015/042064
PCT Pub. Date: Mar. 26, 2015

(65) Prior Publication Data
US 2016/0304849 A1    Oct. 20, 2016

Related U.S. Application Data

(60) Provisional application No. 61/878,989, filed on Sep. 17, 2013.

(51) Int. Cl.
| | |
|---|---|
| *C12N 9/42* | (2006.01) |
| *C12P 19/02* | (2006.01) |
| *C12P 19/14* | (2006.01) |
| *C12P 7/10* | (2006.01) |
| *C12N 15/81* | (2006.01) |

(52) U.S. Cl.
CPC ........... *C12N 9/2445* (2013.01); *C12N 15/81* (2013.01); *C12P 7/10* (2013.01); *C12P 19/02* (2013.01); *C12P 19/14* (2013.01); *C12Y 302/01021* (2013.01); *Y02E 50/16* (2013.01)

(58) Field of Classification Search
CPC .. C12P 19/02; C12P 19/14; C12P 7/10; C12Y 302/01021; C12N 9/2445; C12N 15/81; Y02E 50/16
See application file for complete search history.

(56) References Cited

U.S. PATENT DOCUMENTS 8,486,683 B2    7/2013   Scott et al.

FOREIGN PATENT DOCUMENTS

WO    2011-063308 A2    5/2011

OTHER PUBLICATIONS

Nierman, W.C., GenBank accession No. XP_001269582, Feb. 21, 2008.*
Branden et al., Introduction to Protein Structure, Garland Publishing Inc., New York, p. 247.*
Sadowski et al., Current Opinion in Structural Biology 19:357-362, 2009.*
Seffernick et al., J. Bacteriol. 183(8):2405-2410, 2001.*
Witkowski et al., Biochemistry 38:11643-11650, 1999.*
Kawaguchi et al., PIR accession No. JC4939, Nov. 1, 1996.*
Iwashita et al., Appl. Environ. Microbiol. 65:5546-5553, 1999.*
Thongpoo, Preeyanuch et al., "Identification of the acid/base catalyst of a glycoside hydrolase family 3 (GH3) β-glucosidase from Aspergillus niger ASKU28", Biochimica et Biophysica Acta (BBA)—General Subjects. Epub. Nov. 29, 2012, vol. 1830, No. 3, pp. 2739-2749.
Murray, Patrick et al., "Expression in Trichoderma reesei and characterization of a thermostable family 3 β-glucosidase from the moderately thermophilic fungus Talaromyces emersonii", Protein Expression and Purification, 2004, vol. 38, No. 2, pp. 248-257.
NCBI, GenBank accession No. CAB75696.1 (Nov. 14, 2006).
Thongpoo, Preeyanuch et al., "Purification and characterization of three β-glycosidases exhibiting high glucose tolerance from Aspergillus niger ASKU28", Bioscience, Biotechnology, and Biochemistry, Epub. May 28, 2014, vol. 78, No. 7, pp. 1167-1176.
International application PCT/US2014/055927, International Search Report and Written Opinion dated Dec. 29, 2014.

* cited by examiner

*Primary Examiner* — Delia Ramirez
(74) *Attorney, Agent, or Firm* — Kilpatrick Townsend & Stockton LLP

(57) ABSTRACT

Described herein are beta-glucosidase enzymes that have improved beta-glucosidase activity compared to a control beta-glucosidase enzyme. The improved beta-glucosidase enzymes are useful for converting a cellulosic biomass to fermentable sugars such as glucose. Also described are isolated polynucleotides that encode polypeptides having improved beta-glucosidase activity, expression cassettes for expressing the improved beta-glucosidase polypeptides, and cells, such as yeast cells, transformed with the expression cassettes.

15 Claims, 22 Drawing Sheets
Specification includes a Sequence Listing.

BETA-GLUCOSIDASE ENZYMES FOR INCREASED BIOMASS SACCHARIFICATION

CROSS REFERENCE TO RELATED APPLICATION

This application is the U.S. national stage of PCT/US2014/055927, filed Sep. 16, 2014, which claims the benefit of priority to U.S. Provisional Application No. 61/878,989, filed Sep. 17, 2013, both of which are incorporated by reference herein in their entirety for all purposes.

BACKGROUND OF THE INVENTION

Lignocellulosic materials contain carbohydrate in the form of complex polymers. The polymers can be broken down to simple sugars which in turn can be used to produce various products including ethanol. Various biomass feedstocks have a lignocellulosic structure where lignin surrounds the hemicelluloses and cellulosic carbohydrates whose release increases upon enzymatic treatment with cellulases. However, enzyme cost and low efficiency of hydrolysis are major issues associated with lignocellulosic materials' potential as a source of fermentable sugars.

Beta-glucosidase (BG) is a key cellulosic enzyme that hydrolyzes the di-saccharide cellobiose into the mono-saccharide glucose. This last step in glucan saccharification generates the preferred sugar (glucose) for fermentation, and effectively clears the enzymatic pathway of its end product. If glucose concentration is high, end-product inhibition of upstream cellulases occurs. End-product inhibition decreases flux through the saccharification pathway by decreasing the catalytic activity of upstream enzymes including cellobiohydroblases (CBH1, CBH2) and endoglucanase (EG). Thus, overall saccharification efficiency can be diminished in glucose titer and kinetics of sugar production.

Available BG enzymes can have reduced activity in the presence of glucose levels typically found in biomass saccharification reactions, i.e. product inhibition. Reduced activity generally can be quantified as the amount of substrate hydrolysis that occurs in a specified time under specified reaction conditions in the presence of glucose vs. in the absence of glucose. Product inhibition could result in altered kinetic properties of enzymes, such as Michaelis-Menten constant (Km) and maximum velocity (Vmax), depending on different inhibition mechanisms. Competitive inhibition increases the apparent Km without affecting the value of Vmax. Noncompetitive inhibition decreases the apparent Vmax without affecting the Km. Uncompetitive inhibition decreases the apparent values of both Km and Vmax. Mixed inhibition also exists and has more complex effects on kinetic properties. These BG enzymes may also have sub-optimal half-lives and thermo-tolerance, making it useful to have an improved form of BG to get the highest glucose yields during saccharification. The present disclosure provides, among other things, improved beta-glucosidase enzymes that increase the conversion of cellobiose to glucose, and thus improve saccharification efficiency.

BRIEF SUMMARY OF THE INVENTION

This application provides improved beta-glucosidase enzymes, and methods of using the improved beta-glucosidase enzymes for converting cellulosic biomass into sugars. This application also provides polynucleotides comprising nucleic acids that encode the improved beta-glucosidase enzymes described herein, and polypeptides comprising the amino acid sequences of the improved beta-glucosidases.

Thus, in one aspect, provided herein are improved beta-glucosidases comprising a polypeptide having increased beta-glucosidase activity compared to a reference or unmodified beta-glucosidase. In some embodiments, the improved beta-glucosidases comprise polypeptides having at least 70% sequence identity to the amino acid sequence of SEQ ID NOS:2, 4, 6, 8, 10, 12 or 14, and improved beta-glucosidase activity compared to a control beta-glucosidase comprising the amino acid sequence of SEQ ID NO:2.

In some embodiments, the improved beta-glucosidase comprises an amino acid at one or more positions corresponding to a position selected from the group consisting of:
 (a) position 66 of SEQ ID NO:2, wherein the amino acid corresponding to position 66 is an amino acid other than T;
 (b) position 70 of SEQ ID NO:2, wherein the amino acid corresponding to position 70 is an amino acid other than L;
 (c) position 136 of SEQ ID NO:2, wherein the amino acid corresponding to position 136 is an amino acid other than G;
 (d) position 139 of SEQ ID NO:2, wherein the amino acid corresponding to position 139 is an amino acid other than I;
 (e) position 167 of SEQ ID NO:2, wherein the amino acid corresponding to position 167 is an amino acid other than L;
 (f) position 250 of SEQ ID NO:2, wherein the amino acid corresponding to position 250 is an amino acid other than Q (wild type amino acid is Q);
 (g) position 286 of SEQ ID NO:2, wherein the amino acid corresponding to position 286 is an amino acid other than A;
 (h) position 363 of SEQ ID NO:2, wherein the amino acid corresponding to position 363 is an amino acid other than Y;
 (i) position 375 of SEQ ID NO:2, wherein the amino acid corresponding to position 375 is an amino acid other than Y;
 (j) position 376 of SEQ ID NO:2, wherein the amino acid corresponding to position 376 is an amino acid other than E;
 (k) position 610 of SEQ ID NO:2, wherein the amino acid corresponding to position 610 is an amino acid other than Y or P; and/or
 (l) position 791 of SEQ ID NO:2, wherein the amino acid corresponding to position 791 is an amino acid other than N.

In some embodiments, the improved beta-glucosidase comprises an amino acid at one or more positions corresponding to a position selected from the group consisting of:
 (a) position 66 of SEQ ID NO:2, wherein the amino acid corresponding to position 66 is I;
 (b) position 70 of SEQ ID NO:2, wherein the amino acid corresponding to position 70 is S;
 (c) position 136 of SEQ ID NO:2, wherein the amino acid corresponding to position 136 is C;
 (d) position 139 of SEQ ID NO:2, wherein the amino acid corresponding to position 139 is F;
 (e) position 167 of SEQ ID NO:2, wherein the amino acid corresponding to position 167 is M;
 (f) position 250 of SEQ ID NO:2, wherein the amino acid corresponding to position 250 is L;

(g) position 286 of SEQ ID NO:2, wherein the amino acid corresponding to position 286 is D;
(h) position 363 of SEQ ID NO:2, wherein the amino acid corresponding to position 363 is C;
(i) position 375 of SEQ ID NO:2, wherein the amino acid corresponding to position 375 is F;
(j) position 376 of SEQ ID NO:2, wherein the amino acid corresponding to position 376 is K;
(k) position 610 of SEQ ID NO:2, wherein the amino acid corresponding to position 610 is F; and/or
(l) position 791 of SEQ ID NO:2, wherein the amino acid corresponding to position 791 is I.

In another aspect, provided herein are polynucleotides comprising a nucleic acid encoding the improved beta-glucosidases described herein. In some embodiments, the polynucleotide comprises an expression cassette, where the expression cassette comprises a heterologous promoter operably linked to the nucleic acid. In some embodiments, a vector is provided that comprises a polynucleotide encoding the improved beta-glucosidases described herein.

In another aspect, provided herein are isolated cells or cultures of cells, wherein the cell(s) comprise a polynucleotide comprising a nucleic acid encoding the improved beta-glucosidases described herein. In some embodiments, the polynucleotide is heterologous to the cell. In some embodiments, the cell is a yeast cell. In certain embodiments, the cell is a *Saccharomyces cerevisiae* or a *Pichia stipitis*. In one embodiment, the improved beta-glucosidase is secreted from the cell.

In another aspect, provided herein are methods for converting a cellulose-containing material, such as a cellulose-containing biomass feedstock, to a sugar, the method comprising treating the cellulose-containing material with an improved beta-glucosidase, or with a cell that expresses the improved beta-glucosidase described herein. In some embodiments, the cellulose-containing material comprises cellobiose. In some embodiments, the improved beta-glucosidase increases the conversion of cellobiose to glucose in the presence of higher concentrations of glucose as compared to a control or unmodified beta-glucosidase. In some embodiments, the improved beta-glucosidase increases the conversion rate of cellobiose to glucose in the presence of higher concentrations of glucose as compared to a control or unmodified beta-glucosidase. In some embodiments, the improved beta-glucosidase increases the conversion of cellobiose to glucose in the presence of 10-15% w/v glucose. In some embodiments, the control beta-glucosidase comprises the amino acid sequence of SEQ ID NO:2.

In some embodiments, the improved beta-glucosidase has improved kinetic properties compared to a control or unmodified beta-glucosidase. Thus, in some embodiments, improved kinetic properties include increased catalytic efficiency (e.g., sometimes expressed as Kcat/Km or Kcat/Km/min), increased maximum velocity (e.g., sometimes denoted as Vmax), and/or increased turnover number (e.g., sometimes denoted as Kcat or Kcat/min).

In some embodiments, the methods described herein comprise fermenting the sugar to ethanol. In some embodiments, the cell that expresses the improved beta-glucosidase described herein is a yeast cell.

In some embodiments, the cellulose-containing biomass feedstock is a woody material. Thus, in some embodiments, the woody material is cellulosic or lignocellulosic plant material selected from, but not limited to, the group consisting of orchard prunings, chaparral, mill waste, urban wood waste, municipal waste, logging waste, forest thinnings, short-rotation woody crops, and industrial waste.

In some embodiments, the cellulose-containing biomass feedstock is a non-woody material. Thus, in some embodiments, the non-woody material is selected from, but not limited to, the group consisting of gramineous agricultural residue, wheat straw, oat straw, rice straw, barley straw, rye straw, flax straw, sugar cane, corn stover, corn stalks, corn cobs, corn husks, prairie grass, switchgrass, gamagrass, foxtail, sugar beet pulp, citrus fruit pulp, seed hulls, cellulosic animal wastes, lawn clippings, seaweed, bagasse, energy cane, and giant reed. In some embodiments, the cellulose-containing biomass feedstock is corn grain, barley grain, milo grain, wheat grain or rice grain.

In some embodiments, the methods are useful for converting a cellulose-containing material to sugars. In some embodiments, the cellulose-containing material is a paper product, such as but not limited to cardboard, newspaper or filter paper.

DEFINITIONS

Figure 1:
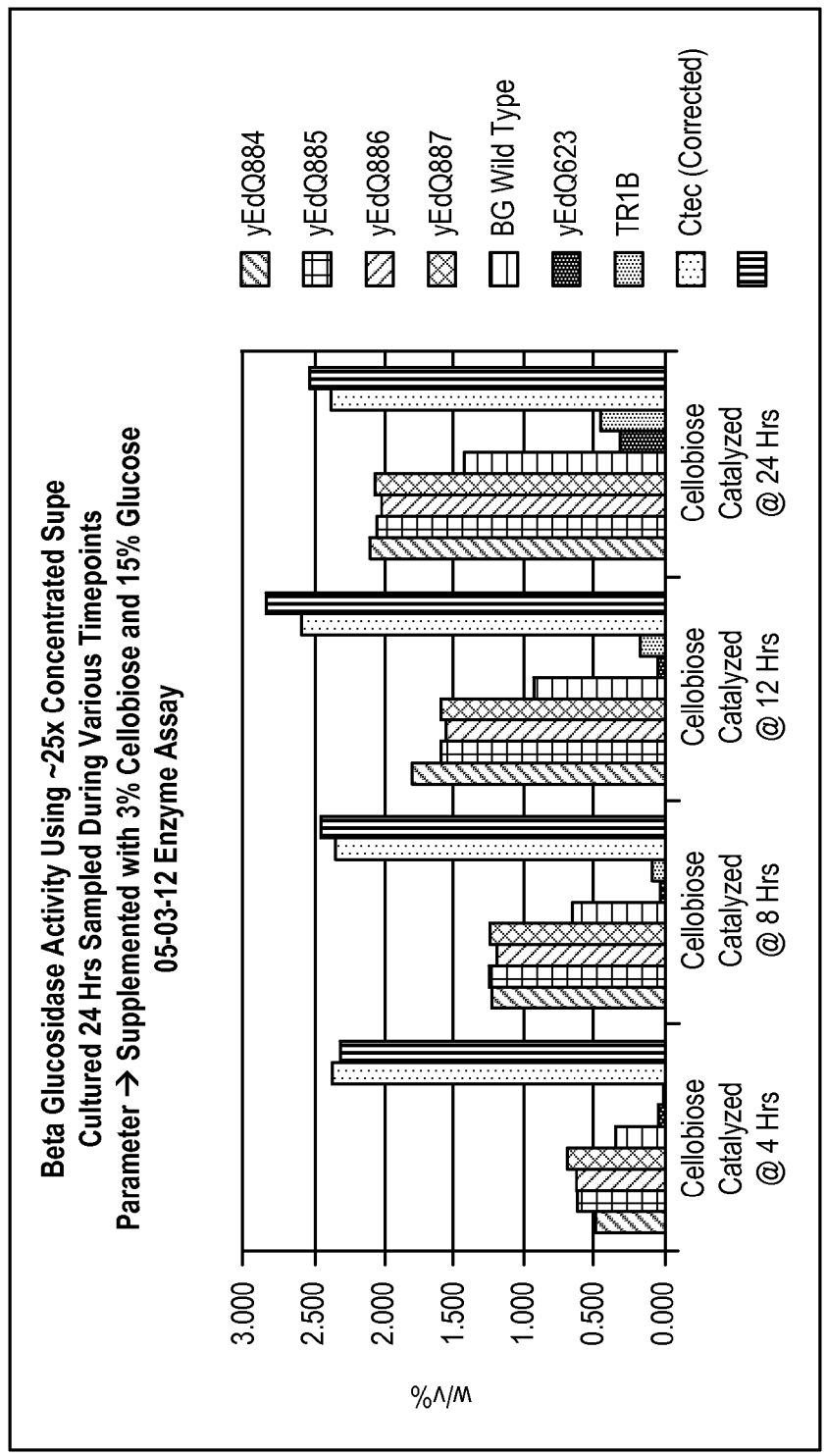
FIG. 1 shows beta glucosidase activity on cellobiose substrate in terms of catalyzed substrate in the presence of high glucose.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same. The term "substantially identical" refers to two or more sequences or subsequences that have a specified percentage of amino acid residues or nucleotides that are the same (i.e., at least about 40% identity, 45%, 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see e.g., NCBI web site or the like). The present invention provides for, e.g., polypeptide sequences (e.g., improved beta-glucosidase enzymes) that are substantially identical to a reference sequence, e.g., SEQ ID NOS: 4, 6, 8, 10, 12, and 14, as well as nucleic acids encoding such polypeptides. The definition includes sequences that have deletions and/or additions, as well as those that have substitutions. As described below, algorithms can account for gaps and the like. When not specified, identity or substantial identity is determined over the entire length of the reference sequence. When specified, identity can be determined over a region that is at least about 10 amino acids or nucleotides in length, at least about 25 amino acids or nucleotides in length, or over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An exemplary algorithm suitable for determining percent sequence identity and sequence similarity is BLAST 2.0 algorithm, which is described in Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci.* USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci.* USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

To determine which amino acid of a first protein "corresponds" to the position of an amino acid in a second protein, the amino acid sequences of the two proteins are optimally aligned (e.g., using a BLAST algorithm). This is particularly useful, for example, where two proteins have high homology but where one protein contains one or more insertions or deletions relative to the second protein. In such cases, for example, position 57 of a first protein may align with position 51 in a second protein when the two proteins are optimally aligned. Thus position 51 of the second protein "corresponds" to position 57 of the first protein.

A "heterologous sequence," "heterologous polypeptide," or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA or by being linked to a heterologous promoter or by being linked to a reporter gene, etc.

"Expression cassette" refers to a polynucleotide comprising a promoter or other regulatory sequence operably linked to a sequence encoding a protein.

The term "improved beta-glucosidase activity," or "improved BG activity," as used herein, means a variant beta-glucosidase displaying an increase, relative to a reference sequence (e.g., a control sequence or an unmodified form of beta-glucosidase as described herein), in the amount of substrate hydrolysis that occurs in a specified time under specified reaction conditions. In some embodiments, the variant beta-glucosidase can display an increase of, relative to a reference sequence, at least 5%, 10%, 20%, 30%, 40%, 50%, 100%, 200%, or more, in the amount of substrate hydrolysis that occurs in a specified time under specified reaction conditions. In some embodiments, the reference sequence has a sequence that is the same as the variant beta-glucosidase sequence except for positions with modifications. Beta-glucosidase activity can be measured using a variety of methods known in the art, such as a cellobiose gradient assay, a sodium dichlorindo-phenolate hydrate (DCPIP) plate or liquid assay, a cellobiose challenge assay, a cellobiose conversion assay, or a p-nitrophenyl β-D-glucopyranoside (pNPG) assay, as described herein below and in Ghose (1980) *Pure and Applied Chemistry* 59:257-268, and Zhang et al., (2009) In *Biofuels: Methods and Protocols, Methods in Molecular Biology* 581:213-231. To compare the beta-glucosidase activity of two recombinantly expressed proteins, the specific activity (activity per mole enzyme or activity per gram enzyme) can be compared. Alternatively, cells expressing and secreting the recombinant proteins can be cultured under the same conditions and the beta-glucosidase activity per volume culture medium can be compared.

The term "hydrolysis" refers to breaking the glycosidic bonds in polysaccharides to yield simple monomeric and/or oligomeric sugars. For example, hydrolysis of cellulose produces the six carbon (C6) sugar glucose, whereas hydrolysis of hemicellulose produces the five carbon (C5) sugars including xylose and arabinose. Generating short chain cellulosic sugars from polymer cellulosic fibers and biomass can be achieved by a variety of techniques, processes, and or methods. For example, cellulose can be hydrolyzed with water to generate cellulosic sugars. Hydrolysis can be assisted and or accelerated with the use of hydrolytic enzymes, chemicals, mechanical shear, thermal and pressure environments, and or any combination of these techniques. Examples of hydrolytic enzymes include cellulases and hemicellulases and amylases. Cellulase is a generic term for a multi-enzyme mixture including exo-cellobiohydrolases, endoglucanases and β-glucosidases which work in combination to hydrolyze cellulose to cellobiose and glucose. Hydrolytic enzymes are also referred to as "saccharification enzymes." Examples of chemicals include strong acids, weak acids, weak bases, strong bases, ammonia, or other chemicals. Mechanical shear includes high shear orifice, cavitation, colloidal milling, and auger milling. Examples of high shear devices include an ICStype orifice reactor (Buchen-Industrial Catalyst Service), a rotating colloidal-type mill, a Silverson mixer, cavitation milling device, or steam assisted hydro-jet type mill.

The term "cellulose-containing biomass feedstock" is defined herein to mean any cellulosic or lignocellulosic plant material, waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being woodlike". Accordingly, "nonwoody" refers to materials lacking these characteristics. Cellulose-containing biomass feedstock includes, but is not limited to, crops such as starch crops (e.g., corn, wheat, rice or barley), sugar crops (e.g., sugarcane, energy cane or sugarbeet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes or wood), and process waste; and aquatic plants such as algae, water weed, water hyacinth, or reed and rushes.

In some embodiments, cellulose-containing biomass feedstock from woody plants can include orchard prunings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants in agriculture is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g. big bluestem, little bluestem, Indian grass), switchgrass, gamagrass, and foxtail. In some embodiments, the agricultural biomass comprises corn kernel, barley kernel, milo kernel, wheat kernel or rice kernel.

Byproducts of agriculture industrial process can have high amounts of furfural and 5-HMF. For example, corncobs are used to produce xylose and furfural in certain countries, including China. For economic reasons, corncobs are treated by acid hydrolysis with byproduct residues from such production considered waste product inasmuch as inhibitors such as furfural are present. Such waste processing residues are usually burned. However, a significant amount of cellulose exists in the corncob residues that can be used to convert into ethanol.

Other agricultural byproducts in the category of biomass include waste streams components from commercial processing of crop materials (such as sugar beet pulp, citrus fruit pulp, sugarcane bagasse, seed hulls, and the like), cellulosic animal wastes, lawn clippings, seaweed, etc. In some embodiments, the biomass is distillers grains.

Any of the aforementioned biomass materials would be utilized as substrates for fermentative conversion to ethanol.

For purposes of this application, any range of numerical values includes the end point values and all values in between thereof, including integer and non-integer values. For example, the range of 10-15 includes 10, 11, 12, 13, 14, and 15, and also includes non-integer values such as 10.5, 11.5, etc.

As used herein, the term "about," when modifying any amount, refers to the variation in that amount typically encountered by one of skill in the art, i.e., in an ethanol production facility or testing lab. For example, the term "about" refers to the normal variation encountered in measurements for a given analytical technique, both within and between batches or samples. Thus, the term about can include variation of 1-10% of the measure value, such as 5% or 10% variation. The amounts disclosed herein include equivalents to those amounts, including amounts modified or not modified by the term "about."

DETAILED DESCRIPTION OF THE INVENTION

I. Introduction

The present disclosure provides improved beta-glucosidase enzymes having improved beta-glucosidase activity. Beta-glucosidase (BG) is a cellulosic enzyme that hydrolyzes the di-saccharide cellobiose into the mono-saccharide glucose. This last step in glucan saccharification generates the preferred sugar (glucose) for fermentation, and effectively clears the enzymatic pathway of its end product. If the glucose concentration is high, end-product inhibition of upstream cellulases occurs. This decreases flux through the saccharification pathway by decreasing the catalytic activity of upstream enzymes including cellobiohydroblases (e.g., CBH1, CBH2) and endoglucanase (e.g., EG). Thus, overall saccharification efficiency can be diminished in glucose titer and kinetics of sugar production.

BG is usually harvested from fungal species that naturally produce and secrete a combination of cellulosic enzymes (See Sorenson et al., Canadian J. Microbiol. 57 p. 638-650, 2011). The survey of BG activity from 86 filamentous fungi reported by Sorenson et al. (2011) demonstrates the differences in BG activity by genus and species. *Aspergillus* isolates showed the highest BG activity (in particular *A. niger*), followed by *Trichoderma* and *Fusarium*. The two fungal species *Trichoderma reesei* and *Aspergillus niger* are predominantly used by enzyme manufacturers to produce enzymes effective on lignocellulosic material.

Commercially available BG enzymes, even those that have been produced by protein engineering and are available in commercial cellulosic enzyme cocktails, have lower activity in the higher glucose levels typical of biomass saccharification reactions and corn mash fermentations. These BG enzymes may also have sub-optimal half-lives and thermo-tolerance, making it important to have an improved form of BG to get the highest glucose yields during saccharification. Further, the BG enzyme may also be lost in the liquid stream during continuous saccharification processes, and would need to be replenished in a biomass solids recycling strategy.

The proposed catalytic mechanism of beta-glucosidase is a two-step, double-displacement involving two carboxylic acid residues. In the first step, one of the carboxylic acids (the nucleophile) attacks at the substrate anomeric center, whereas the other (the acid/base catalyst) protonates the glycosidic oxygen, thereby assisting the departure of the non-carbohydrate intermediate. This results in the formation of a covalent B-glycosyl enzyme intermediate. In a second step this intermediate is then hydrolyzed by general base-catalyzed attack of water at the anomeric center of the glycosyl enzyme to release the B-glucose product (Siegal D., et al 2000). This enzymatic process has affinity towards cellobiose and glucose; glucose binding will inhibit cellobiose binding. Enzyme substrate hydrolysis takes place via an acid/base downstream from the nucleophile site. The nucleophile site is highly conserved in BG from differing organisms and generally carries the VMSDW (SEQ ID NO: 15) amino acid sequence, by which aspartic acid (D) amino acid provides the nucleophile. The predicted three-dimensional structure of *A. niger* ASKU28 beta-glucosidase is described in Thongpoo et al (2013).

II. Improved Beta-Glucosidase Enzymes

The present disclosure provides improved beta-glucosidase enzymes having improved beta-glucosidase activity. The improved beta-glucosidases described herein have increased beta-glucosidase activity relative to a control or reference beta-glucosidase. The improved beta-glucosidases can be used in any reaction where degradation of cellulose is desired. For example, the improved beta-glucosidases described herein can be used as enzyme additives in biomass fermentation to convert biomass to ethanol. Further, these improved beta-glucosidases can be expressed in and secreted by yeast cells or other cells. This allows for lignocellulosic material-to-ethanol production in one reaction.

In some embodiments, the improved beta-glucosidases described herein increase the amount and/or rate of cellobiose converted to glucose relative to a control or reference beta-glucosidase. An increase in the amount of cellobiose converted to glucose can be determined, for example, by measuring the amount of cellobiose hydrolyzed to glucose by the improved beta-glucosidase as compared to the amount of cellobiose hydrolyzed to glucose by a reference beta-glucosidase under specified conditions. In some embodiments, the conditions are those specified in the examples.

In some embodiments, the improved beta-glucosidases described herein have improved kinetic properties. For example, in some embodiments, the improved kinetic properties include, but are not limited to, increased catalytic efficiency, increased maximum velocity, and/or increased turnover number. As a result of these improved kinetic properties, when supplementing cellulases with the improved beta-glucosidases described herein, saccharification of cellulose can be significantly enhanced.

The improved or unmodified beta-glucosidases and beta-glucosidase control preparations provided herein can be of any origin, e.g., they can be prokaryotic or eukaryotic beta-glucosidases. In some embodiments, the beta-glucosidases are fungal beta-glucosidases. In some embodiments, the beta-glucosidases are beta-glucosidase variants having at least 40%, 45%, 50%, 55%, 60%, 65%, 70%, 75%, 80%, 85%, 90%, 91%, 92%, 93%, 94%, 95%, 96%, 97%, 98%, 99%, or higher sequence identity to a fungal beta-glucosidase, e.g., a beta-glucosidase of SEQ ID NOS:2, 4, 6, 8, 10, 12, or 14, and contain one or more of the mutations described herein.

Accordingly, in some embodiments, the unmodified form of the beta-glucosidase is a wild-type or a naturally occurring beta-glucosidase, such as, for example, a fungal beta-glucosidase. The full nucleic acid and amino acid sequence for numerous fungal beta-glucosidases are available. The amino acid sequence of *A. niger* beta-glucosidase is provided as SEQ ID NO:2. Thus, in some embodiments, the unmodified beta-glucosidase is from an *Aspergillus* species. In some embodiments, the unmodified beta-glucosidase is from a *Trichoderma* species.

Also amenable to the mutations described herein are functional beta-glucosidases that have been previously modified (e.g., by amino acid substitution, addition, or deletion). Thus, suitable unmodified beta-glucosidases also include functional variants of wild-type or naturally occurring beta-glucosidases. Such variants typically will have substantial sequence identity or similarity to the wild-type or naturally occurring beta-glucosidases, typically at least 70%, 75%, 80%, 85%, 90%, 91%, 92%, 93%, 94%, 95%, 96%, 97%, 98% or 99% sequence identity. In some embodiments, such variants have at least 70%, 75%, 80%, 85%, 90%, 91%, 92%, 93%, 94%, 95%, 96%, 97%, 98% or 99% sequence identity to SEQ ID NOS: 2, 4, 6, 8, 10, 12, or 14.

The improved beta-glucosidases provided herein comprise one or more amino acid substitutions relative to the unmodified beta-glucosidases. In some embodiments, the amino acid substitution(s) comprise at least an amino acid substitution corresponding to position 66 of SEQ ID NO:2. In some embodiments, the amino acid substitution corresponding to position 66 of SEQ ID NO:2 is any amino acid other than T. In some embodiments, the amino acid substitution at the amino acid corresponding to position 66 of SEQ ID NO:2 is A, R, N, C, I, L, K, M, F, P, S, W, Y, V, D, H, G, Q or E. In some embodiments, the amino acid substitution at the amino acid corresponding to position 66 of SEQ ID NO:2 is I.

In some embodiments, the amino acid substitution(s) comprise at least an amino acid substitution corresponding to position 70 of SEQ ID NO:2. In some embodiments, the amino acid substitution corresponding to position 70 of SEQ ID NO:2 is any amino acid other than L. In some embodiments, the amino acid substitution at the amino acid corresponding to position 70 of SEQ ID NO:2 is A, R, N, C, I, K, M, F, P, S, W, Y, V, D, H, G, Q, T, or E. In some embodiments, the amino acid substitution at the amino acid corresponding to position 70 of SEQ ID NO:2 is S.

In some embodiments, the amino acid substitution(s) comprise at least an amino acid substitution corresponding to position 136 of SEQ ID NO:2. In some embodiments, the amino acid substitution corresponding to position 136 of SEQ ID NO:2 is any amino acid other than G. In some embodiments, the amino acid substitution at the amino acid corresponding to position 136 of SEQ ID NO:2 is A, R, N, C, I, L, K, M, F, P, S, W, Y, V, D, H, Q, T, or E. In some embodiments, the amino acid substitution at the amino acid corresponding to position 136 of SEQ ID NO:2 is C.

In some embodiments, the amino acid substitution(s) comprise at least an amino acid substitution corresponding to position 139 of SEQ ID NO:2. In some embodiments, the amino acid substitution corresponding to position 139 of SEQ ID NO:2 is any amino acid other than I. In some embodiments, the amino acid substitution at the amino acid corresponding to position 139 of SEQ ID NO:2 is A, R, N, C, L, K, M, F, P, S, W, Y, V, D, H, G, Q, T, or E. In some embodiments, the amino acid substitution corresponding to position 139 of SEQ ID NO:2 is any amino acid other than V. Thus, in some embodiments, the amino acid substitution at the amino acid corresponding to position 139 of SEQ ID NO:2 is A, R, N, C, I, L, K, M, F, P, S, W, Y, D, H, G, Q, T, or E. In some embodiments, the amino acid substitution at the amino acid corresponding to position 139 of SEQ ID NO:2 is F.

In some embodiments, the amino acid substitution(s) comprise at least an amino acid substitution corresponding to position 167 of SEQ ID NO:2. In some embodiments, the amino acid substitution corresponding to position 167 of SEQ ID NO:2 is any amino acid other than L. In some embodiments, the amino acid substitution at the amino acid corresponding to position 167 of SEQ ID NO:2 is A, R, N, C, I, K, M, F, P, S, W, Y, V, D, H, G, Q, T, or E. In some embodiments, the amino acid substitution at the amino acid corresponding to position 167 of SEQ ID NO:2 is M.

In some embodiments, the amino acid substitution(s) comprise at least an amino acid substitution corresponding to position 250 of SEQ ID NO:2. In some embodiments, the amino acid substitution corresponding to position 250 of SEQ ID NO:2 is any amino acid other than Q. In some embodiments, the amino acid substitution at the amino acid corresponding to position 250 of SEQ ID NO:2 is A, R, N, C, I, L, K, M, F, P, S, W, Y, V, D, H, G, T, or E. In some embodiments, the amino acid substitution at the amino acid corresponding to position 250 of SEQ ID NO:2 is L.

In some embodiments, the amino acid substitution(s) comprise at least an amino acid substitution corresponding to position 286 of SEQ ID NO:2. In some embodiments, the amino acid substitution corresponding to position 286 of SEQ ID NO:2 is any amino acid other than A. In some embodiments, the amino acid substitution at the amino acid corresponding to position 286 of SEQ ID NO:2 is R, N, C, I, L, K, M, F, P, S, W, Y, V, D, H, G, Q, T, or E. In some embodiments, the amino acid substitution corresponding to position 286 of SEQ ID NO:2 is any amino acid other than S. In some embodiments, the amino acid substitution at the amino acid corresponding to position 286 of SEQ ID NO:2 is A, R, N, C, I, L, K, M, F, P, W, Y, V, D, H, G, Q, T, or E. In some embodiments, the amino acid substitution at the amino acid corresponding to position 286 of SEQ ID NO:2 is D.

In some embodiments, the amino acid substitution(s) comprise at least an amino acid substitution corresponding to position 363 of SEQ ID NO:2. In some embodiments, the amino acid substitution corresponding to position 363 of SEQ ID NO:2 is any amino acid other than Y. In some embodiments, the amino acid substitution at the amino acid corresponding to position 363 of SEQ ID NO:2 is A, R, N, C, I, L, K, M, F, P, S, W, V, D, H, G, Q, T, or E. In some embodiments, the amino acid substitution at the amino acid corresponding to position 363 of SEQ ID NO:2 is C.

In some embodiments, the amino acid substitution(s) comprise at least an amino acid substitution corresponding to position 375 of SEQ ID NO:2. In some embodiments, the amino acid substitution corresponding to position 375 of SEQ ID NO:2 is any amino acid other than Y. In some embodiments, the amino acid substitution at the amino acid corresponding to position 375 of SEQ ID NO:2 is A, R, N, C, I, L, K, M, F, P, S, W, V, D, H, G, Q, T, or E. In some embodiments, the amino acid substitution at the amino acid corresponding to position 375 of SEQ ID NO:2 is F.

In some embodiments, the amino acid substitution(s) comprise at least an amino acid substitution corresponding to position 376 of SEQ ID NO:2. In some embodiments, the amino acid substitution corresponding to position 376 of SEQ ID NO:2 is any amino acid other than E. In some embodiments, the amino acid substitution at the amino acid corresponding to position 376 of SEQ ID NO:2 is A, R, N, C, I, L, K, M, F, P, S, W, Y, V, D, H, G, Q, or T. In some embodiments, the amino acid substitution at the amino acid corresponding to position 376 of SEQ ID NO:2 is K.

In some embodiments, the amino acid substitution(s) comprise at least an amino acid substitution corresponding to position 610 of SEQ ID NO:2. In some embodiments, the amino acid substitution corresponding to position 610 of SEQ ID NO:2 is any amino acid other than Y. In some embodiments, the amino acid substitution at the amino acid corresponding to position 610 of SEQ ID NO:2 is A, R, N, C, I, L, K, M, F, P, S, W, V, D, H, G, Q, T, or E. In some embodiments, the amino acid substitution corresponding to position 610 of SEQ ID NO:2 is any amino acid other than P. In some embodiments, the amino acid substitution at the amino acid corresponding to position 610 of SEQ ID NO:2 is A, R, N, C, I, L, K, M, F, S, W, Y, V, D, H, G, Q, T, or E. In some embodiments, the amino acid substitution at the amino acid corresponding to position 610 of SEQ ID NO:2 is F.

In some embodiments, the amino acid substitution(s) comprise at least an amino acid substitution corresponding to position 791 of SEQ ID NO:2. In some embodiments, the amino acid substitution corresponding to position 791 of SEQ ID NO:2 is any amino acid other than N. In some embodiments, the amino acid substitution at the amino acid corresponding to position 791 of SEQ ID NO:2 is A, R, C, I, L, K, M, F, P, S, W, Y, V, D, H, G, Q, T, or E. In some embodiments, the amino acid substitution at the amino acid corresponding to position 791 of SEQ ID NO:2 is I.

In some embodiments, the amino acid substitution(s) comprise a combination of two, three, four, five, six, seven, eight, nine, ten, eleven, twelve, or more substitutions. For example, in some embodiments, the amino acid substitution(s) comprise a combination of two or more substitutions at the amino acids corresponding to positions 363, 375 and 610 of SEQ ID NO:2. In some embodiments, the combination of amino acid substitutions comprises a Y to C substitution at the amino acid corresponding to position 363 of SEQ ID NO:2, a Y to F substitution at the amino acid corresponding to position 375 of SEQ ID NO:2, and/or a Y (or P) to F substitution at the amino acid corresponding to position 610 of SEQ ID NO:2. In some embodiments, the combination of amino acid substitutions comprises a Y363C, a Y375F, and/or a Y610F substitution in SEQ ID NO:2.

In some embodiments, the amino acid substitution(s) comprise a combination of substitutions at the amino acids corresponding to positions 70 and 139 of SEQ ID NO:2. In some embodiments, the combination of amino acid substitutions comprises a L to S substitution at the amino acid corresponding to position 70 of SEQ ID NO:2, and an I (or V) to F substitution at the amino acid corresponding to position 139 of SEQ ID NO:2. In some embodiments, the combination of amino acid substitutions comprises a L70S and an I139F substitution in SEQ ID NO:2.

In some embodiments, the amino acid substitution(s) comprise a combination of substitutions at the amino acids corresponding to positions 167 and 286 of SEQ ID NO:2. In some embodiments, the combination of amino acid substitutions comprises a L to M substitution at the amino acid corresponding to position 167 of SEQ ID NO:2, and an A (or S) to D substitution at the amino acid corresponding to position 286 of SEQ ID NO:2. In some embodiments, the combination of amino acid substitutions comprises a L67M and an S286D substitution in SEQ ID NO:2.

In some embodiments, the amino acid substitution(s) comprise a combination of two or more substitutions at the amino acids corresponding to positions 136, 376 and 791 of SEQ ID NO:2. In some embodiments, the combination of amino acid substitutions comprises a G to C substitution at the amino acid corresponding to position 136 of SEQ ID NO:2, an E to K substitution at the amino acid corresponding to position 376 of SEQ ID NO:2, and/or an N to I substitution at the amino acid corresponding to position 791 of SEQ ID NO:2. In some embodiments, the combination of amino acid substitutions comprises a G136C, an E376K, and/or an N791I substitution in SEQ ID NO:2.

In some embodiments, the amino acid substitution(s) comprise one or more substitutions at positions 66, 70, 136, 139, 167, 250, 286, 363, 375, 376, 610, and/or 791 of a polypeptide substantially identical to SEQ ID NO:2, 4, 6, 8, 10, 12, or 14.

A. Homology to Other Beta-Glucosidases

The improved beta-glucosidases described herein can be derived from any beta-glucosidase having the desired activity (e.g., converts cellobiose to glucose). Based on amino acid sequence and structural similarity, known beta-glucosidases have been assigned to Glycoside Hydrolase (GH) families GH1, GH3, GH5, GH9, GH30, and GH116 (see, e.g., Thongpoo et al., "Identification of the acid/base catalyst of a glycoside hydrolase family 3 (GH3) β-glucosidase from *Aspergillus niger* ASKU28," Biochimica et Biophysica Acta 1830 (2013) 2739-2749). Thus, the improved beta-glucosidases can be modified from GH families GH1, GH3, GH5, GH9, GH30, and GH116. In some embodiments, the improved beta-glucosidase is a modified GH3 beta-glucosidase. In some embodiments, the improved beta-glucosidase is a modified GH3 sub-family 4 beta-glucosidase.

As described in Thongpoo et al., the catalytic residues are, in general, highly conserved both within a particular GH family, and among a group of families comprising a GH clan. In addition, even in the absence of conserved sequence alignment, the three dimensional homology modeling suggests that the structure of beta-glucosidases from divergent species is conserved (e.g., see the structural superimposition of the three-dimensional model of *A. niger* beta-glucosidase with the crystal structure of barely ExoI in complex with glucose shown in FIG. 1 of Thongpoo et al.). Therefore, one of skill in the art would understand which regions of the unmodified beta-glucosidase can be substituted and still retain the catalytic activity, and which regions are sensitive to mutations.

In some embodiments, the amino acid substitutions described herein are located in conserved domains or motifs. These domains are conserved among fungal beta-glucosidases. In some embodiments, the domains are conserved among beta-glucosidases from the genus *Aspergillus*. Examples of the conserved domains that comprise the amino acid substitutions described herein include the following:

```
                                         (SEQ ID NO: 16)
EKVNLTTGTGWELELCVGQTGGVPRLG (corresponding to
amino acids 58-84 of SEQ ID NO: 2);

(SEQ ID NO: 17)
AMGQEFSDKGADIQLGPAAGPLGRSPDGGRN (corresponding to
amino acids 127-157 of SEQ ID NO: 2);

(SEQ ID NO: 18)
EGFSPDPALSGVLFAETIKGIQ (corresponding to amino
acids 159-180 of SEQ ID NO: 2);

(SEQ ID NO: 19)
GAVMCSYNQINNSYGCQNS (corresponding to amino acids
242-260 of SEQ ID NO: 2);

(SEQ ID NO: 20)
GFQGFVMSDWAAHHAGVSGALAGLDMSMPGD
(correspondingto amino acids 272-302 of
SEQ ID NO: 2) (nucleophile D280 in bold);

(SEQ ID NO: 21)
EYGYKYYYVSEGPYEKVN (corresponding to amino acids
362-379 of SEQ ID NO: 2);

(SEQ ID NO: 22)
PFTWGKTREAYQDYLVTEPNNGNGAPQ (corresponding to
amino acids 597-623 of SEQ ID NO: 2);

(SEQ ID NO: 23)
VPQLYVSLGGPNEPKIVLRQFERI (corresponding to amino
acids 780-803 of SEQ ID NO: 2).
```

In some embodiments, the unmodified beta-glucosidase comprises the motif: GFQGFVMSDW $X_1$ A $X_2$ H $X_3$ GV $X_4$ $X_5$A $X_6$ AGLDM (SEQ ID NO:24; corresponding to positions 272 to 297 of accession no. CAB75696.1), wherein:

$X_1$ is A, T or W;
$X_2$ is H or Q;
$X_3$ is A, S, or T;
$X_4$ is S, G or A;
$X_5$ is G, A, or S; and
$X_6$ is L or V.

In some embodiments, the improved beta-glucosidases described herein comprise at least an amino acid substitution at position X3 of SEQ ID NO:24. Amino acid substitution at this position confers improved beta-glucosidase activity, yielding a mutant beta-glucosidase with an improved beta-glucosidase activity relative to the unmodified beta-glucosidase. In some embodiments, the amino acid at position $X_3$ is substituted with an amino acid that does not correspond to the respective motif as set forth in SEQ ID NO:24. Thus, in some embodiments, the amino acid at position $X_3$, if substituted, is not A, S, or T. In some embodiments, amino acid substitutions at position $X_3$ include R, N, C, I, L, K, M, F, P, W, Y, V, D, H, G, Q, or E (SEQ ID NO:25). In certain embodiments, the amino acid substitution at position $X_3$ is Aspartic Acid (D) (SEQ ID NO:26).

The *A. niger* CAB75696.1 beta-glucosidase is comparable to the *A. niger* ASKU28 variant described in Thongpoo et al. (2013). For example, the nucleophile site at position E490 of Thongpoo et al. corresponds to position E509 of CAB75696,1. Thus, by sequence alignment and relative spacing of residues identified therein, one can determine corresponding residues between the sequence of the *A. niger* ASKU28 variant and other fungal beta-glucosidases, and can therefore map the corresponding residues onto the structure described in Thongpoo et al.

In some embodiments, the improved beta-glucosidases described herein can be linked to another polypeptide to form a fusion protein. In some embodiments, the improved beta-glucosidases described herein are covalently linked to a heterologous polypeptide. In some embodiments, the improved beta-glucosidases described herein are linked to a heterologous polypeptide using a linker, such as a chemical crosslinking agent. In some embodiments, the improved beta-glucosidases described herein are joined to a heterologous polypeptide using genetic fusion, such that a nucleic acid (e.g., DNA) encoding both an improved beta-glucosidase and a heterologous polypeptide is translated to produce a fusion protein. The nucleic acid encoding the fusion protein can be operably linked to regulatory sequences, such as promoters, ribosome binding sites, and terminators, for efficient translation in a host cell. In some embodiments, the nucleic acid encoding the fusion protein comprises sequences encoding an amino acid linker between the improved beta-glucosidase and the heterologous protein. In some embodiments, the heterologous peptide that is the fusion partner of the improved beta-glucosidases described herein is a cellulosic enzyme or hydrolytic enzyme (e.g., an enzyme that degrades or hydrolyzes lignocellulosic biomass), such as but not limited to a cellulase, hemicellulase, or amylase. In some embodiments, the heterologous fusion peptide is an exoglucanse enzyme (e.g., a cellobiohydrolase such as CBHI or CBHII) or an endoglucanase.

III. Nucleic Acids

The improved beta-glucosidase polypeptides described herein can be encoded by a polynucleotide (e.g., DNA) comprising a nucleic acid. Thus, in some embodiments, the instant disclosure provides nucleic acids encoding the improved beta-glucosidases described herein. In some embodiments, the nucleic acids encode polypeptides that are substantially identical (e.g., at least 40%, 45%, 50%, 55%, 60%, 65%, 70%, 75%, 80%, 85%, 90%, 91%, 92%, 93%, 94%, 95%, 96%, 97%, 98%, 99% sequence identity) to any of SEQ ID NOS: 2, 4, 6, 8, 10, 12, or 14. In some embodiments, the nucleic acids encode polypeptides comprising the amino acid sequence of SEQ ID NO: 2, 4, 6, 8, 10, 12, or 14. In some embodiments, the nucleic acid comprises SEQ ID NO: 1, 3, 5, 7, 9, 11 or 13. In some embodiments, the nucleic acids encode modified polypeptides having improved beta-glucosidase activity that are substantially identical to an *Aspergillus* sp. beta-glucosidase. In some embodiments, the nucleic acids encode modified polypeptides having improved beta-glucosidase activity that are substantially identical to an *Trichoderma* sp. beta-glucosidase.

IV. Expression Vectors

The improved beta-glucosidases or other enzymes discussed herein may be recombinantly expressed by molecular cloning into an expression vector containing a suitable promoter and other appropriate transcription regulatory elements, and transferred into prokaryotic or eukaryotic host cells to produce recombinant enzymes. Techniques for such manipulations are fully described by Sambrook et al. (Molecular Cloning: A Laboratory Manual; Cold Spring Harbor Laboratory, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990)).

A variety of techniques are available and known to those skilled in the art for introduction of nucleic acid constructs into a cellular host. Transformation of microbial cells may be accomplished through, e.g., use of polyethylene glycol, calcium chloride, viral infection, DEAE dextran, phage infection, electroporation and other methods known in the art. Transformation of fungus, in particular *Pichia*, may be accomplished, for example, according to "*Pichia* Protocols", in *Methods Mol. Biol.*, Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like.

Polynucleotides comprising a nucleic acid encoding the improved beta-glucosidases are also provided. In some embodiments, the polynucleotide comprises an expression cassette comprising a heterologous promoter operably linked to the nucleic acid. Also provided herein are vectors comprising the polynucleotides provided herein, and isolated cells or culture of cells comprising the polynucleotides that is heterologous to the cell. In some embodiments, the cell is a bacteria or yeast cell. In some embodiments, the cell is a *Saccharomyces cerevisiae*.

V. Yeasts

In some embodiments, the improved beta-glucosidases or other enzymes discussed herein are expressed in one or more yeast strain. Any yeast strain can be used according to the present invention. Yeast are unicellular microorganisms that belong to one of three classes: Ascomycetes, Basidiomycetes and Fungi Imperfecti. While pathogenic yeast strains, or nonpathogenic mutants thereof, can be used in accordance with the present invention, nonpathogenic yeast strains will generally be used. Exemplary genera of yeast strains include *Saccharomyces*, *Candida*, *Cryptococcus*, *Hansenula*, *Kluyveromynces*, *Pichia*, *Rhodotorula*, *Schizosaccharomyces* and *Yarrowia*. Exemplary species of yeast strains include *Saccharomyces cerevisiae*, *Saccharomyces carlsbergensis*, *Candida albicans*, *Candida kefyr*, *Candida tropicalis*, *Cryptococcus laurentii*, *Cryptococcus neoformans*, *Hansenula anomala*, *Hansenula polymorpha*, *Kluyveromyces fragilis*, *Kluyveromyces lactis*, *Kluyveromyces marxianus* var. *lactis*, *Pichia pastoris*, *Rhodotorula rubra*, *Schizosaccharomyces pombe*, and *Yarrowia lipolytica*. It is to be appreciated that a number of these species include a variety of subspecies, types, subtypes, etc. that are meant to be included within the aforementioned species. In some embodiments, a yeast strain capable of replicating plasmids to a particularly high copy number is used. In some embodiments, a temperature-tolerant yeast strain is used. In some embodiments, an inhibitor-tolerant yeast strain is used.

The present invention provides for yeast strains that express the improved beta-glucosidases or other enzymes discussed herein. Yeast expressing the improved beta-glucosidases or other enzymes discussed herein can be generated as is known in the art. For example, expression cassettes comprising a promoter operably linked to a coding sequence for the improved beta-glucosidases or other enzymes discussed herein can be (optionally inserted into a nucleic acid vector and) introduced into the yeast. A number of expression vectors for various yeast species are known in the art and some can be obtained commercially. Vectors can optionally include an origin of replication and/or a marker gene for identifying cells transformed with the vector. In some embodiments, the expression cassettes are stably introduced into a yeast chromosome or extrachromosomal DNA.

Any number of promoters can be used to drive expression from the expression cassettes of the invention. Exemplary promoters include, e.g., constitutive or inducible promoters. Recombinant gene expression can be driven by promoters including, but not limited to, the yeast GAL10 gene promoter, the glycerol 3-phosphate dehydrogenase (GPD promoter, the phosphoglycerate kinase (PGK) promoter (see, e.g., Tuite, M. F. et. al. (1982) *EMBO Journal* 1, 603-608; WO 84/04757), GAL10/PGK promoter chimeras (see, e.g., U.S. Pat. No. 5,739,007) or other yeast promoters such as alcohol dehydrogenase (see, e.g., Bennetzen, J. L. and Hall, B. D. *J. Biol. Chem.* 257:3018 (1982); Ammerer, G. in *Methods in Enzymology* Vol. 101, p. 192 (1983)) phosphoglycerate kinase (see, e.g., Derynck, R., Hitzemann, R. A., Gray, P. W., Goeddel, D. V., in *Experimental Manipulation of Gene Expression*, 1983, p. 247, ed. M. Inouye, Academic Press), triose phosphate isomerase (see, e.g., Alber, T. and Kawasaki, G., *J. Molec and Applied Genet.* 1: 419-434 (1982)), or enolase (see, e.g., Innes, M. A. et al. *Science* 226:21 (1985)) can be used in a similar manner.

The yeast can be engineered to secrete proteins into a cellulose source (e.g., a fermentation "mash" or other saccharifiable biomass material) at a balanced rate of production that controls the rate of fermentation by control of enzyme expression. By the careful selection of promoters driving expression of the enzymes, the level of protein production can be gated, permitting fermentations to proceed at measured or controlled rates. In other words, the rate of sugar production (or ethanol production) is controlled by release of enzymes.

Expression vectors used in yeast cells can also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Yeast cells can be engineered to secrete the improved beta-glucosidases or other enzymes discussed herein or optionally can be engineered such that the proteins are active and attached to the surface of the yeast cells. A variety of methods are known for secretion of heterologous proteins from yeast. See, for example, US Patent Publication Nos. 2007/0077619 and 2006/0234351 and European Patent EP0256421. In some embodiments, secretion is achieved by inclusion of an appropriate signal sequence as a fusion with the enzyme. Exemplary signal sequences are described in the art, including but not limited to, U.S. Pat. No. 5,521,086.

Optionally, one or more of the enzymes expressed from a yeast strain is attached to the surface of the yeast cell. In some embodiments, the proteins of the present invention are fused to α-agglutinin or a fragment thereof, resulting in surface expression. See, e.g., Murai et al., *Applied and Environmental Microbiology*, 64(12):4857-4861 (1998).

VI. Method for Converting a Cellulose-Containing Biomass Feedstock to Ethanol

In some embodiments, the cellulose-containing biomass feedstock is added directly to the mutant beta-glucosidases provided herein (e.g., as expressed in yeast cultures/suspensions) to form an aqueous mixture and incubated under conditions to allow for efficient conversion of the cellulose-containing biomass feedstock to simple sugars. If desired, the sugars can then be further converted to ethanol via fermentation or can be converted to other desired products. Accordingly, provided herein are methods for converting a cellulose-containing biomass feedstock to ethanol by using procedures including treating the biomass with a mutant beta-glucosidase provided herein. In some embodiments, the cellulose-containing biomass feedstock is first converted into sugar, and the resulting sugar is subsequently converted into ethanol (e.g., by other components or by a yeast cell). In some embodiments, the cellulose-containing biomass feedstock is corn grain or corn stover.

In some embodiments, the cellulose-containing biomass feedstock is contacted with a cell expressing a heterologous beta-glucosidase, e.g., the mutant beta-glucosidases provided herein. The heterologous beta-glucosidase-expressing cell can be any cell known in the art, including bacteria, yeast, insect, or mammalian cells.

Mixture of the cellulose-containing biomass feedstock with a cell (e.g., a yeast cell) expressing the heterologous beta-glucosidase allows for efficient conversion of the cellulose-containing biomass feedstock into sugars without costly purification of enzymes. Further, in some embodiments, the cell (e.g., a yeast cell) also ferments the resulting sugar into alcohol (e.g., ethanol and/or butanol). This aspect is particularly advantageous because accumulation of sugars can in some instances act to inhibit the enzymes' activities. By fermenting the sugars into alcohols, the cell (e.g., a yeast cell) increases the overall production and speed of conversion of the cellulose-containing biomass feedstock into sugars and ultimately into alcohols. Thus, in some embodiments, the cell (e.g., a yeast cell) expresses the heterologous beta-glucosidase provided herein during fermentation and/or saccharification, and optionally such that saccharification and fermentation occur simultaneously. Accordingly, provided herein are methods for converting a cellulose-containing biomass feedstock to ethanol by treating the biomass with a cell (e.g., a yeast cell) expressing a heterologous beta-glucosidase. In some embodiments, the cell is a yeast cell. In some embodiments, the cell is a *Saccharomyces cerevisiae*. In some embodiments, the cell is a *Pichia*. In some embodiments, the cellulose-containing biomass feedstock is first converted into sugar, and the resulting sugar is subsequently converted into ethanol. In some embodiments, the cellulose-containing biomass feedstock is corn grain. Heterologous beta-glucosidases useful for the methods provided herein also include improved beta-glucosidases provided herein.

In some embodiments, the cellulose-containing biomass feedstock is first pretreated to render the cellulose more available to the enzymes. In some embodiments, the feedstock is ground into finer pieces or otherwise treated to increase surface area of the material. In some embodiments, the pre-treatment comprises at least one of the following: acid hydrolysis (see, e.g., U.S. Pat. Nos. 4,174,976 and 5,597,714; and PCT Publication WO/2006/086861), steam explosion (see, e.g., U.S. Pat. No. 6,506,282 and PCT Publication WO/2000/039387), autohydrolysis, ionic liquids (see, e.g., U.S. Pat. No. 6,824,599), hot water, ammonia explosion (see, e.g., U.S. Pat. No. 5,037,663), extrusion (see, e.g., U.S. Pat. No. 7,037,096), or microwave treatment (see, e.g., U.S. Pat. No. 5,196,069).

In some embodiments, the cellulose-containing biomass feedstock is first pretreated to render biomass particles having small sizes (e.g., milled). It has been noted that yield of biofuel (e.g., ethanol) can be improved by using biomass particles having small sizes, e.g., biomass particles having a relatively uniform particle size of less than 1600 microns. For example, in some embodiments, at least 95% of the pretreated biomass particles have a particle size from about 100 microns to about 800 microns, or a particle size from about 100 microns to about 500 microns. Pretreated biomass particles can be generated by, e.g., a hammer mill or a colloid mill or a shear mill or a cavitation mill; serial combinations of any two or more of these can also be employed. For example, the colloidal mill can be used to select the resulting particle size distribution through the use of gap rotational controls. A relatively precise particle size distribution can be obtained from much larger biomass material using a colloid mill in contrast to alternative pretreatment techniques such as comminution with a hammer mill. An appropriate gap size on the colloid mill can produce a highly uniform suspension of biomass, where the maximum particle size of the biomass is greatly reduced and significantly more uniform compared to using only the comminution device. The radial gap size for a colloidal mill used in a corn ethanol plant can range from 0.104-0.728 millimeters, e.g., from 0.104-0.520 millimeters, e.g., from 0.208-0.520 millimeters, such that the resulting particle sizes are in the range of 100-800 microns. For example, in some embodiments, a gap setting of 0.1-0.15 is used for corn stover or other cellulosic biomass and a gap setting of 0.2-0.3 mm is used for grains including but not limited to corn kernels. As a second example, a shear mill can be used to reduce particle size of cellulose-containing materials under high shear action, especially for fibrous woody material. In shear milling, the material is processed through several generator stages (typically three) of a dispersing device which produces very fine suspensions. The stages consist of rotor-stator combinations to reduce particle size and create a very narrow size distribution from larger-sized woody feedstock material. Various combinations of generators can be used to achieve desired particle size reductions, such as suspensions containing particles in the range of 100 to 300 microns. Techniques for generating biomass particles having small sizes are fully described by, e.g., U.S. Patent Application Publication No. 20100055741, the content of which is incorporated by reference in its entirety herein.

In some embodiments, fermentation temperatures will be controlled between 28-35° C. and pH 4.0-5.5. In some embodiments, a temperature-tolerant yeast cell strain can be used, and accordingly a higher fermentation temperature can be used (e.g., at or above 35° C., 36° C., 37° C., 38° C., 39° C., or 40° C.). There are other factors affecting enzyme activity (e.g., BG activity) including surface area, pore volume, pore size distribution of the cellulose-containing biomass feedstock, pretreatment method, and the presence or absence of inhibitors such as furfurals. Many enzymes require the presence of an additional, nonprotein, cofactor. Some of these are metal ions such as $Ca^{2+}$, $Zn^{2+}$, $Cu^{2+}$, $Mn^{2+}$, $K^+$, and $Na^+$, which are commonly present in biomass. Some cofactors are small organic molecules called coenzymes. The B vitamins thiamine (B1), riboflavin (B2) and nicotinamide are precursors of some coenzymes. Coenzymes may be covalently bound to the protein part (called the apoenzyme) of enzymes as a prosthetic group. Others bind more loosely and, in fact, may bind only transiently to the enzyme as it performs its catalytic act. These are normally present in enough concentration in typical fermentations, however if they are deficient, they can be added to the fermenter in order to enhance the conversion.

In some embodiments, the cellulose-containing biomass feedstock can be used as an inexpensive form of sugar (i.e., for value added products). In some of these embodiments, excess sugar is bled from the saccharification tank(s) (i.e., where the enzymes are converting plant material to sugar), for example using a sequential membrane, filtrate wash, or other sugar removal system. This reduces the sugar concentration in the saccharification tank(s) and allows for hydrolysis to continue without being inhibited by excess sugar. Residual non-sugar producing solids can be optionally purged forward for further processing or for other uses (such as for fuel value in a cogeneration system).

In some embodiments, the improved beta-glucosidase can be supplemented into the saccharification mixture to increase saccharification of the biomass. In some of these embodiments, the improved beta-glucosidase can be supplemented into the solids fraction of a saccharification reaction that has been separated from a liquids fraction by a solids/liquid separation method.

Furfurals and other carbohydrate-derived and lignin-derived compounds arising from the biomass pretreatment process are present in some saccharification reactions. Furfurals can in some embodiments act as yeast growth inhibitors. In some embodiments, bacteria that consume furfurals can also be added to the fermentation to selectively reduce or eliminate the furfurals. In some embodiments, compounds that selectively bind furfural but not sugars, such as activated carbon, can be added prior to the fermentation to selectively reduce or eliminate the furfurals.

In some embodiments, the mixture of yeast cells and the cellulose-containing biomass feedstock are incubated to result in production of sugars from cellulose or other plant material and subsequent fermentation of the sugars into alcohols. Industrial fermentation conditions are known in the art. In some embodiments, a modified form of Simultaneous Saccharification and Fermentation (SSF) can be accomplished by using a small saccharification step in order to produce a small amount of sugar to promote yeast growth. This partially converted media is then sent to the fermenter. After the fermenter volume is approximately 10-20% of the total fermenter volume the yeast inoculum is added. The tank is then continuously filled in a fed batch mode over a period of 25-35 hours and then held at 35° C. until the fermentation is complete (~72 hrs). This allows sufficient use of the sugars to prevent inhibition of the process. To improve alcohol production, yeast strains with a high ethanol tolerance can be selected. In some embodiments, yeast growth stimulants can also be added to the mixture. For example, sterols can be added to stimulate yeast growth and enzyme production.

In some embodiments, the yeasts provided herein are exceptionally efficient for the production of ethanol. However, some of the same yeasts can be used for saccharification without subsequent fermentation. This can be accomplished, for example, by, e.g., allowing the yeasts to generate biomass hydrolysate, limiting ethanol production, followed by deactivation of the yeast so the fluid contains free enzymes and proteins. In the case of yeasts that have the expressed enzymes attached to the surface, the yeasts can be cultivated, deactivated with ultrasound and then used as immobilized enzymes within the saccharification vessel. The yeast can be filtered at the end of the saccharification process along with the other solids in this manner.

In some embodiments, the mixture of yeast cells and the cellulose-containing biomass feedstock are incubated to result in production of biomass-derived intermediates from cellulose or other plant material. As defined herein, the term "biomass-derived intermediate" refers to a carbohydrate intermediate derived from biomass hydrolysis. In some embodiments, the biomass-derived intermediates are simple sugars, e.g., monosaccharides and disaccharides such as glucose, fructose, mannose, and galactose, sucrose, maltose, lactose, cellobiose, and derivatives thereof. In some embodiments, the biomass-derived intermediates are partial hydrolysis or partial depolymerization intermediates, e.g., cellobiose. In some embodiments, the biomass-derived intermediates are non-sugar biomass-derived intermediates.

In some embodiments, the non-sugar biomass-derived intermediates are polyols, e.g., sorbitol, anhydrosorbitol, glycerol, and propanediol. In some embodiments, the non-sugar biomass-derived intermediates are isomerization and dehydration products derived from biomass hydrolysis and fermentation process, e.g., "reversion products," "acyclic intermediates," and "fructofuranosyl intermediates" as described in Chheda et al., *Angew. Chem. Int. Ed.* 46:7164-7183, 2007. In some embodiments, the non-sugar biomass-derived intermediates are additional dehydration and fragmentation products of acyclic intermediates and fructofuranosyl intermediates as described in Chheda et al., *Angew. Chem. Int. Ed.* 46:7164-7183, 2007. In some embodiments, the non-sugar biomass-derived intermediates include furans, e.g., furfural, 5-hydroxymethylfurfural, di-formylfuran, and derivatives thereof (e.g., 2,5-furandicarboxylic acid, di(hydroxymethyl) tetrahydrofuran, methyl tetrahydrofuran). Additional examples of biomass-derived intermediates are known in the art and disclosed in Chheda et al., *Angew. Chem. Int. Ed.* 46:7164-7183, 2007. In some embodiments, the non-sugar biomass-derived intermediates are amino acids and organic acids, such as levulinic acid, formic acid, fumaric acid, aspartic acid, succinic acid, malic acid, 3-hydroxypropionic acid, aspartic acid, itaconic acid, glutamic acid, glucaric acid, gluconic acid. If desired, any of the above products (i.e., sugar biomass-derived intermediates or non-sugar biomass-derived intermediates) can be further purified from the remainder of the reaction mixtures and/or chemically or enzymatically converted to yet another desired product.

The activity or amount of substrate hydrolysis of the improved beta-glucosidases described herein can be determined either directly or indirectly. Examples of direct measurements include activity assays such as the pNPG or cellobiose conversion assay described in the Examples. The improved activity can also be determined by measuring the amount of glucose produced by enzymatic treatment of cellulosic biomass using an improved beta-glucosidase described herein.

The amount of ethanol produced is dependent on the properties of individual yeast strains. Further, the properties of individual yeast strains can change over time and under different culture conditions. Thus, two yeast strains derived from the same parental strain can produce different amounts of ethanol or convert sugars to ethanol at different rates under the same culture conditions. These differences between strains can be due to changes that are independent of the mutations described herein, such that the amount of ethanol obtained during fermentation can result from efficient glucose to ethanol conversion that is due to strain genetics and/or increased beta-glucosidase activity.

In some embodiments, the amount of substrate hydrolysis by an improved beta-glucosidase can be determined indirectly by measuring the carbohydrate composition remaining after a fermentation reaction. For example, in some embodiments, there is a decrease in the amount of carbohydrates that are derived from cellulose and hemicellulose in the post-fermentation sample when the biomass is fermented with yeast expressing an improved beta-glucosidase. A decrease in carbohydrates in the post-fermentation carbohydrate composition indicates that more complex carbohydrates, such as glucan and xylan, were converted to fermentable sugars glucose and xylose, which serves as an indirect way to determine the activity of the improved beta-glucosidases described herein.

EXAMPLES

The following examples are offered to illustrate, but not limit the claimed invention.

Example 1

This example describes the production of a recombinant yeast strain that expresses beta-glucosidase activity.

The beta-glucosidase (BG) gene from *Aspergillus niger* (Accession #CAB75696.1) was integrated into the TR3 yeast background at the T4U3 genomic site. This BG gene contained a *Saccharomyces* codon-optimized BG open reading frame, a SUC2 secretion signal and demonstrated BG activity as described below.

To construct an expression vector suitable for expressing wild-type beta-glucosidase in yeast, the beta-glucosidase open reading frame was PCR amplified from commercially synthesized DNA using the Phusion high fidelity polymerase (Finnzymes/NEB). The amplified DNA fragment was cloned into a vector harboring a YPRC Tau3 targeted integration cassette under control of the GPD (TDH3) promoter and the SUC2 full secretion signal. Full length integration cassettes were amplified from plasmids recovered from transformed yeast strains demonstrating beta-glucosidase activity by cellobiose plate assay. These DNA integration cassettes were transformed into the haploid 40° C. yeast TR3 strain. Individual colonies obtained from the integration transformation were initially tested using both liquid culture and a color change cellobiose assay. A total of 15 strains were identified that demonstrated activity on both plates and in liquid culture. The presence of the open reading frame and integration at the YPRC Tau3 site were verified for all of these strains.

The cellobiose plate assay was used to compare the beta glucosidase activity of fifteen strains. Each strain was cultured overnight in csm-ura growth media. Cell counts were performed and 500,000 cells pelleted for each strain in triplicate. These cell pellets were resuspended in five ul of sterile water and spotted onto assay plates. Plates were placed at 30° C. and the color change zones measured at 24 and 48 hours. The diameter of the zone of color change was averaged for the three spots for each strain and compared to the negative control strain, which did not show BG activity.

The BG-expressing strains were subsequently used in corn mash and corn stover simultaneous saccharification and fermentation (SSF) studies using flask scale and pilot plant fermentations. A 12-gallon corn stover fermentation was performed at 40° C. in which the beta-glucosidase secreting yeast strain was co-inoculated with three other engineered yeast strains individually expressing endoglucanase II, CBH1, and CBHII. Surviving TR3 *Saccharomyces cerevisiae* yeast strains individually expressing BG, EGII, CBH1 or CBH2 were recovered by plating onto solid medium. A clonal population of BG-secreting yeast was isolated and the BG gene integration confirmed. This strain is referred to herein as yEdQ745 and comprises the wild-type BG gene. The BG sequence in the Tau3 integration cassette was used for subsequent mutagenesis experiments.

The above example demonstrates that yeast were successfully engineered to express and secrete active beta-glucosidase.

Example 2

This example describes the production of beta-glucosidase polypeptides having amino acid substitutions that improve enzyme activity.

Mutagenesis Strategy for BG:

Random mutagenesis of the BG gene was performed using Genemorph® II random mutagenesis kit (Stratagene). Primers were designed to target three regions within the beta glucosidase gene:
1. Within the open reading frame (ORF) of the gene.
2. Within the nucleophile site, 37 amino acids up and downstream from the aspartic acid residue.
3. Downstream from the nucleophile site, not including regions contained in above site.

The sequences of the primers used are provided below.
Primers Directed to BG's ORF:

```
                                       (SEQ ID NO: 27)
a. BG Orf FWD = 5' ATGAGATTTACTTTGATTGAAGCTG 3'.

(SEQ ID NO: 28)
b. Bg Orf REV = 5' CTAATGAACAGTTGGCAAAGAAG 3'.
```

Primers Directed to the Nucleophile Region:

```
                                       (SEQ ID NO: 29)
c. BG Cat FWD = 5' GGCCATTTGCTGATGCTATT 3'.

(SEQ ID NO: 30)
d. BG Cat REV = 5' CAACTCTCCATTGTGGAACAG 3'.
```

Primers Directed to the Enzyme Substrate Hydrolysis Region:

```
                                       (SEQ ID NO: 31)
e. BG Acid-Base FWD = 5' CTGTTCCACAATGGAGAGTTG 3'.

(SEQ ID NO: 32)
f. BG OrF REV = 5' CTAATGAACAGTTGGCAAAGAAG 3'.
```

Primers Used for Integration into Plasmid:

```
                                       (SEQ ID NO: 33)
g. EDQ.JHV.054 = 5' AGCGATAGACCITTGGTCCCCGGATCCC
CAATGAGATTTACTTTGATTGAAGCTG 3'.

(SEQ ID NO: 34)
h. EDQ.JHV.095 = 5'GACGGTATCGATAAGCTTGATATCGAATT
CCTAATGAACAGTTGGCAAAGAAG 3'.
```

Primers Used for Integration into Genome:

```
                                       (SEQ ID NO: 35)
i. Tau3up F1 = 5' GATCAAGATCGCTGCGTTGTTGTTGATGG 3'.

(SEQ ID NO: 36)
j. Tau3down R1 = 5' GATCTTGATCGAGCCCGTAATACAACAGTG
AG 3'.
```

Regions 2 and 3 were further modified using overlap extension polymerase chain reaction (PCR) to obtain the complete ORF. Once the complete ORF was obtained for all regions, they were transformed into the standard a3 vector (p414 GPD, ATCC#87356; CEN/ARS; TRP1 marked) via homologous recombination and tested as a plasmid-borne copy of the BG activity in yeast cells. The BG gene was codon optimized for expression in yeast, and the gene cassette contained a SUC2 secretion signal to enable secretion of the enzyme outside of the cell and into the growth medium.

Initial Phenotypic Screening of Plasmid-Borne BG Mutants in Transformed TR3 Yeast.

After transformation of plasmids encoding BG mutants and wild type BG control into yeast, colonies from the transformation went through functional screening for conversion of cellobiose to glucose. Several assays were tested, including a cellobiose gradient, a sodium dichlorindo-phenolate hydrate (DCPIP) plate or liquid assay, and a cellobiose challenge assay. Only the cellobiose challenge assay provided a good screening method.

The cellobiose challenge assay was performed in a 96 well plate to enable screening many colonies at once. Galactose was used as a carbon source to differentiate cell growth from galactose utilization (a non-preferred but metabolizable sugar for yeast) vs BG-mediated hydrolysis of cellobiose to glucose, and resulting utilization of glucose for cell growth.

The protocol for the assay is as follows: Individual yeast cell colonies containing mutagenized plasmid-borne BG were transferred to separate wells in a 96-well plate containing 0.5% galactose, 8% cellobiose substrate and selective growth medium CSM-ura with no additional sugars in a 500 ul total volume reaction. The plates were incubated at 30° C. with agitation for 48 hrs. Cells from wells that displayed cell growth were picked for further analysis of cellobiose conversion by HPLC. Clonal lines that exhibited >30% decrease in cellobiose levels compared to wild type were selected as candidates for genomic integration.

Phenotypic Screening of Selected BG Mutants Integrated into the TR3 Yeast Genome BG open reading frames of the above mutants showing reduced cellobiose levels in the cellobiose (CB) challenge assay were PCR amplified and integrated into TR3 yeast strain at the TAU3 integration site using homologous recombination. Wild type BG was also integrated into TAU3 to provide direct comparison of wild type and mutant BG activities.

The CB challenge assay was used to qualitatively screen the integrated mutants to compare phenotypes of plasmid-borne vs. integrated BG mutants; and to identify integration site-specific effects. FIG. 1 shows higher cellobiose conversion activity by mutant BG enzymes compared to wild type BG enzyme. The amount of cellobiose was significantly decreased in the mutants.

The above example shows that improved beta-glucosidase enzymes having increased activity on a cellobiose substrate were successfully produced.

Example 3

This example shows that the beta-glucosidase mutants described herein have increased activity in the presence of high glucose concentrations.

Initial Screening of Glucose Tolerance of Engineered BG Mutants

To further evaluate cellobiose conversion and resistance of BG activity to high glucose levels, the modified beta-glucosidase enzymes produced by the yeast strains described above were tested for glucose inhibition of beta-glucosidase activity. This experiment showed that a subset of BG mutants outperformed wild type BG in 3% cellobiose and 15% glucose conditions, and were only 40% less effective than Cellic® Ctec2 (Novozymes) or Accellerase® Trio™ (Genencor) in regards to cellobiose degradation at T=24. The high level of glucose used in this initial screening assay was to evaluate BG performance in conditions similar to corn mash fermentations where glucose levels at 8 hrs of fermentation can be >10% w/v. Subsequent high resolution glucose inhibition assays (described below) using various BG enzymes had lower cellobiose substrate and glucose levels more consistent with cellulosic biomass conversion processes comprising corn stover and bagasse.

Experimental Setup

All strains were tested in triplicate. BG mutant strains, a negative control strain (yEdQ623), and a wild type BG control strain were grown individually in 100 ml cultures of YPDC growth medium containing 8% glucose and incubated at 30° C. The supernatant (supe) was concentrated ~25-fold and protein levels normalized to 80 mg/ml. The supe was placed at 4° C. overnight before use in the enzyme assay. Beta-glucosidase enzyme activity was assayed using concentrated yeast cell culture supe containing BG activity in a reaction containing 3% cellobiose substrate and 15% glucose. The reaction samples were prepared as follows: 450 ul of 20% cellobiose, 1125 ul of 40% glucose, 925 ul of sodium citrate buffer (pH 4.8), 500 ul concentrated BG-containing supe, 3 ul each of antibiotics Lactrol and Allpen, and 3 ul of cyclohexamide. The reactions were incubated at 50° C. at 110 rpm agitation, and assayed for glucose and cellobiose concentrations by HPLC at T0, 4, 8, 12 and 24 hrs.

Results

Figure 2:
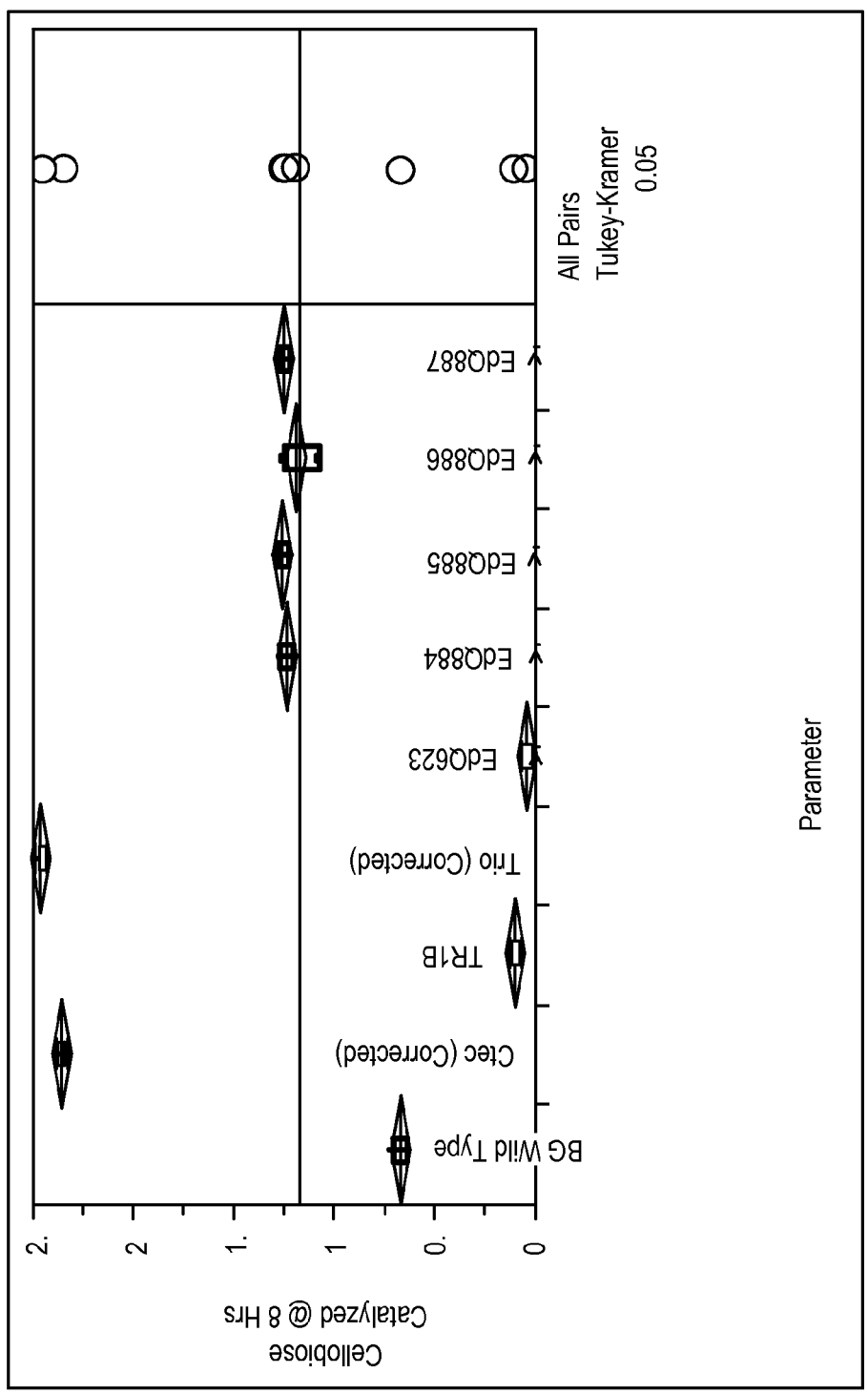
FIG. 2 shows statistical analysis of cellobiose catalyzed after 8 hrs by yeast strains expressing the modified beta-glucosidase enzymes described herein.
Figure 3A:
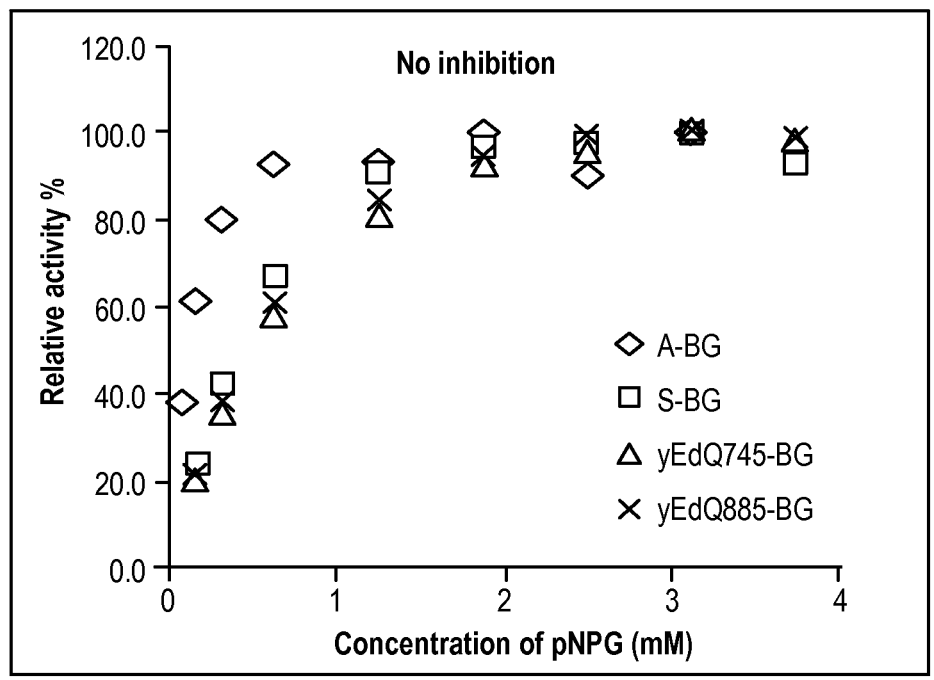
FIG. 3 shows a comparison of relative activity of different beta-glucosidase enzymes using pNPG substrate under various glucose inhibition conditions. (a) No inhibition; (b) 0.5 g/L glucose; (c) 0.9 g/L glucose; (d) 4.5 g/L glucose; (e) 9 g/L glucose condition; (f) 18 g/L glucose; (g) 36 g/L glucose.
Figure 3B:
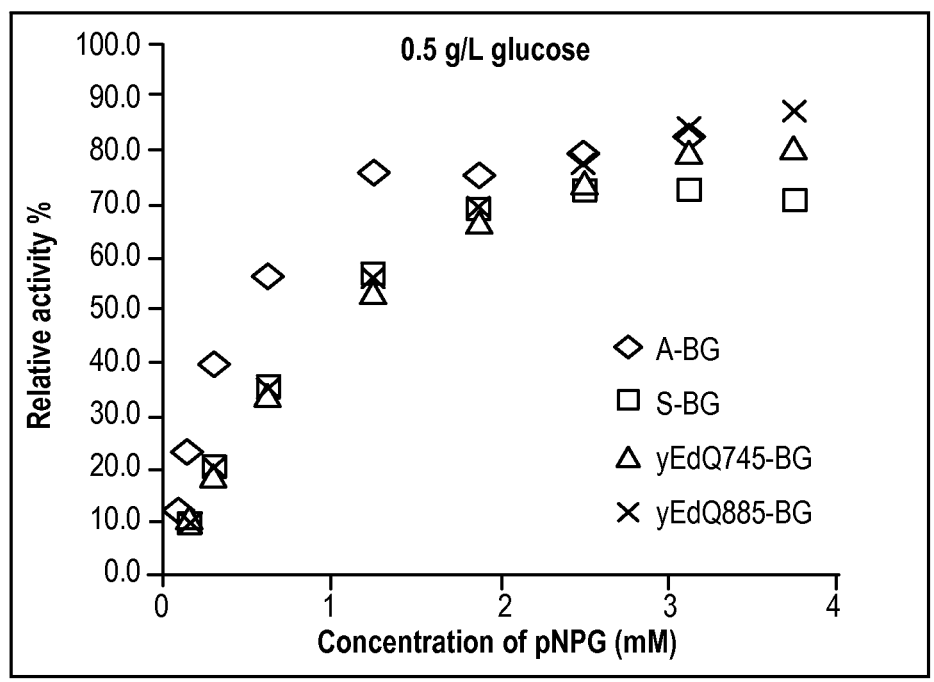
Figure 3C:
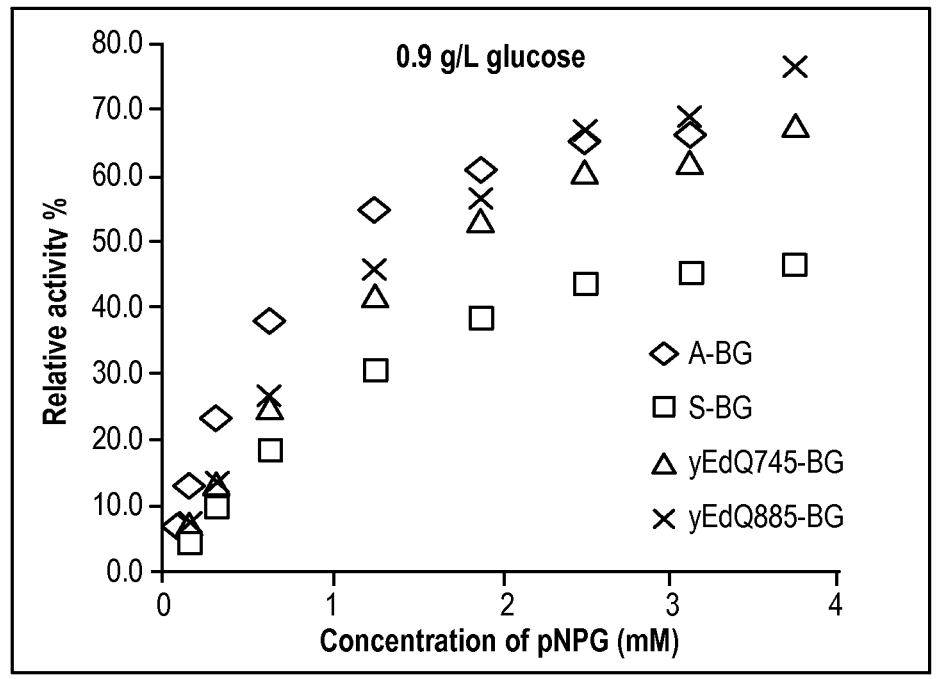
Figure 3D:
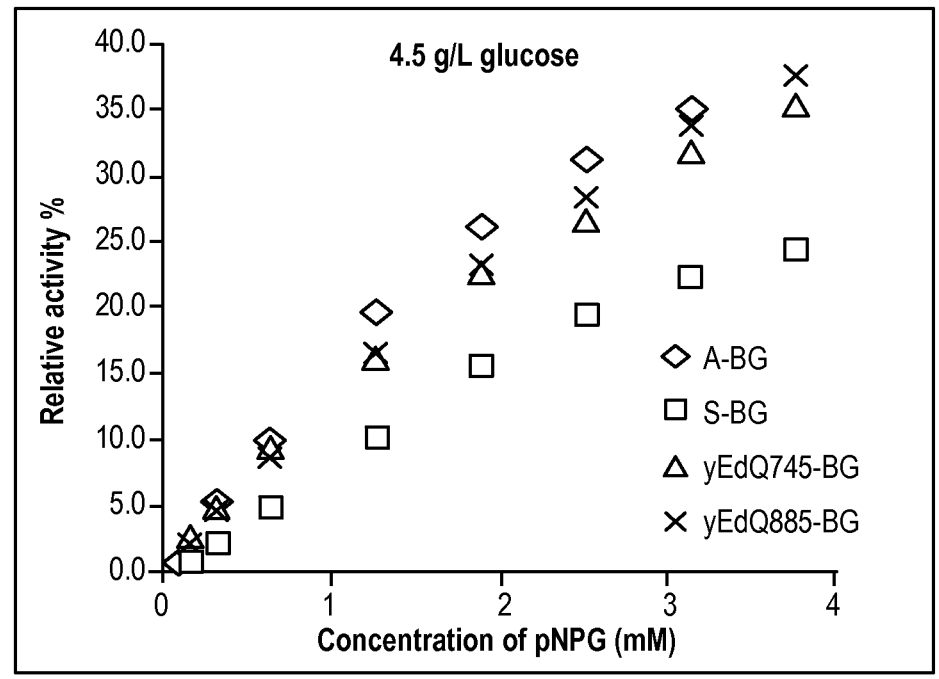
Figure 3E:
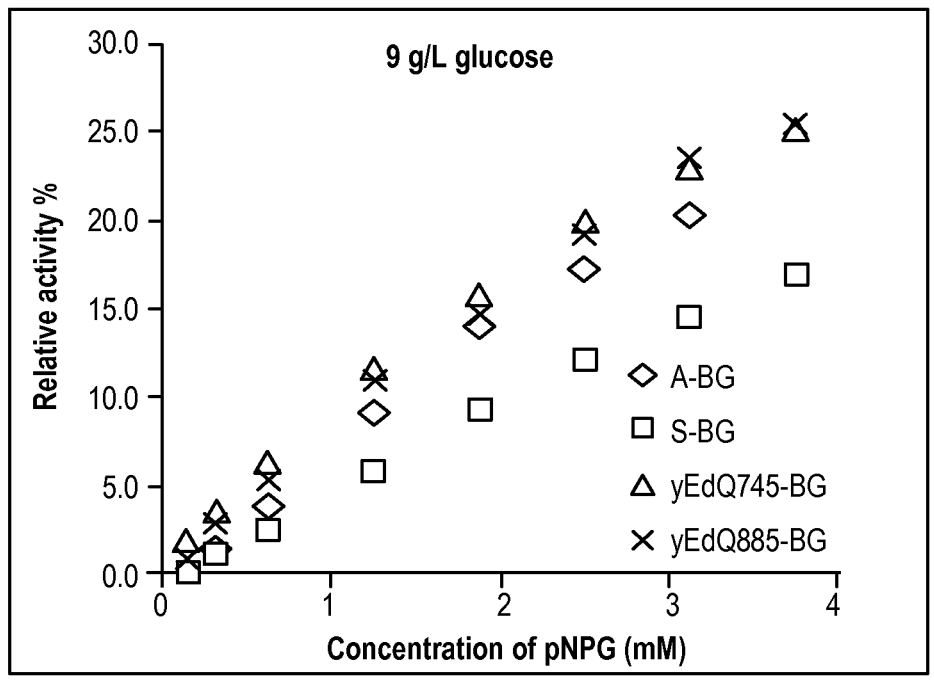
Figure 3F:
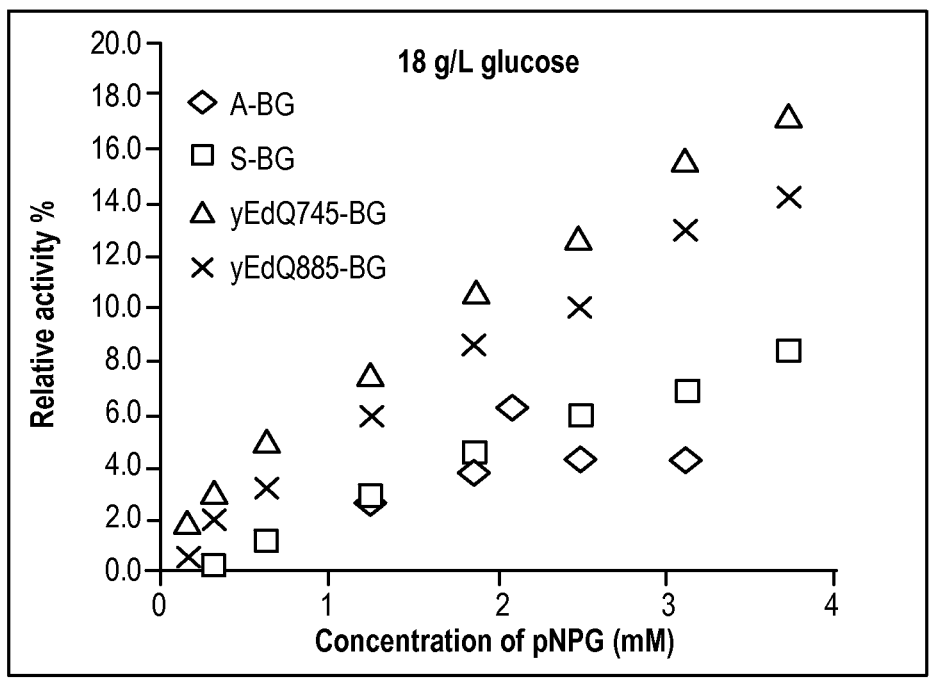
Figure 3G:
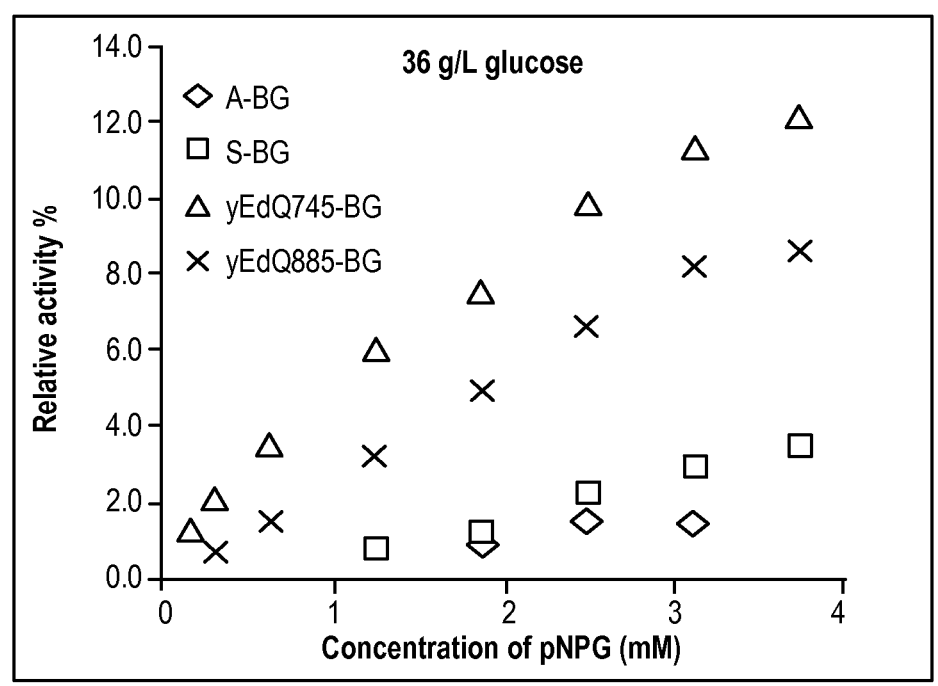
Figure 4A:
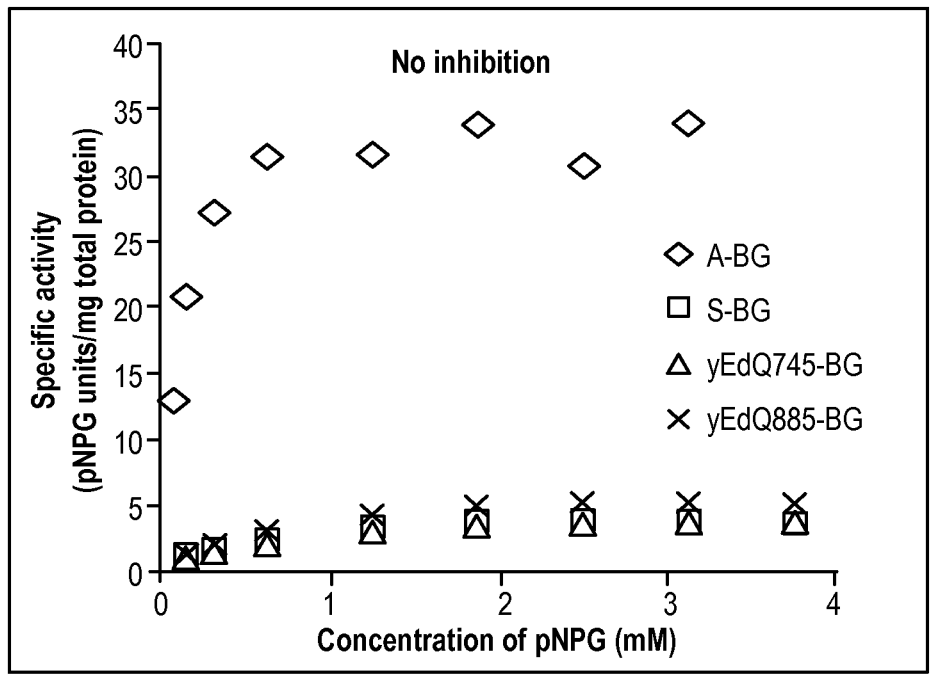
FIG. 4 shows a comparison of specific activity of different beta-glucosidase enzymes using pNPG substrate under various glucose inhibition conditions. (a) No inhibition; (b) 0.5 g/L glucose; (c) 0.9 g/L glucose; (d) 4.5 g/L glucose; (e) 9 g/L glucose condition; (f) 18 g/L glucose; (g) 36 g/L glucose.
Figure 4B:
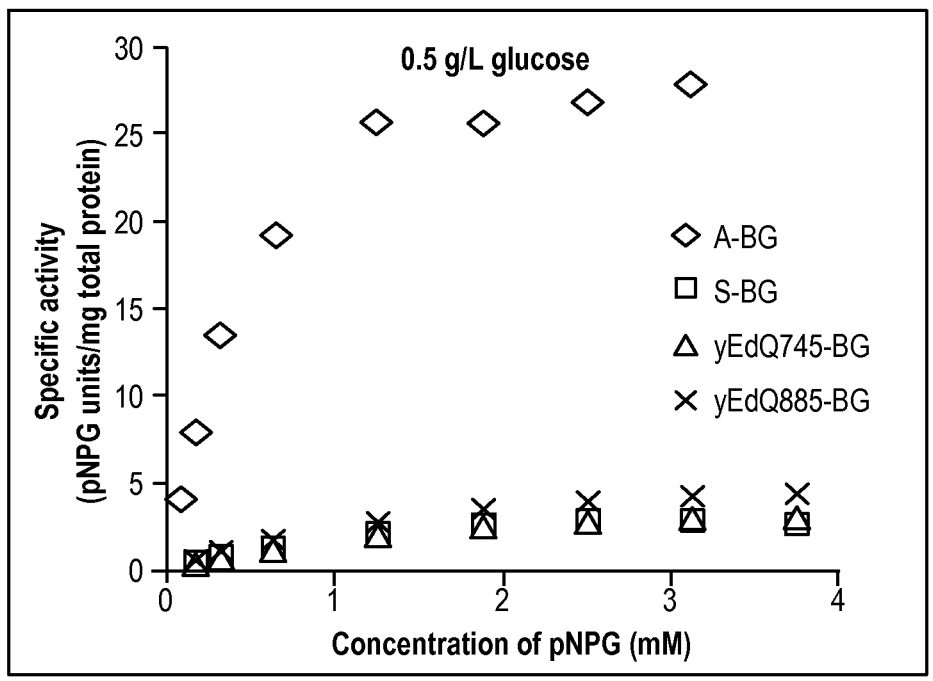
Figure 4C:
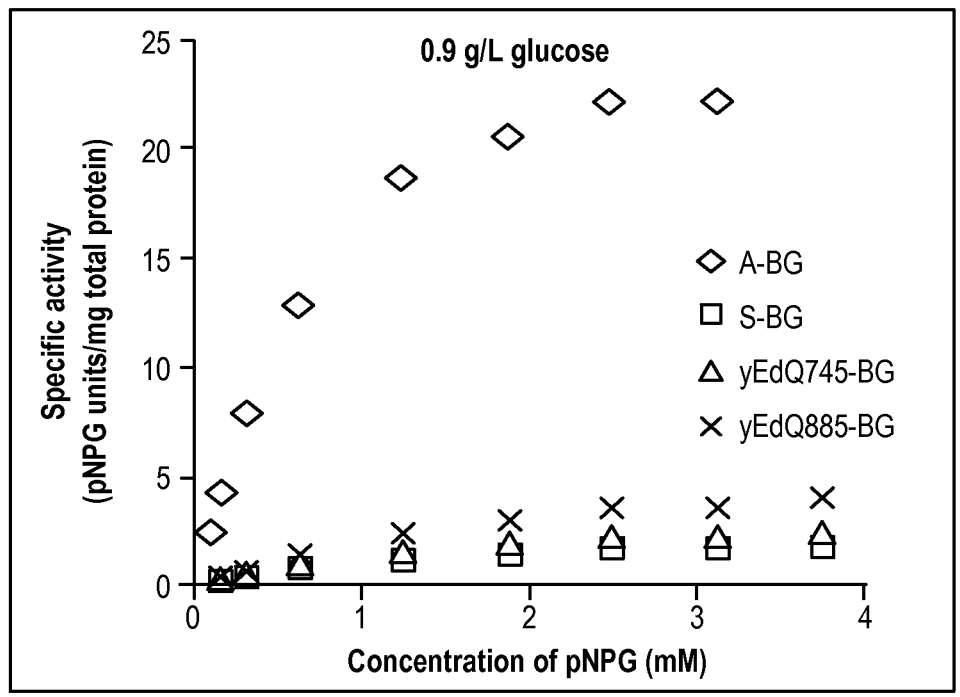
Figure 4D:
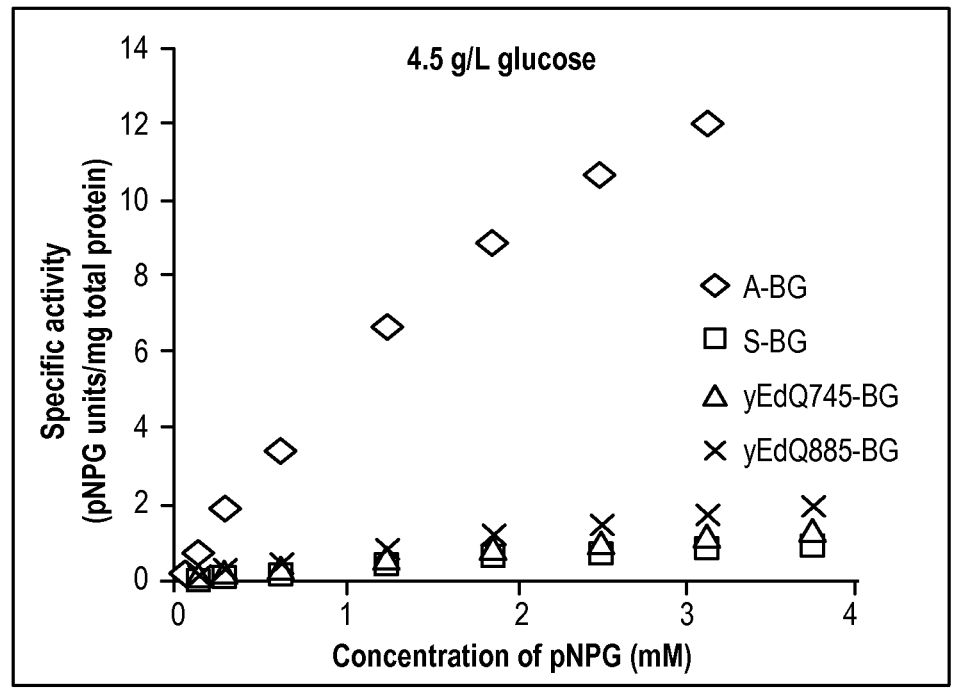
Figure 4E:
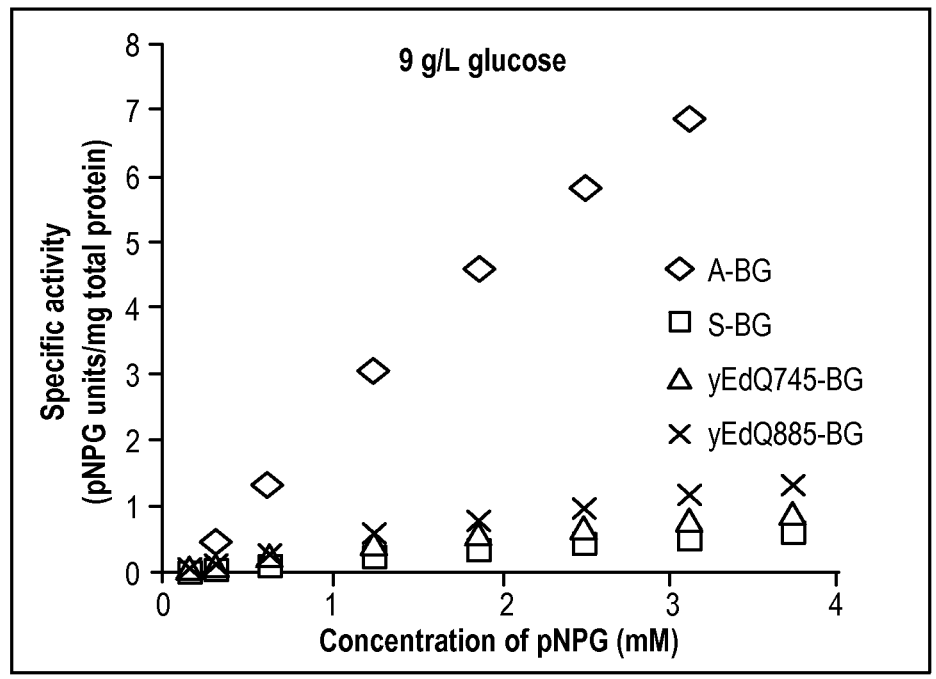
Figure 4F:
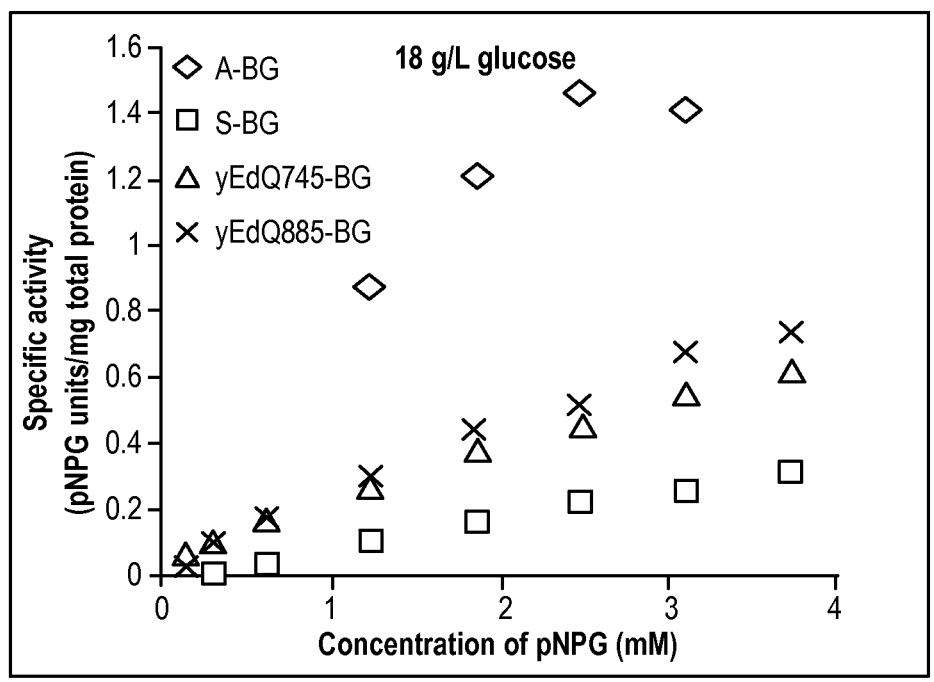
Figure 4G:
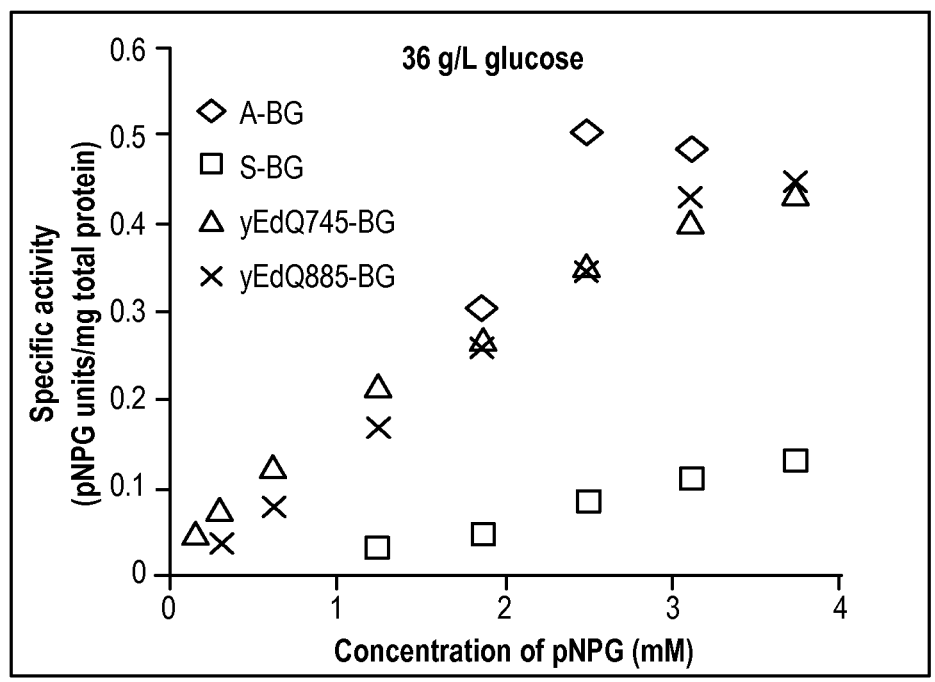

Average cellobiose catalyzed at 4, 8, 12, and 24 hours is shown in FIG. 1. Each of the BG mutants tested outperformed wild type BG at the 4-24 hr time points in cellobiose hydrolysis under the conditions tested in this assay. An ANOVA and Tukey-Kramer HSD analysis with an alpha of 0.05 was compiled for each of the time points. Only the 8 hr time point is shown in FIG. 2. Residual glucose and cellobiose are detectable in the Ctec2 and Trio enzyme cocktails. Thus, the raw data obtained from HPLC is corrected for this residual amount.

Each of the BG mutants had 30-60% increased cellobiose hydrolysis activity compared to wild type at 4-24 hrs under conditions tested.

The above example demonstrates that the improved beta-glucosidase enzymes described herein have increased catalytic activity compared to wild-type beta-glucosidase in the presence of glucose concentrations encountered in a typical corn mash fermentation reaction at early reaction times.

Example 4

This example shows that the improved beta-glucosidase enzymes described herein have improved kinetic properties compared to wild-type beta-glucosidase.

High resolution enzyme assays and kinetic testing comparing the beta-glucosidases described herein and commercial enzyme preparations were pursued to more clearly quantify differences in mutant BG enzymes compared to the wild type BG enzyme. Based on data presented herein, BG mutant YEdQ885 was selected for further analysis and compared to the BG activity present in commercial preparations of SP188 (Novozymes) and Accellerase® BG (DuPont) as well as wild type BG.

Comparison of BG kinetics between commercial enzymes and the improved beta-glucosidase enzymes are described herein.

The kinetic properties of beta glucosidase are important for cellulosic hydrolysis, since in commercial situations a wide range of substrate concentrations and different product inhibition conditions will be encountered. In this example, a Michaelis-Menten kinetics model was used to describe BG kinetics. Key kinetic parameters and the desired features are summarized in Table 1. To determine these kinetic properties, BG activity assays using standard substrates pNPG and cellobiose were employed. yEdQ745-BG (wild type) and yEdQ885-BG (improved), were compared with two commercial BGs, A-BG (Accellerase®) BG from Dupont) and S-BG (Novozymes SP188 from Sigma).

TABLE 1

Description of kinetic parameters and their desired features.

| Kinetic parameters | Description | Desired features |
|---|---|---|
| Vmax, units/mL or units/mg | Maximum velocity, the maximum velocity that an enzyme could achieve | High |
| Km, mM | Michaelis-Menten constant representing the substrate concentration at which half of the enzyme active sites in the sample are filled by substrate molecules in the steady state, a measure of substrate affinity | Low |
| Kcat, min$^{-1}$ | Turnover number, the maximum number of molecules of substrate that an enzyme can convert to product per catalytic site per unit of time | High |
| Ki, mM | Inhibition constant, the dissociation constant for inhibitor | High |
| Kcat/Km, min$^{-1}$ mM$^{-1}$ | Catalytic efficiency, a measurement of substrate specificity | High |
| Km/Ki | A measure of inhibitor influence | Low |

Kinetic Properties Determined Using pNPG Substrate Methods

BG activity assay using pNPG is one of the two commonly used standard assays to measure BG activity, which utilizes hydrolysis of p-nitrophenyl-β-D-glucopyranoside (pNPG) by BG into a yellow colored product, p-nitrophenol (pNP), that has a strong absorbance at 405 nm. One pNPG unit is defined as the amount of enzyme that produces 1 μmol of pNP per min. Briefly, to determine BG activity, 25 μL of diluted enzyme in 200 mM sodium acetate buffer (pH 5.0) was mixed with 25 μL of the same buffer and 25 μL of RO water (or glucose solution for the kinetic study) and the mixture was preincubated at 50° C. for 5 min. The reaction was initiated by adding 25 μL of 10 mM pNPG in 200 mM sodium acetate buffer (pH 5.0) and the mixture was incubated at 50° C. for 10 min. The reaction was then terminated by adding 100 μL of 0.25 M sodium carbonate, and the amount of pNP produced was determined by measuring absorbance at 405 nm using a predetermined calibration curve.

To determine kinetic properties using pNPG substrate, triplicate assays with pNPG concentrations ranging from 0.08 to 3.13 mM (for A-BG) or 0.16 to 3.75 mM (for all the other BGs) and glucose concentrations of 0, 0.5, 0.9, 4.5, 9, 18 and 36 g/L were performed. The range of substrate concentration was chosen to show detectable activity at the lowest concentration and saturation stage at high substrate concentration. The upper limit of inhibitor (glucose) level was chosen to get as close as possible to the real conditions during saccharification (~4% w/v glucose) and have a detectable residual activity.

To determine the kinetic properties, a competitive inhibition mechanism was hypothesized as proposed in the literature (Chauve et al, 2010; Krogh et al, 2010). The Michaelis-Menten equation with the competitive inhibition term can be expressed in Equation (1), where [S] is the substrate concentration (mM), [I] is the inhibitor concentration (mM), V is the rate of product formation (mM/min), Vmax is the maximal rate of product formation (mM/min), Km is the Michaelis-Menten constant and Ki is the inhibition constant. The turnover number, Kcat, can be calculated by Equation (2), where [Et] is the total amount of enzyme.

$$V = \frac{V_{max} \times [S]}{K_m\left(1 + \frac{[I]}{K_i}\right) + [S]} \quad (1)$$

$$K_{cat} = \frac{V_{max}}{[E_t]} \quad (2)$$

Conventionally, linearization methods can be used to determine the kinetic parameters based on Equation (1). Three common linear plots used are Lineweaver-Burke, Eadie-Hofstee and Hanes plots (Rogers and Gibon, 2009). However, these linearized versions of the Michaelis-Menten equation often produce substantial errors in parameter estimation. With the capability of accurate nonlinear modeling, JMP software was used to perform simultaneous nonlinear regression, which was shown to be a robust method (Kakkar et al, 1999). All of the activity data at different substrate levels and different inhibitor levels were fit simultaneously according to the full nonlinear equation for competitive enzyme inhibition as expressed in Equation (1). Thus, Vmax, Km and Ki can be determined simultaneously from this fitting process, and Km/Ki can then be calculated. Kcat can be obtained by Equation (2) and Kcat/Km can be calculated accordingly.

Results and Discussion

The complete kinetic profiles under various glucose inhibition conditions of the four BGs are presented in terms of relative activity (FIG. 3) and specific activity (pNPG units per mg of total protein) (FIG. 4) as a function of initial pNPG concentration. Specific activity is used due to the large concentration difference between the BGs described herein and commercial BGs. The relative activity was determined based on the maximum activity obtained in the absence of initial glucose inhibition. As shown in FIG. 3, the relative activity of A-BG decreased to less than that of the other three BGs when initial glucose concentration increased to 18 g/L. Under very high initial glucose concentration of 36 g/L, the maximum relative activity at high pNPG concentration was 1.5%, which was much less than that of the other three BGs, and the activity was completely lost at pNPG concentration below 1.875 mM. For a thorough comparison taking into consideration the differences in protein concentrations of the BG preparations, residual specific activity was also compared. As shown in FIG. 4, at initial glucose concentration of 9 g/L, A-BG lost activity completely at pNPG concentration of 0.08 mM. When the initial glucose concentration was further increased, A-BG lost activity completely at higher pNPG concentrations. However, the residual specific activity at pNPG concentration of 1.875 mM, 2.5 mM and 3.125 mM was still slightly higher than the other three BGs with initial glucose concentration of 36 g/L, the severest inhibitory condition tested.

For the other three more closely related BGs, yEdQ885-BG (modified) showed higher specific activity towards pNPG than both yEdQ745-BG (wild type) and S-BG under all conditions, except that at initial glucose concentrations of 36 g/L the yEdQ745 and yEdQ885BGs showed very similar specific activities. In the absence of initial glucose inhibition, S-BG showed slightly higher specific activity than yEdQ745-BG, while in the presence of initial glucose inhibition higher than 0.9 g/L, yEdQ745-BG showed higher specific activity than S-BG and the difference increased with increasing initial glucose concentration. On the other hand S-BG showed the lowest relative activity under all inhibitory conditions. yEdQ885-BG showed a higher relative activity than that of yEdQ745-BG under initial glucose concentration up to 4.5 g/L and a lower relative activity than that of yEdQ745-BG under initial glucose concentration higher than 9 g/L. Based on these results, the improved, engineered yEdQ885-BG and wild-type yEdQ745-BG have higher resistance to product (glucose) inhibition than S-BG.

The above experimental data were fit in the competitive inhibition model as expressed in Equation (1) by simultaneous nonlinear regression. All of the kinetic parameters determined through the modeling process are summarized in Table 2. The order of maximum velocity (Vmax) is A-BG>yEdQ885-BG>S-BG≈yEdQ745-BG. The order of Michaelis-Menten constant (Km) is A-BG<S-BG<yEdQ745-BG≈yEdQ885-BG, indicating that the commercial BGs have higher substrate affinity for pNPG than our two in-house BGs. Nevertheless, the in-house BGs have much higher dissociation constant for inhibitor (Ki), indicating higher tolerance to product inhibition. Consistent with Vmax, the order of turnover number (Kcat) is A-BG>yEdQ885-BG>S-BG≈yEdQ745-BG. With much lower Km and much higher Kcat, A-BG has a considerably higher catalytic efficiency (Kcat/Km) than the other enzymes. The catalytic efficiency of S-BG and yEdQ885-BG is quite close, which is higher than that of yEdQ745-BG. A-BG has the lowest inhibitor influence (Km/Ki) as well due to its low Km, and Km/Ki of yEdQ745-BG and yEdQ885-BG is quite close and lower than S-BG. To summarize the observations in this example, A-BG has better performance using the non-natural pNPG substrate among all four BGs tested based on all the kinetic parameters except Ki. However, it should be noted that the activity of A-BG was completely lost at low pNPG concentration (<1.875 mM) and high glucose inhibition concentration (36 g/L) that is commonly encountered in a commercial process using biomass.

TABLE 2

Kinetic parameters of BG determined using pNPG substrate

| pNPG substrate | Vmax (U/mg) | Km (mM) | Ki (mM) | Kcat (min$^{-1}$) | Kcat/Km (min$^{-1}$mM$^{-1}$) | Km/Ki |
|---|---|---|---|---|---|---|
| A-BG | 34.38 ± 0.67 | 0.099 ± 0.012 | 0.46 ± 0.05 | 2695.39 | 27226.18 | 0.22 |
| S-BG | 4.20 ± 0.14 | 0.42 ± 0.06 | 0.81 ± 0.11 | 504.00 | 1200.00 | 0.52 |
| yEdQ745-BG | 4.17 ± 0.11 | 0.64 ± 0.06 | 2.13 ± 0.18 | 500.40 | 781.88 | 0.30 |
| yEdQ885-BG | 6.33 ± 0.09 | 0.64 ± 0.03 | 2.19 ± 0.10 | 759.60 | 1186.88 | 0.29 |

Kinetic Properties Determined Using Natural Cellobiose Substrate

Methods

BG activity assay using cellobiose is the other standard assay to measure BG or cellobiase activity, which utilizes hydrolysis of cellobiose by cellobiase into two molecules of glucose, the last step of enzymatic hydrolysis of cellulose. One cellobiase unit (commonly termed as CBU) is defined as the amount of enzyme that converts 1 mol of cellobiose or produces 2 μmol of glucose per min. Briefly, to determine BG activity, 25 μL of diluted enzyme in 50 mM citrate buffer (pH 4.8) equilibrated to 50° C. was mixed with 25 μL cellobiose (or cellobiose/glucose mixture for the kinetic study) to start the reaction. The mixture was incubated at 50° C. for 10 min, and the reaction was terminated by incubating the mixture at 99° C. for 5 min. Different methods are available to measure the glucose produced in the assays. For the kinetic study, HPLC was used.

To determine kinetic properties using cellobiose substrate, duplicate assays with cellobiose concentrations ranging from 0.47 to 15 mM and glucose concentrations of 0, 0.9, 4.5, 6.75, and 8.1 (for A-BG) or 9 (for all the other three BGs) g/L were performed. As for pNPG substrate, the range of cellobiose substrate concentration was chosen to show detectable activity at the lowest substrate concentration and saturation stage at high substrate concentration. However, in contrast to the pNPG substrate, when there was still some activity left at glucose concentration up to 36 g/L, most of the BG activity was lost at an inhibitor level of 9 g/L when cellobiose substrate was used. The activity was completely lost for A-BG at this inhibitor level, which is why 8.1 g/L of glucose condition was included for A-BG. It should also be noted that colorimetric glucose assay cannot provide activity results for inhibitory glucose levels above 0.9 g/L after several trials. Therefore, HPLC measurements were used for kinetic studies using cellobiose substrate. It should be pointed out that the HPLC method may not be sensitive enough either to capture BG activity under more severe glucose inhibition conditions than 9 g/L of glucose. Moreover, theoretically there are two ways to measure BG activity by HPLC when cellobiose is used as the substrate: tracking consumption of cellobiose or tracking production of glucose. However, as shown by the example of one set of results from S-BG in Table 3, tracking glucose is problematic due to measurement sensitivity. In Table 3, Δ% is defined as follows and is an indicator of measurement sensitivity, since the difference of substrate or product concentrations before and after reaction was used to determine BG activity.

$$\Delta\% = (\text{start conc. of cellobiose} - \text{end conc. of cellobiose})/\text{start conc. of cellobiose} \times 100\% \quad (3)$$

$$\Delta\% = (\text{end conc. of glucose} - \text{start conc. of glucose})/\text{start conc. of glucose} \times 100\% \quad (4)$$

With increasing inhibitor (glucose) level, Δ% is decreasing. For the case of tracking glucose, Δ% was too small to be reliable when 4.5 g/L of glucose was added at the beginning. A similar trend was observed for all the other BGs. Thus, the approach of tracking cellobiose was chosen due to its higher detection sensitivity. In the substrate range used to determine kinetic parameters (0.47 to 30 mM for A-BG and 0.47 to 15 mM for the other three BGs), the detection sensitivity is reasonable.

TABLE 3

Detection sensitivity exemplified by a set of data obtained for S-BG by HPLC.

| | Tracking Cellobiose Δ% | | | | | Tracking Glucose Δ% | | |
|---|---|---|---|---|---|---|---|---|
| Cellobiose mM | 0 g/L Glucose | 0.9 g/L Glucose | 4.5 g/L Glucose | 6.75 g/L Glucose | 9 g/L Glucose | 0 g/L Glucose | 0.9 g/L Glucose | 4.5 g/L Glucose |
| 60.00 | 0.86 | 0.73 | 0.19 | −5.23 | 1.42 | NA | 18.63 | 3.85 |
| 30.00 | 1.64 | 3.60 | 2.08 | 1.31 | 0.28 | NA | 24.32 | 3.10 |
| 15.00 | 4.60 | 5.98 | 3.26 | 2.22 | 1.16 | NA | 24.26 | 1.80 |
| 7.50 | 9.04 | 8.84 | 4.73 | 2.30 | 1.46 | NA | 21.24 | 0.57 |
| 3.75 | 16.80 | 13.90 | 5.42 | 2.58 | 2.06 | NA | 14.31 | −0.08 |
| 1.88 | 25.32 | 17.40 | 6.42 | 2.81 | 2.33 | NA | 8.49 | −0.65 |
| 0.94 | 34.82 | 20.77 | 6.38 | 3.34 | 3.44 | NA | 3.09 | −0.24 |
| 0.47 | 44.56 | 21.75 | 7.49 | 3.13 | 2.99 | NA | 3.37 | 0.25 |

A similar simultaneous nonlinear regression method based on the competitive inhibition equation expressed in Equation (1) was used to determine kinetic parameters of BG towards cellobiose.

Results and Discussion

The specific activity used here was determined by the initial velocity approach that is required by implementing Michaelis-Menten model (Copeland, 2000). The specific activity was determined by measuring consumption of cellobiose in the first 10 min of reaction and was expressed as $\mu mol\ min^{-1}\ mg^{-1}$, where $mg^{-1}$ means per mg of total protein. The relative activity was determined based on the maximum activity obtained in the absence of initial glucose inhibition.

To compare performance of the four BGs more clearly, activity data as a function of initial cellobiose concentration of all four BGs are compiled together for each glucose inhibition condition and presented as relative activity in FIG. 5 and specific activity in FIG. 6.

Figure 5A:
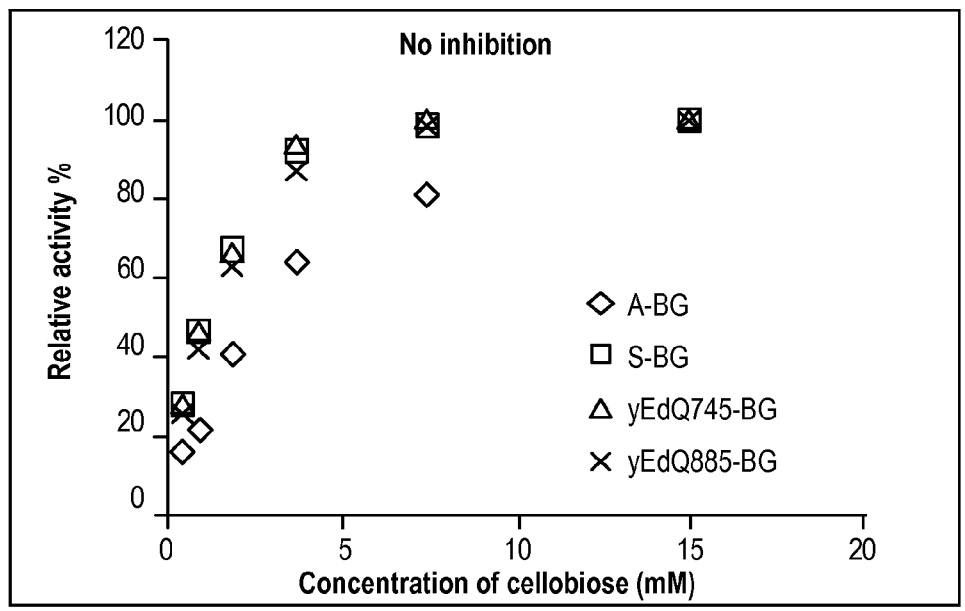
FIG. 5 shows a comparison of relative activity of different beta-glucosidase enzymes using cellobiose as a substrate under various glucose inhibition conditions. (a) No inhibition; (b) 0.9 g/L glucose; (c) 4.5 g/L glucose; (d) 6.75 g/L glucose; (e) 9 g/L glucose condition.
Figure 5B:
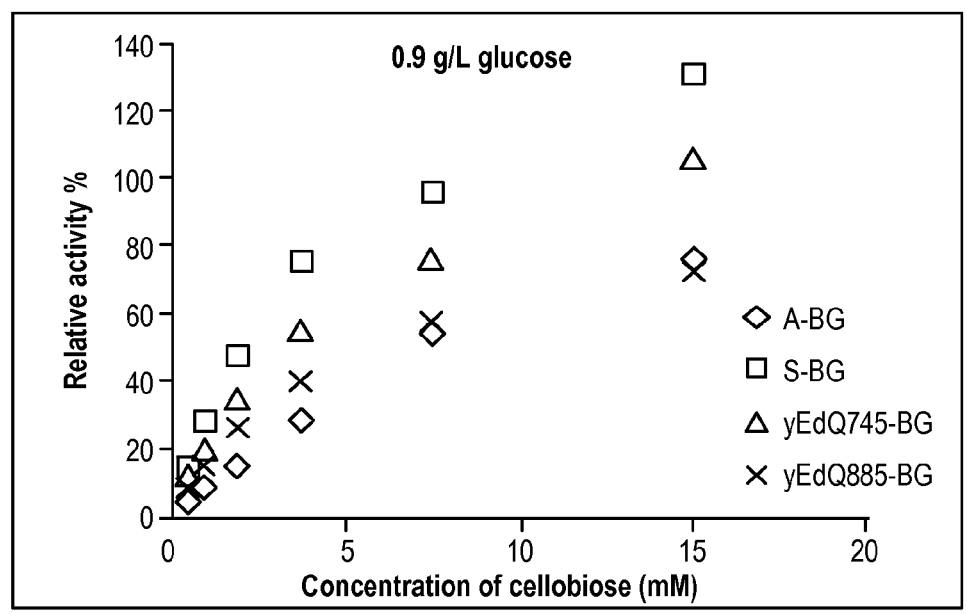
Figure 5C:
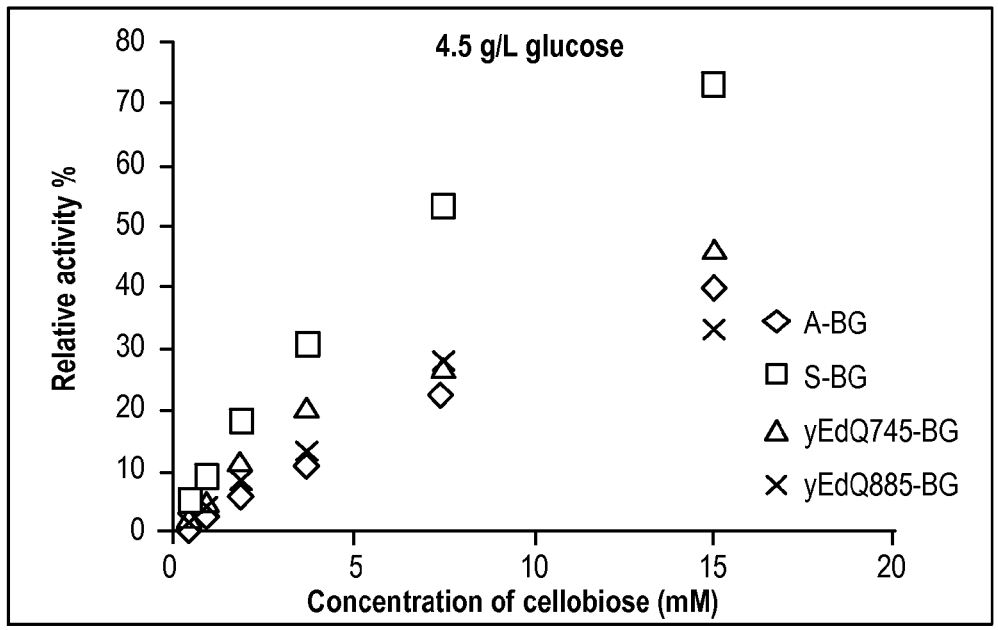
Figure 5D:
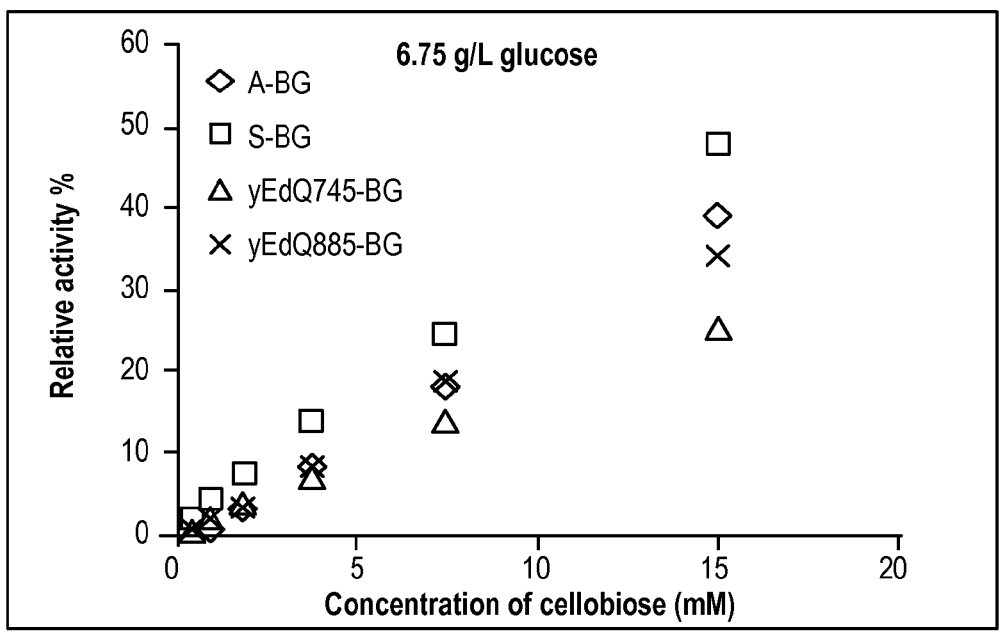
Figure 5E:
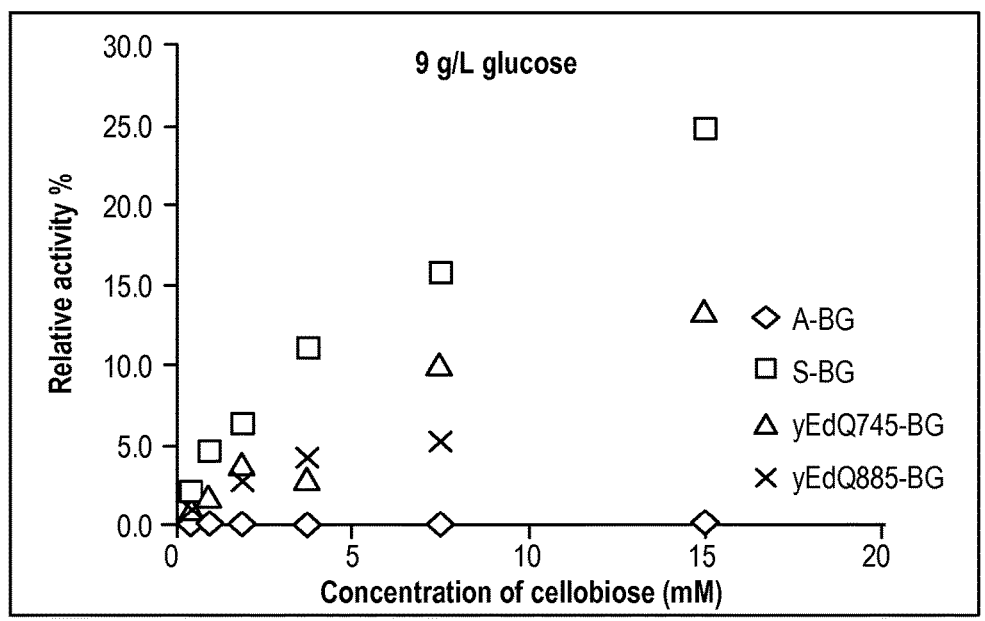
Figure 6A:
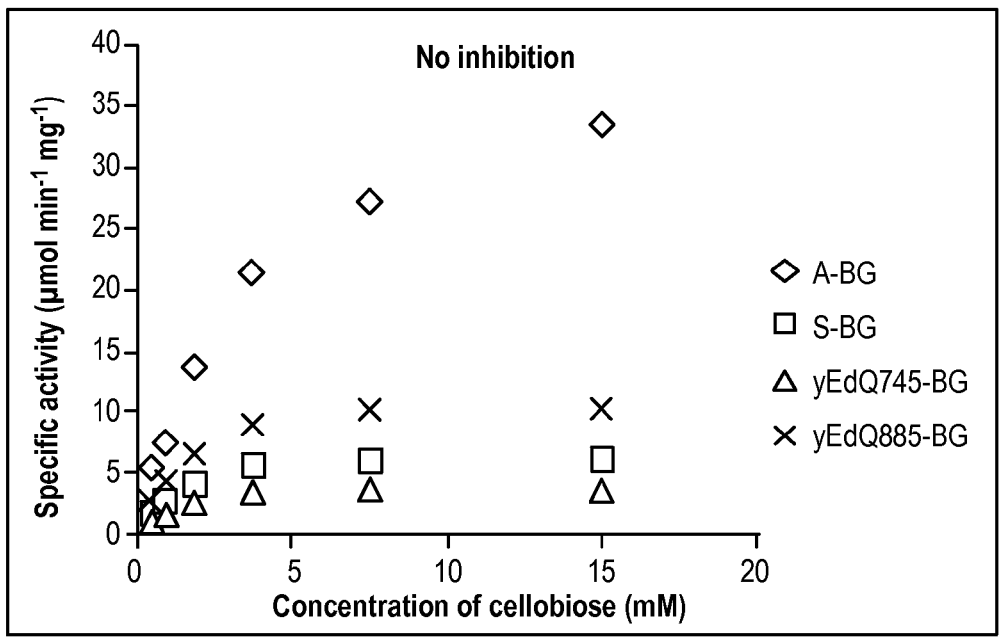
FIG. 6 shows a comparison of specific activity of different beta-glucosidase enzymes using cellobiose as a substrate under various glucose inhibition conditions. (a) No inhibition; (b) 0.9 g/L glucose; (c) 4.5 g/L glucose; (d) 6.75 g/L glucose; (e) 9 g/L glucose condition.
Figure 6B:
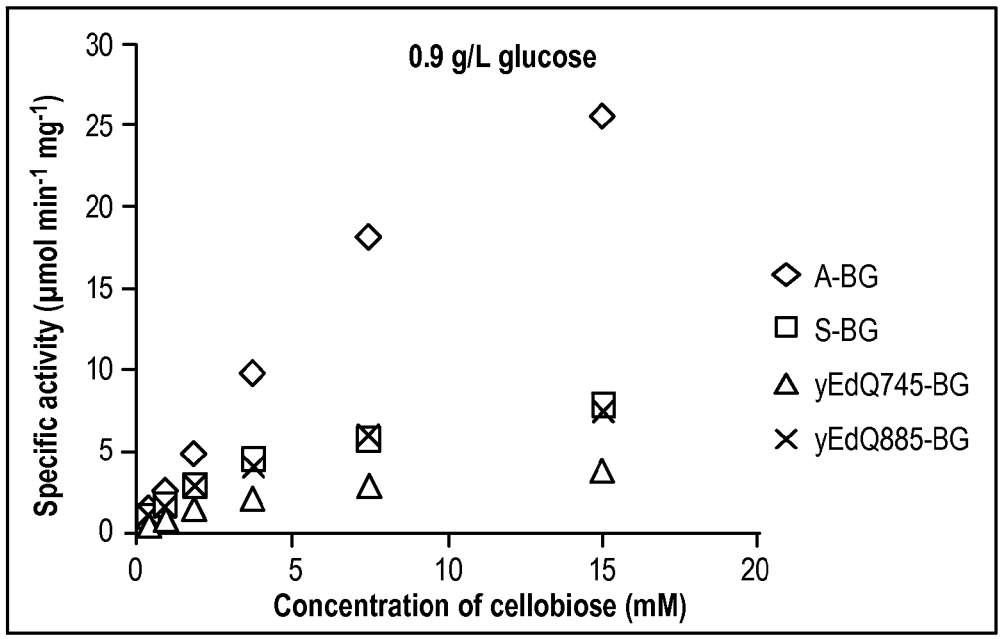
Figure 6C:
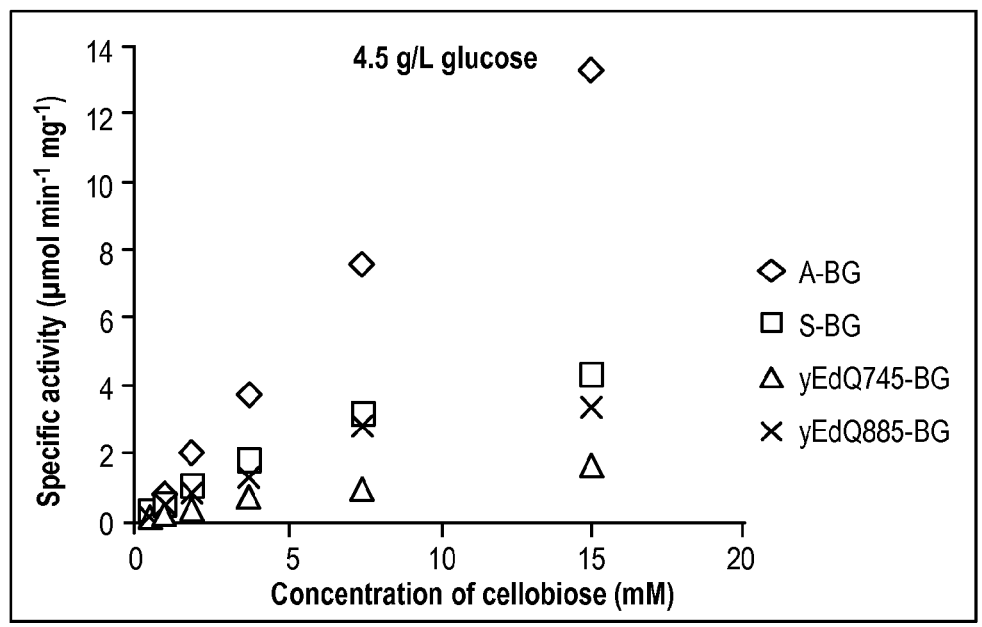
Figure 6D:
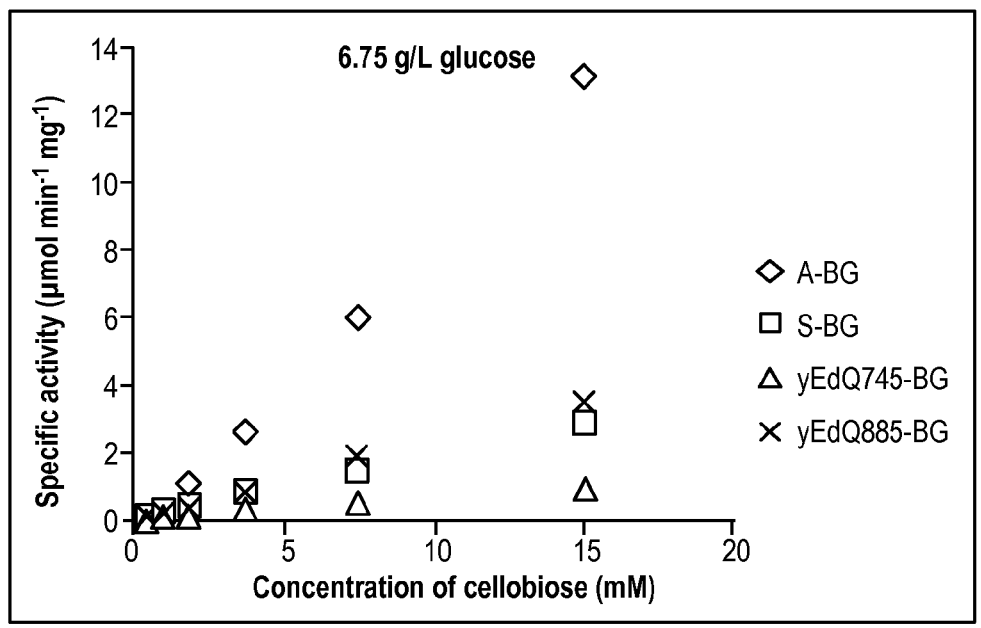
Figure 6E:
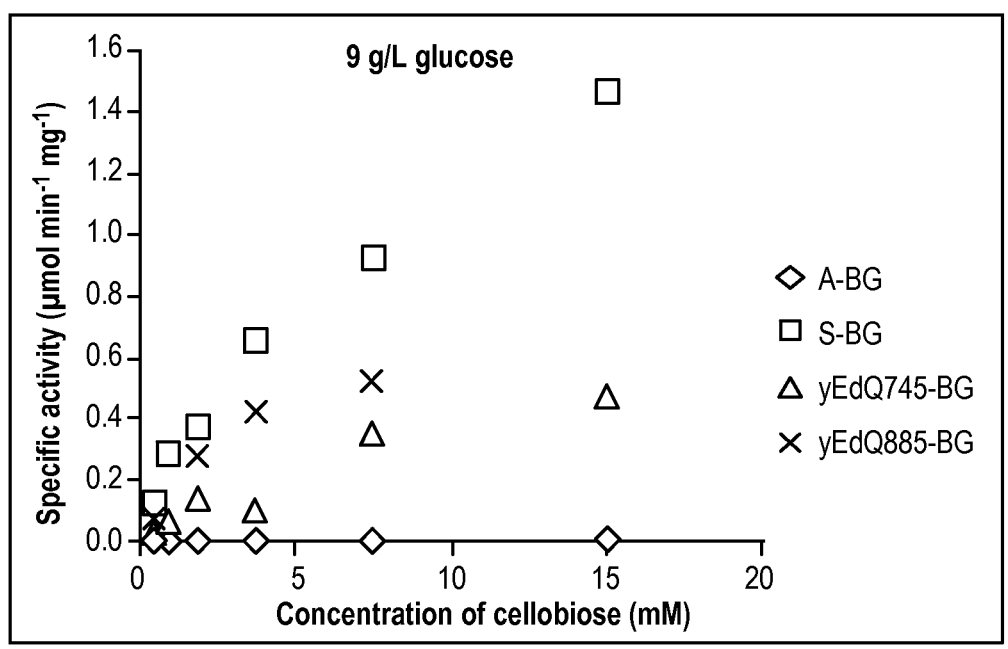
Figure 7A:
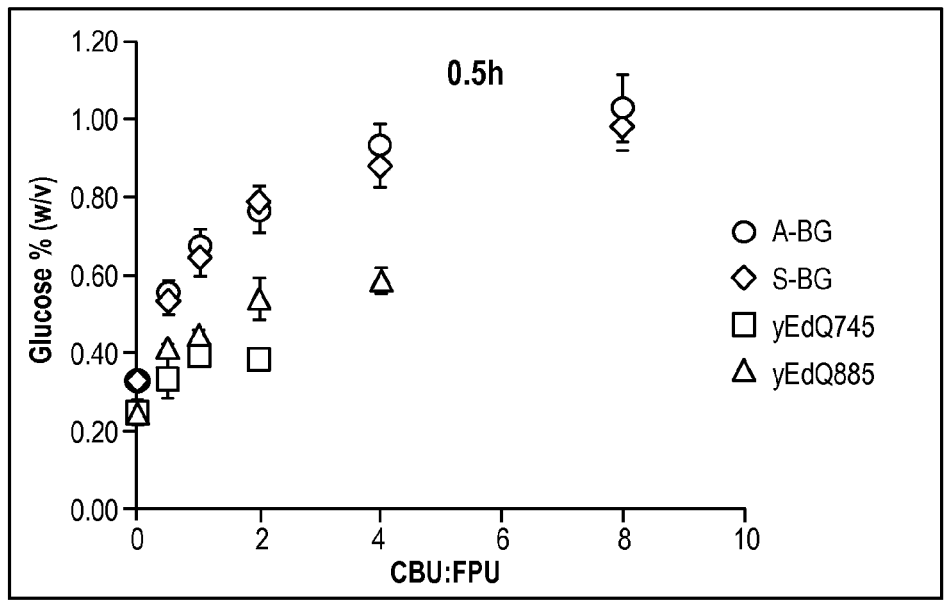
FIG. 7 shows glucose release from cellulose substrate when cellulase mixture was supplemented with different BG doses of A-BG, S-BG, yEdQ745-BG and yEdQ885-BG. (a) 0.5 h; (b) 1 h; (c) 2 h; (d) 3 h; (e) 6 h; (f) 24 h; (g) 48 h.
Figure 7B:
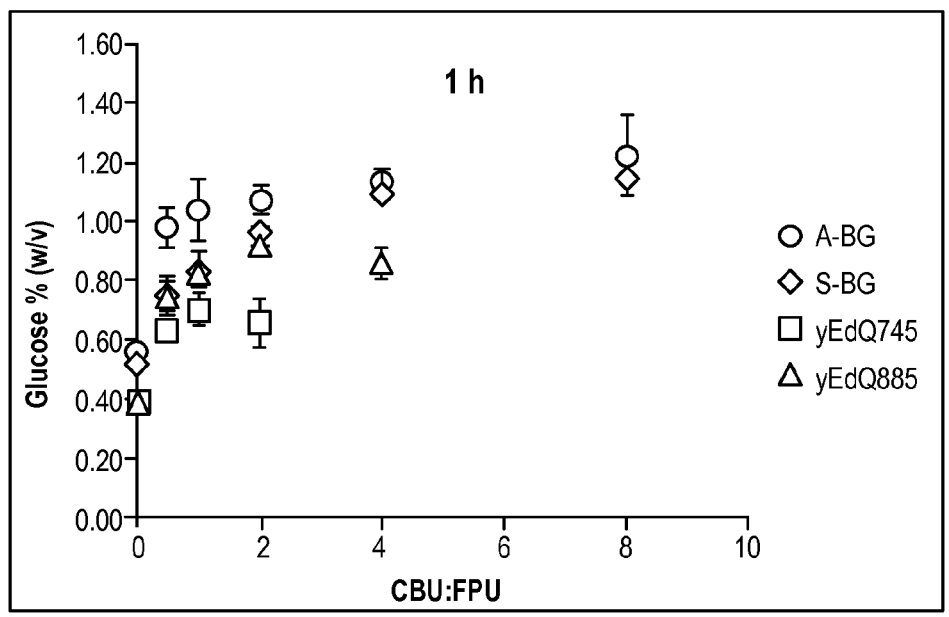
Figure 7C:
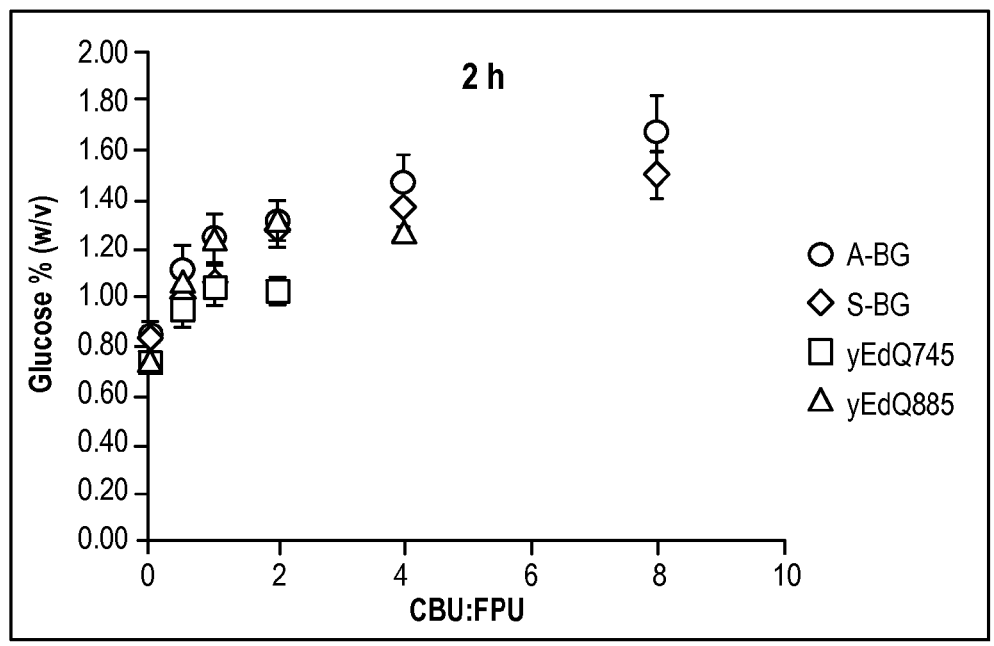
Figure 7D:
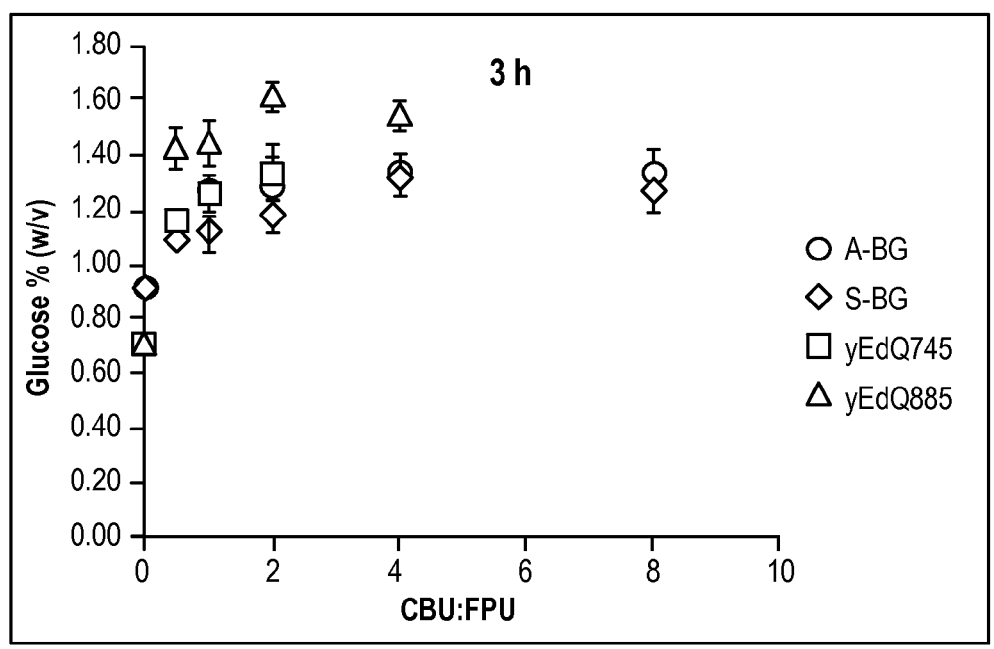
Figure 7E:
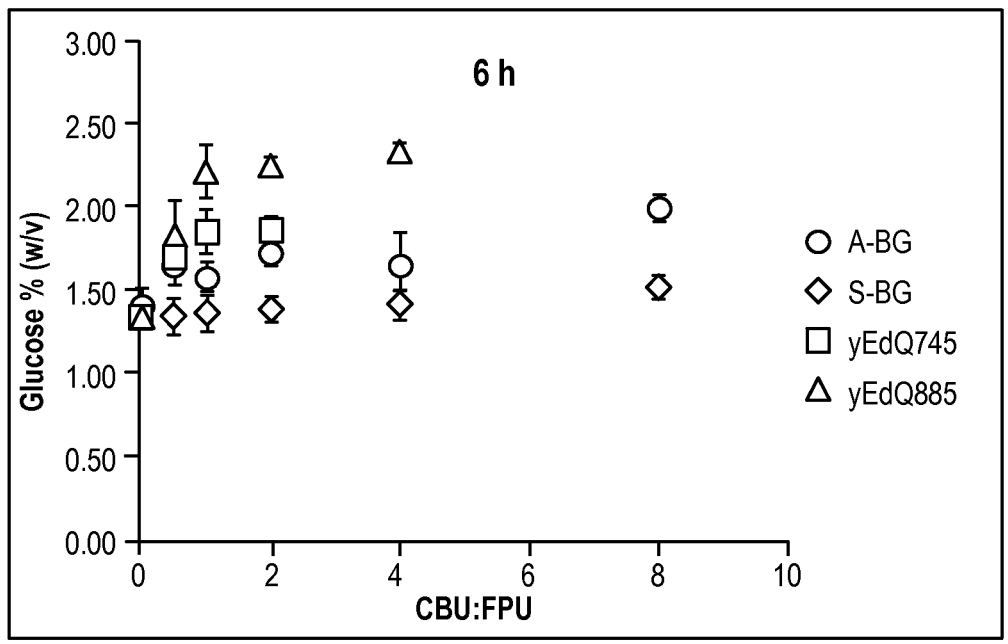
Figure 7F:
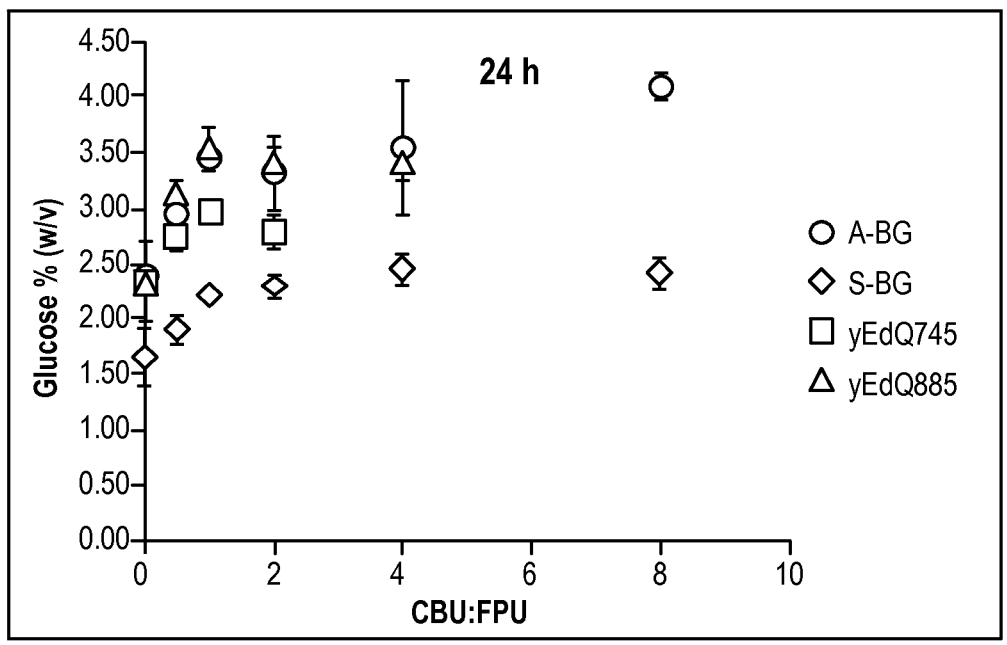
Figure 7G:
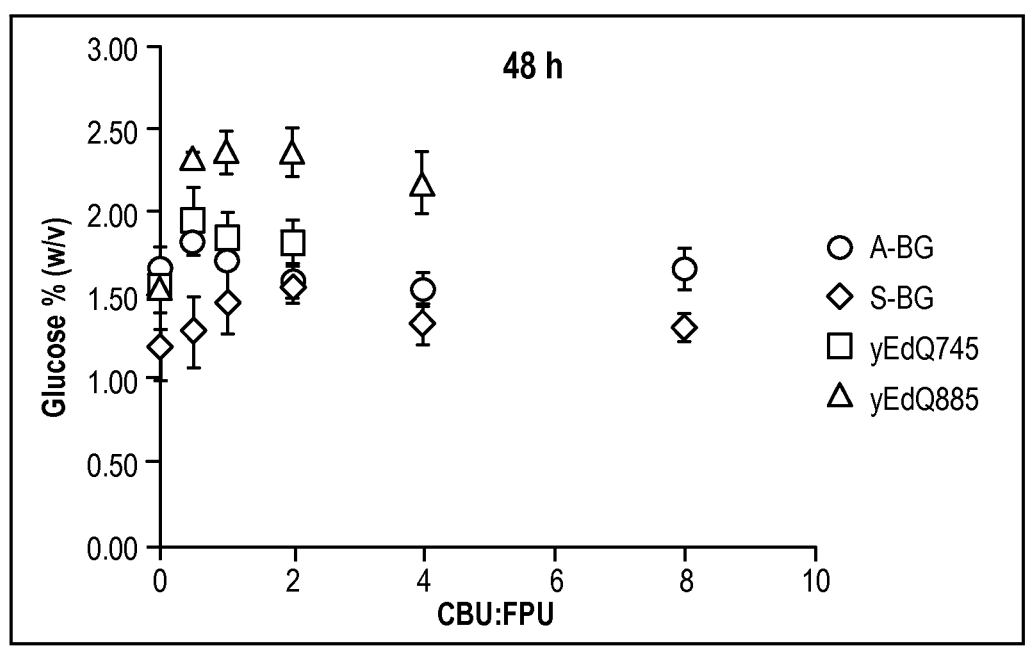

As shown in FIG. 6, A-BG has a much higher specific activity towards cellobiose than that of all the other BGs with glucose inhibition up to 8.1 g/L (Although the condition of 8.1 g/L of glucose was not tested on the other three BGs, specific activity of the other three BGs under 6.75 g/L of glucose was less than that of A-BG under 8.1 g/L of glucose (data not shown)). However, as shown in FIGS. 5(e) and 6(e), A-BG completely lost its activity towards cellobiose under initial glucose concentration of 9 g/L (0.9% w/v). FIG. 5 has shown that relative activity of A-BG was below all the other three BGs under all substrate concentrations in the absence of glucose inhibition and in the presence of glucose inhibition up to 4.5 g/L glucose except one data point (15 mM of cellobiose, 4.5 g/L glucose). For the condition of 6.75 g/L glucose inhibition, the relative activity of A-BG was lower than that of S-BG, close to that of yEdQ885-BG and slightly higher than that of yEdQ745-BG. As stated above, A-BG completely lost its activity towards cellobiose under initial glucose concentration of 9 g/L (0.9% w/v).

As shown in FIG. 6, for the other three more closely related BGs, yEdQ885-BG (modified) showed higher specific activity towards cellobiose than both yEdQ745-BG (wild type) and S-BG in the absence of glucose inhibition. However, in the presence of glucose inhibition, S-BG has shown a closer activity level to yEdQ885-BG when the initial glucose concentration was up to 6.75 g/L and a significantly higher activity than yEdQ885-BG under the maximum initial glucose concentration tested (9 g/L). The specific activity of yEdQ745-BG was the lowest under all conditions tested. On the other hand, in terms of relative activity, all three BGs showed a very similar profile (FIG. 5(a)) in the absence of glucose inhibition, and S-BG retained the highest relative activity under all the inhibitory conditions among the three BGs. yEdQ745-BG showed a higher relative activity than yEdQ885-BG under all inhibitory conditions except for using an initial glucose concentration of 6.75 g/L.

The above experimental data were fit in the competitive inhibition model as expressed in Equation (1) by simultaneous nonlinear regression. The results indicate the competitive inhibition model is sufficient for the BGs tested, although more complex models were also suggested in literature (Calsavara et al, 1999).

All of the kinetic parameters determined through the modeling process are summarized in Table 4. Consistent with the specific activity data, the order of maximum velocity (Vmax) is A-BG>yEdQ885-BG>S-BG>yEdQ745-BG. S-BG and the two in-house BGs have close Michaelis-Menten constant (Km) that is less than that of A-BG, indicating higher substrate affinity for cellobiose. It should be noted here that the high Km of A-BG could also be resulted from very high turnover number (Kcat) (see, Y. H. Percival Zhang, et al., In *Biofuels: Methods and Protocols, Methods in Molecular Biology* edited by Jonathan R. Mlelenz. 2009, 581, 213-231). The order of inhibition constant (Ki) is A-SG>S-BG>yEdQ745-BG>yEdQ885-BG, suggesting the order of tolerance to product inhibition. Consistent with Vmax, the order of turnover number (Kcat) is A-BG>yEdQ885-BG>S-BG>yEdQ745-BG. Due to the relatively high Kcat and low Km, yEdQ885-BG showed significantly higher catalytic efficiency (Kcat/Km) than the other three BGs tested (A-BG>S-BG>yEdQ745-BG). In term of the inhibitor influence (Km/Ki), S-BG has the best performance with Km/Ki much less than the other three BGs. Km/Ki of yEdQ745-BG is less than that of A-BG and yEdQ885-BG, which have very close Km/Ki.

The above example demonstrates that the modified beta-glucosidase enzymes described herein have improved kinetic properties compared to wild-type beta-glucosidase and commercial enzymes on cellobiose substrate. This in part results from the relatively high Kcat and low Km of yEdQ885-BG compared to the wild-type and commercial preparations such that yEdQ885 shows significantly higher catalytic efficiency (Kcat/Km) than the other three BGs tested (A-BG>S-BG>yEdQ745-BG). Also, compared to commercial preparations, the BGs described herein have shown higher tolerance to product inhibition when using pNPG as the substrate, and between these two BGs, yEdQ885 has a higher catalytic efficiency than the wild type due to higher Kcat.

Example 5

This example shows that the modified beta-glucosidase enzymes described herein increase glucose release during saccharification when a commercial enzyme preparation is supplemented with various doses of beta-glucosidase.

Effects of BG Supplementation on Filter Paper Substrate yEdQ745-BG (WT control), yEdQ885-BG, A-BG and S-BG were further tested on filter paper substrate by supplementing BG to Celluclast, an early generation cellulase product from Novozymes that does not contain a significant amount of BG activity, in a 48-hour saccharification process. Experimental conditions in this example using filter paper substrate was 10% solid loading and 20% Celluclast loading based on glucan content. Different BG dosage based on CBU:FPU (BG activity/total cellulase activity) was tested. Representative results are shown in FIG. 7.

To compare the BG performance, glucose release at different BG doses using various BGs was compared at different time points in FIG. 7. Within the first 1 h, samples using the two commercial BGs had higher glucose release. At 2 h, glucose release of samples using in-house BGs was closer to that of the samples using commercial BGs. At later stages of saccharification, glucose release of samples using in-house BGs was higher than that of the samples using commercial BGs in an order of yEdQ885-BG>yEdQ745-BG>A-BG>S-BG. The only exception is for the 24 h data, where glucose release of the samples using A-BG was higher. The optimal BG dosage was also determined based on the results shown in FIG. 7. The optimal CBU/FPU ratio was 8, 4, 1 and 2 for A-BG, S-BG, yEdQ745-BG and yEdQ885-BG, respectively.

Figure 8A:
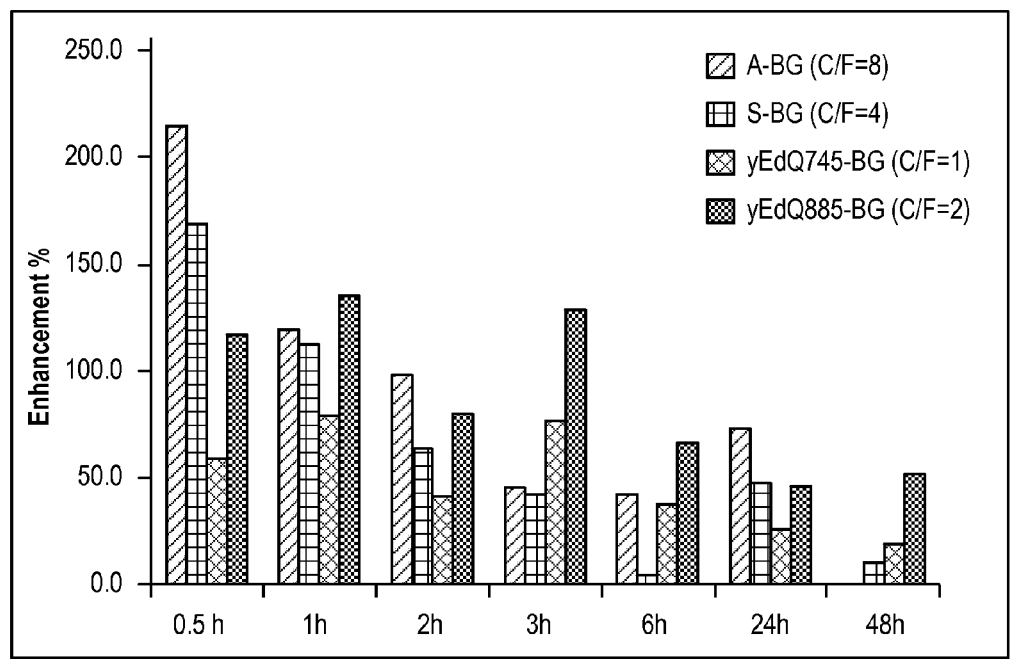
FIG. 8 shows performance comparison of different BGs. (a) Enhancement of glucose release; (b) Lift of glucan conversion.

Enhancement of glucose release (Equation 5) and lift of sugar conversion (Equation 6) was compared among various BGs at the optimal dosage over time in FIG. 8.

TABLE 4

Kinetic parameters of BG determined using cellobiose substrate

| Cellobiose substrate | Vmax (units/mg) | Km (mM) | Ki (mM) | Kcat (min$^{-1}$) | Kcat/Km (min$^{-1}$mM$^{-1}$) | Km/Ki |
|---|---|---|---|---|---|---|
| A-BG | 51.89 ± 2.53 | 6.56 ± 0.89 | 5.20 ± 0.63 | 4068.18 | 620.15 | 1.26 |
| S-BG | 7.77 ± 0.56 | 1.59 ± 0.41 | 3.13 ± 0.76 | 932.40 | 586.42 | 0.51 |
| yEdQ745-BG | 4.36 ± 0.24 | 1.45 ± 0.29 | 1.56 ± 0.29 | 523.20 | 360.83 | 0.93 |
| yEdQ885-BG | 11.57 ± 0.59 | 1.45 ± 0.26 | 1.11 ± 0.19 | 1388.40 | 957.52 | 1.31 |

$$\text{Enhancement \%} = \frac{\text{Glucose released with } BG - \text{Glucose released without } BG}{\text{Glucose released without } BG} \times 100\% \quad (5)$$

$$\text{Lift of conversion \%} = \quad (6)$$
$$\text{glucan conversion with } BG \% - \text{glucan conversion without } BG \%$$

Figure 8B:
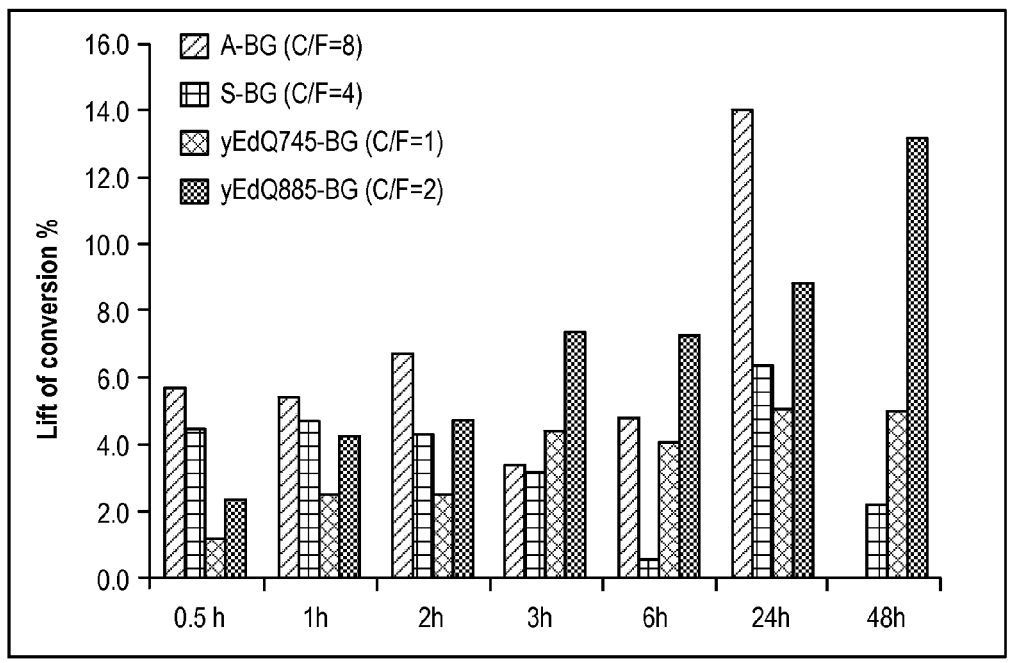

The enhancement effect of BG supplementation on saccharification was very significant for all the BGs tested, especially in the early stage. As shown in FIG. 8, at the optimal BG level, between the two commercial BGs, A-BG supplementation resulted in higher enhancement of glucose release at every time point during the first 24 h. Except the 3 h and 6 h data, enhancement of glucose release by adding yEdQ745-BG was less than that by adding commercial enzymes up to 24 h. At 48 h, there was no enhancement of glucose release by supplementing A-BG, and less enhancement by supplementing S-BG than yEdQ745-BG. Supplementation of yEdQ885-BG resulted in significantly higher enhancement of glucose release than yEdQ745-BG at all the time points and significantly higher enhancement of glucose release than commercial BGs at 3 h, 6 h and 48 h. Lift of conversion was compared between various BGs at the optimal dosage over time in FIG. 8(b). The trend of lift of conversion was consistent with the enhancement of glucose release. It should be noted that the enhancement of sugar release was more than 50% and the lift of sugar conversion was more than 13% up to 48 h by supplementing the modified in-house BG, yEdQ885-BG. yEdQ885-BG outperformed the other three BGs, likely due to the higher catalytic efficiency (Kcat/Km) among the four BGs.

This example shows that both wild type and improved BG enhanced saccharification when supplemented to a commercial cellulosic enzyme cocktail. The modified BG, yEdQ885-BG, had a stronger effect than all the other BGs. Higher BG dosage, i.e. higher CBU:FPU, tended to result in higher enhancement until reaching a plateau. The optimal CBU:FPU was 8, 4, 1 and 2 for A-BG, S-BG, yEdQ745-BG and yEdQ885-BG, respectively.

The above example demonstrates that the modified beta-glucosidase enzymes described herein improve saccharification efficiency using a cellulosic substrate.

Example 6

This example shows that supplementing commercial enzyme preparations with beta-glucosidase increased the saccharification rate of cellulosic biomass (corn stover).

Testing the Role of BG in Combination of C/Htec and GT TRIO.

To further demonstrate the importance of supplementing BG into the saccharification process, different commercial preparations of BG were tested to determine the ability to increase the saccharification efficiency; and to reduce the cost for the saccharification. In this experiment, 10% CTecII per gram glucan and 0.5% HtecII per mass solids was used as a control level for high saccharification of pretreated biomass. The relatively low enzyme dose of 3% Genencor® Trio per gram glucan was used as a base enzyme level to observe increases in saccharification from supplementation with BG enzymes. Enzyme doses of 0.5%, 1% and 2% of HtecII were used in a parallel set of reactions to likewise observe increases in saccharification from supplementation with concentrated extract from yEdQ745, yeast expressing wild type BG and another set of samples supplemented with commercial BG.

BG were used from two sources: wild type BG (yEdQ745) and commercial BG (Nozyme product SP-188).

Commercial cellulase preparations: Novozymes CtecII, Novozymes HtecII and Genencor® Trio.

Biomass used for the experiment: For each reaction 3 gms from Run 177 corn stover at 10% final solid concentration.

BG addition: 2 mL of wild type BG concentrated from yEdQ745 (11× concentrated) was added to the respective reaction.

Commercial BG: 1 uL/gm of biomass

Buffer: sodium citrate buffer pH5.0 was used for the reaction

Saccharification temperature: 50° C./24 and 48 hours.

Figure 9:
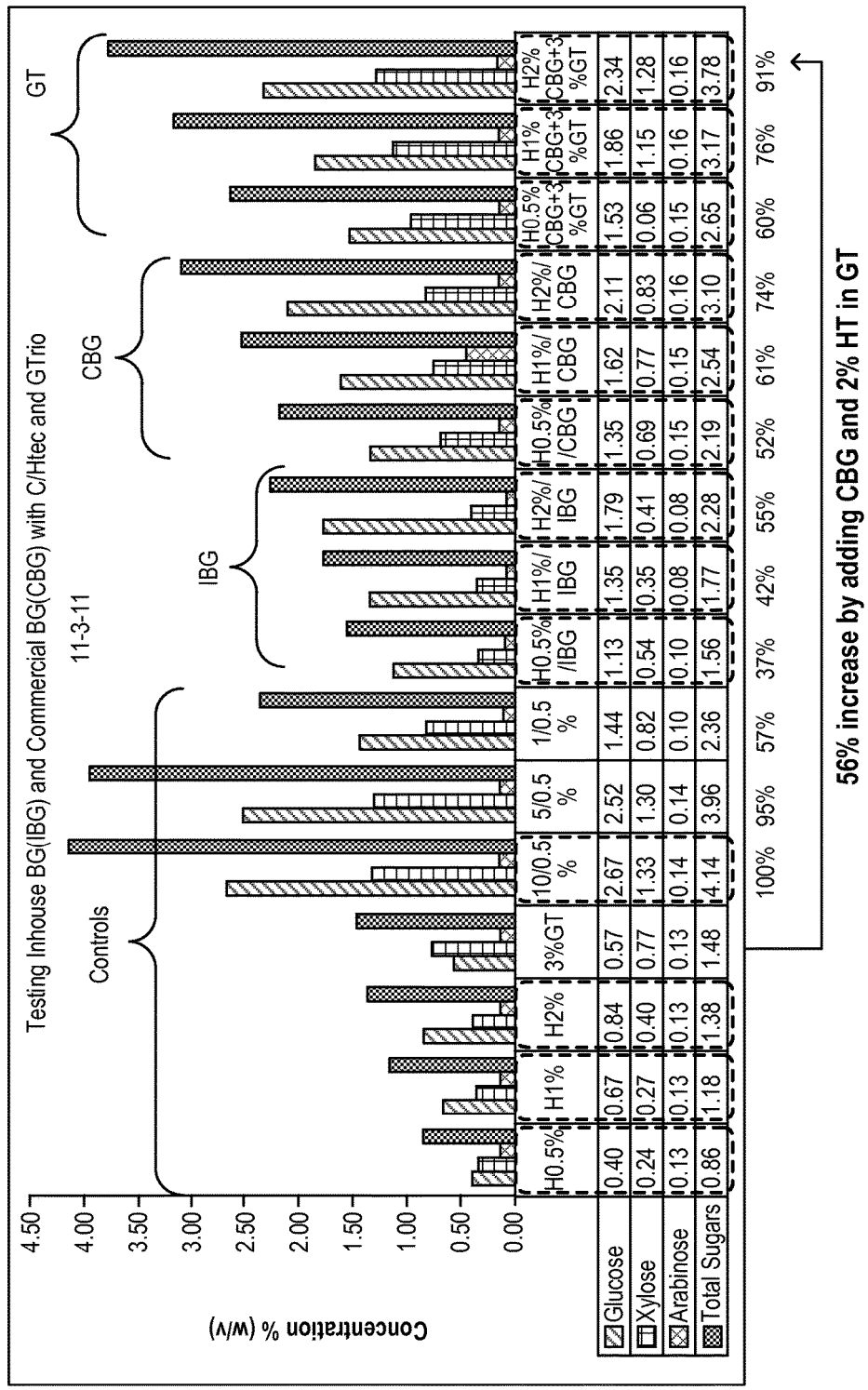
FIG. 9 shows augmentation of activities of HTecII by BG addition. Addition of Novozymes commercial cellulase cocktail to pretreated biomass (10% CTecII loading/gram glucan and 0.5% HTecII loading/mass solids) is considered as 100%. The glucose concentrations detected in the reactions were compared to the CtecII/HtecII enzyme dose of 10%/gram glucan/0.5%/mass solids, respectively. CtecII and Genencor® Trio were added on the basis of glucan value in the biomass; Htec II was added on the basis of solid %. Abbreviations in the figure: H0.5%: addition of HtecII 0.5%; H1%: addition of HtecII 1%; H2%: addition of HtecII 2%; 3% GT: addition of 3% Genencor® Trio; 10/0.5%, 5/0.5%, 1/0.5%: addition of 10%, 5% and 1% CtecII in combination with 0.5% HtecII; IBG: in-house BG; CBG: commercial BG (Novozymes SP-188); H0.5% CBG+3% GT, H1% CBG+ 3% GT, H2% CBG+3% GT: addition of 0.5%, 1% and 2% of HtecII in combination with commercial BG and 3% Genencor® Trio.

Results:

Supplementation of concentrated yeast supernatant from yEdQ745 containing wild type BG to the commercial preps increased saccharification efficiency. Compared to the activity of HtecII alone, BG addition showed significantly higher glucose release activity, suggesting the combination of cellobiose producing enzymes and cellobiose hydrolyzing enzymes are needed to increase overall glucose production. As shown in FIG. 9, 0.4% (w/v) glucose release (at 0.5% HtecII dosing) was dramatically increased with the addition of wild type BG from yEdQ745. Likewise, supplementation with commercial BG also increased glucan to glucose conversion.

This example shows that BG is an important enzyme for biomass saccharification, and that when supplemented into commercial cellulosic enzyme preparations can significantly increase saccharification efficiency. This example also shows that supplementation of lower concentrations of commercial enzyme preparations with BG can provide equal or greater sugar release, thereby providing an effective platform for enzyme cost reduction.

REFERENCES

1. Dongyang Liu, Ruifu Zhang, Xingming Yang, Zhenhua Zhang, Song Song, Youzhi Miao and Qirong Shen. Characterization of a thermostable β-glucosidase from *Aspergillus fumigatus* Z5, and its functional expression in *Pichia pastoris* X33. *Microbial Cell Factories* 2012, 11:25.
2. Neil J. Parry, David E. Beever, Emyr Owen, Isabel Vandenberghe, Jozef Van Beeumen Œ and Mahalingeshwara K. Bhat. Biochemical characterization and mechanism of action of a thermostable β-glucosidase purified from *Thermoascus aurantiacus*. *Biochemical Journal* 2001, 353, 117-127.
3. Marie Chauve, Hugues Mathis, Delphine Huc, Dominique Casanave, Frédéric Monot, Nicolas Lopes Ferreira. Comparative kinetic analysis of two fungal β-glucosidases. *Biotechnology for Biofuels* 2010, 3:3.
4. Y. H. Percival Zhang, Jiong Hong, and Xinhao Ye. Cellulase assays. In *Biofuels: Methods and Protocols, Methods in Molecular Biology* edited by Jonathan R. Mlelenz. 2009, 581, 213-231.
5. Alistair Rogers and Yves Gibon. Enzyme kinetics: theory and practice. In *Plant Metabolic Networks* edited by J. Schwender. 2009, 71-103.
6. Tarundeep Kakkar, Harold Boxenbaum and Michael Mayersohn. Estimation of $K_1$ in a competitive enzyme-inhibition model: comparisons among three methods of data analysis. *Drug Metabolism and Disposition* 1999, 27, 756-762.

7. Dan Siegel, Ira Marton, Mara Dekel, Ben-Ami Bravdo, Shouming He, Stephen Withers, Oded Shoseyov. Cloning, Expression, Characterization, and Nucleophile identification of Family 3, *Aspergillus niger* beta-glucosidase. J. Biol. Chem 2000 p. 4973-4980.
8. Annette Sorenson, Peter Stephensen Lubeck, Mette Lubeck, Philipp Teiler, Birgitte Ahring. Beta-glucosidases from a new *Aspergillus* species can substitute commercial beta-glucosidases for saccharification of lignocellulosic biomass. 2011 Canadian J. Microbiol. 57 p. 638-650.
9. Kristian B. R. M. Krogh, Paul V. Harris, Carsten L. Olsen, Katja S. Johansen, Jesper Hojer-Pedersen, Johan Borjesson and Lisbeth Olsson. Characterization and kinetic analysis of a thermostable GH3 β-glucosidase from *Penicillium brasilianum*. Applied Microbiology and Biotechnology 2010, 86, 143-154.
10. Robert A. Copeland. Kinetics of single-substrate enzyme reactions. In *Enzymes: A Practical Introduction to Structure, Mechanism and Data Analysis,* 2 ed. 2000, 109-145.
11. Luiza P. Calsavara, Flávio F. De Moraes and Gisella M. Zanin. Modeling cellobiose hydrolysis with integrated kinetic models. Applied Biochemistry and Biotechnology 1999, 77-79, 789-806.
12. T. K. Ghose. Measurement of cellulase activitys. Pure and Applied Chemistry 1987, 59(2): 257-268.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An improved beta-glucosidase comprising a polypeptide having at least 95% sequence identity to the amino acid sequence of SEQ ID NOS: 2, 4, 6, 8, 10, 12 or 14, and having improved beta-glucosidase activity compared to a control beta-glucosidase comprising the amino acid sequence of SEQ ID NO:2, wherein the improved beta-glucosidase comprises one or more amino acids selected from:
   (a) an amino acid other than T at a position corresponding to position 66 of SEQ ID NO:2;
   (b) an amino acid other than L at a position corresponding to position 70 of SEQ ID NO:2;
   (c) an amino acid other than G at a position corresponding to position 136 of SEQ ID NO:2;
   (d) an amino acid other than I at a position corresponding to position 139 of SEQ ID NO:2;
   (e) an amino acid other than L at a position corresponding to position 167 of SEQ ID NO:2;
   (f) an amino acid other than Q at a position corresponding to position 250 of SEQ ID NO:2;
   (g) an amino acid other than A at a position corresponding to position 286 of SEQ ID NO:2;
   (h) an amino acid other than Y at a position corresponding to position 363 of SEQ ID NO:2;
   (i) an amino acid other than Y at a position corresponding to position 375 of SEQ ID NO:2;
   (j) an amino acid other than E at a position corresponding to position 376 of SEQ ID NO:2;
   (k) an amino acid other than Y at a position corresponding to position 610 of SEQ ID NO:2; and
   (l) an amino acid other than N at a position corresponding to position 791 of SEQ ID NO:2.

2. The improved beta-glucosidase of claim 1, wherein the improved beta-glucosidase comprises one or more amino acids selected from:
   (a) an isoleucine at a position corresponding to position 66 of SEQ ID NO:2;
   (b) a serine at a position corresponding to position 70 of SEQ ID NO:2;
   (c) a cysteine at a position corresponding to position 136 of SEQ ID NO:2;
   (d) a phenylalanine at a position corresponding to position 139 of SEQ ID NO:2;
   (e) a methionine at a position corresponding to position 167 of SEQ ID NO:2;
   (f) a leucine at a position corresponding to position 250 of SEQ ID NO:2;
   (g) an aspartic acid at a position corresponding to position 286 of SEQ ID NO:2;
   (h) a cysteine at a position corresponding to position 363 of SEQ ID NO:2;
   (i) a phenylalanine at a position corresponding to position 375 of SEQ ID NO:2;
   (j) a lysine at a position corresponding to position 376 of SEQ ID NO:2;
   (k) a phenylalanine at a position corresponding to position 610 of SEQ ID NO:2; and
   (l) an isoleucine at a position corresponding to position 791 of SEQ ID NO:2.

3. A method for converting a cellulose-containing biomass feedstock into a sugar, the method comprising treating the biomass with the improved beta-glucosidase of claim 1, or with a cell that expresses the improved beta-glucosidase of claim 1.

4. The method of claim 3, wherein the cellulose-containing biomass feedstock comprises cellobiose, and the improved beta-glucosidase increases the conversion of cellobiose to glucose in the presence of higher concentrations of glucose as compared to a control beta-glucosidase comprising the amino acid sequence of SEQ ID NO:2.

5. The method of claim 4, wherein the improved beta-glucosidase increases the conversion of cellobiose to glucose in the presence of 10-15% w/v glucose.

6. The method of claim 4, wherein the improved beta-glucosidase has improved kinetic properties compared to the control beta-glucosidase.

7. The method of claim 6, wherein the improved kinetic properties are selected from increased catalytic efficiency (Kcat/Km/min), increased maximum velocity (Vmax), and increased turnover number (Kcat/min).

8. The method of claim 3, further comprising fermenting the sugar to ethanol.

9. The method of claim 3, wherein the cell is a *Saccharomyces cerevisiae*.

10. The method of claim 3, wherein the cellulose-containing biomass feedstock is a woody material.

11. The method of claim 10, wherein the woody material is cellulosic or lignocellulosic plant material selected from the group consisting of orchard prunings, chaparral, mill waste, urban wood waste, municipal waste, logging waste, forest thinnings, short-rotation woody crops, and industrial waste.

12. The method of claim 3, wherein the cellulose-containing biomass feedstock is a non-woody material.

13. The method of claim 12, wherein the non-woody material is selected from the group consisting of gramineous agricultural residue, wheat straw, oat straw, rice straw, barley straw, rye straw, flax straw, sugar cane, corn stover, corn stalks, corn cobs, corn husks, prairie grass, switchgrass, gamagrass, foxtail, sugar beet pulp, citrus fruit pulp, seed hulls, cellulosic animal wastes, lawn clippings, seaweed, bagasse, energy cane, and giant reed.

14. The method of claim 3, wherein the cellulose-containing biomass feedstock is corn grain, barley grain, milo grain, wheat grain or rice grain.

15. The method of claim 1, wherein the improved beta-glucosidase comprises a phenylalanine at a position corresponding to position 139 of SEQ ID NO:2, and an aspartic acid at a position corresponding to position 286 of SEQ ID NO:2.

* * * * *

SEQUENCE LISTING

```
<160> NUMBER OF SEQ ID NOS: 36

<210> SEQ ID NO 1
<211> LENGTH: 2580
<212> TYPE: DNA
<213> ORGANISM: Aspergillus niger
<220> FEATURE:
<223> OTHER INFORMATION: wild type beta-glucosidase (BG)

<400> SEQUENCE: 1
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtactgg ttgggaattg gaattgtgtg ttggtcaaac tggtggtgtt     240
ccaagattgg gtgttccagg tatgtgtttg caagattctc cattgggtgt tagagattct     300
gattataatt ctgcttttcc agctggtatg aatgttgctg ctacttggga taaaaatttg     360
gcttatttga gaggtaaagc tatgggtcaa gaattttctg ataaaggtgc tgatattcaa     420
ttgggtccag ctgctggtcc attgggtaga tctccagatg gtggtagaaa ttgggaaggt     480
ttttctccag atccagcttt gtctggtgtt tgtttgctg aaactattaa aggtattcaa     540
gatgctggtg ttgttgctac tgctaaacat tatattgctt atgaacaaga acattttaga     600
caagctccag aagctcaagg ttttggtttt aatatttctg aatctggttc tgctaatttg     660
gatgataaaa ctatgcatga attgtatttg tggccatttg ctgatgctat tagagctggt     720
gctggtgctg ttatgtgttc ttataatcaa attaataatt cttatggttg tcaaaattct     780
tatactttga ataaattgtt gaaagctgaa ttgggttttc aaggttttgt tatgtctgat     840
tgggctgctc atcatgctgg tgtttctggt gctttggctg gtttggatat gtctatgcca     900
ggtgatgttg attatgattc tggtacttct tattggggta ctaatttgac tatttctgtt     960
ttgaatggta ctgttccaca atggagagtt gatgatatgg ctgttagaat tatggctgct    1020
tattataaag ttggtagaga tagattgtgg actccaccaa atttttcttc ttggactaga    1080
gatgaatatg gttataaata ttattatgtt tctgaaggtc catatgaaaa agttaatcaa    1140
tatgttaatg ttcaaagaaa tcattctgaa ttgattagaa gaattggtgc tgattctact    1200
gttttgttga aaaatgatgg tgctttgcca ttgactggta agaaagatt ggttgctttg    1260 attggtgaag atgctggttc taatccatat ggtgctaatg gttgttctga tagaggttgt    1320
gataatggta ctttggctat gggttggggt tctgtactg ctaattttcc atatttggtt    1380
```

-continued

```
actccagaac aagctatttc taatgaagtt ttgaaacata aaaatggtgt ttttactgct    1440
actgataatt gggctattga tcaaattgaa gctttggcta aaactgcttc tgtttctttg    1500 gttttttgtta atgctgattc tggtgaaggt tatattaatg ttgatggtaa tttgggtgat    1560
agaagaaatt tgactttgtg gagaaatggt gataatgtta ttaaagctgc tgcttctaat    1620
tgtaataata ctattgttgt tattcattct gttggtccag ttttggttaa tgaatggtat    1680
gataatccaa atgttactgc tattttgtgg ggtggtttgc caggtcaaga atctggtaat    1740
tctttggctg atgttttgta tggtagagtt aatccaggtg ctaaatctcc atttacttgg    1800
ggtaaaacta gagaagctta tcaagattat ttggttactg aaccaaataa tggtaatggt    1860
gctccacaag aagatttgt tgaaggtgtt tttattgatt atagaggttt tgataaaaga    1920
aatgaaactc caatttatga atttggttat ggtttgtctt atactacttt taattattct    1980
aatttggaag ttcaagtttt gtctgctcca gcttatgaac cagcttctgg tgaaactgaa    2040
gctgctccaa cttttggtga agttggtaat gcttctgatt atttgtatcc atctggtttg    2100
caaagaatta ctaaatttat ttatccatgg ttgaatggta ctgatttgga agcttcttct    2160
ggtgatgctt cttatggtca agattcttct gattatttgc cagaaggtgc tactgatggt    2220
tctgctcaac caattttgcc agctggtggt ggtccaggtg gtaatccaag attgtatgat    2280
gaattgatta gagtttctgt tactattaaa aatactggta agttgctggt tgatgaagtt    2340
ccacaattgt atgtttcttt gggtggtcca atgaaccaa aaattgtttt gagacaattt    2400
gaaagaatta ctttgcaacc atctgaagaa actaaatggt ctactacttt gactagaaga    2460
gatttggcta attggaatgt tgaaaaacaa gattgggaaa ttacttctta tccaaaaatg    2520 gttttttgttg gttcttcttc tagaaaattg ccattgagag cttctttgcc aactgttcat    2580
```

<210> SEQ ID NO 2
<211> LENGTH: 860
<212> TYPE: PRT
<213> ORGANISM: Aspergillus niger
<220> FEATURE:
<223> OTHER INFORMATION: wild type beta-glucosidase (BG)

<400> SEQUENCE: 2

```
Met Arg Phe Thr Leu Ile Glu Ala Val Ala Leu Thr Ala Val Ser Leu
  1               5                  10                  15

Ala Ser Ala Asp Glu Leu Ala Tyr Ser Pro Pro Tyr Tyr Pro Ser Pro
             20                  25                  30

Trp Ala Asn Gly Gln Gly Asp Trp Ala Gln Ala Tyr Gln Arg Ala Val
         35                  40                  45

Asp Ile Val Ser Gln Met Thr Leu Asp Glu Lys Val Asn Leu Thr Thr
     50                  55                  60

Gly Thr Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
```

```
            145                 150                 155                 160
        Phe Ser Pro Asp Pro Ala Leu Ser Gly Val Leu Phe Ala Glu Thr Ile
                        165                 170                 175
        Lys Gly Ile Gln Asp Ala Gly Val Val Ala Thr Ala Lys His Tyr Ile
                        180                 185                 190
        Ala Tyr Glu Gln Glu His Phe Arg Gln Ala Pro Glu Ala Gln Gly Phe
                        195                 200                 205
        Gly Phe Asn Ile Ser Glu Ser Gly Ser Ala Asn Leu Asp Asp Lys Thr
        210                 215                 220
        Met His Glu Leu Tyr Leu Trp Pro Phe Ala Asp Ala Ile Arg Ala Gly
        225                 230                 235                 240
        Ala Gly Ala Val Met Cys Ser Tyr Asn Gln Ile Asn Asn Ser Tyr Gly
                        245                 250                 255
        Cys Gln Asn Ser Tyr Thr Leu Asn Lys Leu Leu Lys Ala Glu Leu Gly
                        260                 265                 270
        Phe Gln Gly Phe Val Met Ser Asp Trp Ala Ala His His Ala Gly Val
                        275                 280                 285
        Ser Gly Ala Leu Ala Gly Leu Asp Met Ser Met Pro Gly Asp Val Asp
        290                 295                 300
        Tyr Asp Ser Gly Thr Ser Tyr Trp Gly Thr Asn Leu Thr Ile Ser Val
        305                 310                 315                 320
        Leu Asn Gly Thr Val Pro Gln Trp Arg Val Asp Asp Met Ala Val Arg
                        325                 330                 335
        Ile Met Ala Ala Tyr Tyr Lys Val Gly Arg Asp Arg Leu Trp Thr Pro
                        340                 345                 350
        Pro Asn Phe Ser Ser Trp Thr Arg Asp Glu Tyr Gly Tyr Lys Tyr Tyr
                        355                 360                 365
        Tyr Val Ser Glu Gly Pro Tyr Glu Lys Val Asn Gln Tyr Val Asn Val
                        370                 375                 380
        Gln Arg Asn His Ser Glu Leu Ile Arg Ile Gly Ala Asp Ser Thr
        385                 390                 395                 400
        Val Leu Leu Lys Asn Asp Gly Ala Leu Pro Leu Thr Gly Lys Glu Arg
                        405                 410                 415
        Leu Val Ala Leu Ile Gly Glu Asp Ala Gly Ser Asn Pro Tyr Gly Ala
                        420                 425                 430
        Asn Gly Cys Ser Asp Arg Gly Cys Asp Asn Gly Thr Leu Ala Met Gly
                        435                 440                 445
        Trp Gly Ser Gly Thr Ala Asn Phe Pro Tyr Leu Val Thr Pro Glu Gln
        450                 455                 460
        Ala Ile Ser Asn Glu Val Leu Lys His Lys Asn Gly Val Phe Thr Ala
        465                 470                 475                 480
        Thr Asp Asn Trp Ala Ile Asp Gln Ile Glu Ala Leu Ala Lys Thr Ala
                        485                 490                 495
        Ser Val Ser Leu Val Phe Val Asn Ala Asp Ser Gly Glu Gly Tyr Ile
                        500                 505                 510
        Asn Val Asp Gly Asn Leu Gly Asp Arg Arg Asn Leu Thr Leu Trp Arg
                        515                 520                 525
        Asn Gly Asp Asn Val Ile Lys Ala Ala Ser Asn Cys Asn Asn Thr
        530                 535                 540
        Ile Val Val Ile His Ser Val Gly Pro Val Leu Val Asn Glu Trp Tyr
        545                 550                 555                 560
        Asp Asn Pro Asn Val Thr Ala Ile Leu Trp Gly Gly Leu Pro Gly Gln
                        565                 570                 575
```

```
Glu Ser Gly Asn Ser Leu Ala Asp Val Leu Tyr Gly Arg Val Asn Pro
                580                 585                 590

Gly Ala Lys Ser Pro Phe Thr Trp Gly Lys Thr Arg Glu Ala Tyr Gln
            595                 600                 605

Asp Tyr Leu Val Thr Glu Pro Asn Asn Gly Asn Gly Ala Pro Gln Glu
        610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Tyr Gly Leu Ser Tyr Thr Thr
                645                 650                 655

Phe Asn Tyr Ser Asn Leu Glu Val Gln Val Leu Ser Ala Pro Ala Tyr
                660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Gln Arg Ile Thr
        690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Thr Lys Trp Ser Thr Thr
                805                 810                 815

Leu Thr Arg Arg Asp Leu Ala Asn Trp Asn Val Glu Lys Gln Asp Trp
                820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
    850                 855                 860

<210> SEQ ID NO 3
<211> LENGTH: 2580
<212> TYPE: DNA
<213> ORGANISM: Artificial Sequence
<220> FEATURE:
<223> OTHER INFORMATION: synthetic mutant beta-glucosidase (BG), BG
      acid/base mutant #8, yEdQ885 ->
      Y363C/Y375F/A446A/V498V/G510G/Y560Y/Y610F

<400> SEQUENCE: 3
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtactgg ttgggaattg gaattgtgtg ttggtcaaac tggtggtgtt     240
ccaagattgg gtgttccagg tatgtgtttt caagattctc cattgggtgt tagagattct     300
gattataatt ctgcttttcc agctggtatg aatgttgctg ctactgggga taaaaatttg     360
```

```
gcttatttga gaggtaaagc tatgggtcaa gaattttctg ataaaggtgc tgatattcaa    420
ttgggtccag ctgctggtcc attgggtaga tctccagatg gtggtagaaa ttgggaaggt    480
ttttctccag atccagcttt gtctggtgtt ttgtttgctg aaactattaa aggtattcaa    540
gatgctggtt tgttgctac  tgctaaacat tatattgctt atgaacaaga acattttaga    600
caagctccag aagctcaagg ttttggtttt aatatttctg aatctggttc tgctaatttg    660
gatgataaaa ctatgcatga attgtatttg tggccatttg ctgatgctat tagagctggt    720
gctggtgctg ttatgtgttc ttataatcaa attaataatt cttatggttg tcaaaattct    780
tatactttga ataaattgtt gaaagctgaa ttgggttttc aaggttttgt tatgtctgat    840
tgggctgctc atcatgctgg tgtttctggt gctttggctg gtttggatat gtctatgcca    900
ggtgatgttg attatgattc tggtacttct tattggggta ctaatttgac tatttctgtt    960
ttgaatggta ctgttccaca atggagagtt gatgatatgg ctgttagaat tatggctgct   1020
tattataaag ttggtagaga tagattgtgg actccaccaa attttctcttc ttggactaga   1080
gatgaatgtg gttataaata ttattatgtt tctgaaggtc catttgaaaa agttaatcaa   1140
tatgttaatg ttcaaagaaa tcattctgaa ttgattagaa gaattggtgc tgattctact   1200
gttttgttga aaaatgatgg tgctttgcca ttgactggta agaaagatt ggttgctttg    1260
attggtgaag atgctggttc taatccatat ggtgctaatg ttgttctga  tagaggttgt   1320
gataatggta ctttggcgat gggttggggt tctggtactg ctaattttcc atatttggtt   1380
actccagaac aagctatttc taatgaagtt ttgaaacata aaaatggtgt ttttactgct   1440
actgataatt gggctattga tcaaattgaa gctttggcta aaactgcttc tgtatctttg   1500
gttttttgtta atgctgattc tggtgaaggc tatattaatg ttgatggtaa tttgggtgat   1560
agaagaaatt tgactttgtg gagaaatggt gataatgtta ttaaagctgc tgcttctaat   1620
tgtaataata ctattgttgt tattcattct gttggtccag ttttggttaa tgaatggtac   1680
gataatccaa atgttactgc tattttgtgg ggtggtttgc caggtcaaga atctggtaat   1740
tctttggctg atgtttttgta tggtagagtt aatccaggtg ctaaatctcc atttacttgg   1800
ggtaaaacta gagaagctta tcaagatttt ttggttactg aaccaaataa tggtaatggt   1860
gctccacaag aagattttgt tgaaggtgtt tttattgatt atagaggttt tgataaaaga   1920
aatgaaactc caatttatga atttggttat ggtttgtctt atactacttt taattattct   1980
aatttggaag ttcaagtttt gtctgctcca gcttatgaac cagcttctgg tgaaactgaa   2040
gctgctccaa cttttggtga agttggtaat gcttctgatt atttgtatcc atctggtttg   2100
caaagaatta ctaaatttat ttatccatgg ttgaatggta ctgatttgga agcttcttct   2160
ggtgatgctt cttatggtca agattcttct gattatttgc cagaaggtgc tactgatggt   2220
tctgctcaac caattttgcc agctggtggt ggtccaggtg gtaatccaag attgtatgat   2280
gaattgatta gagtttctgt tactattaaa aatactggta agttgctgg  tgatgaagtt   2340
ccacaattgt atgtttcttt gggtggtcca aatgaaccaa aaattgtttt gagacaattt   2400
gaaagaatta ctttgcaacc atctgaagaa actaaatggt ctactacttt gactagaaga   2460
gatttggcta attggaatgt tgaaaaacaa gattgggaaa ttacttctta tccaaaaatg   2520
gttttttgttg gttcttcttc tagaaaattg ccattgagag cttctttgcc aactgttcat   2580
```

<210> SEQ ID NO 4
<211> LENGTH: 860
<212> TYPE: PRT
<213> ORGANISM: Artificial Sequence
<220> FEATURE:
<223> OTHER INFORMATION: synthetic mutant beta-glucosidase (BG), BG
      acid/base mutant #8, yEdQ885 ->
      Y363C/Y375F/A446A/V498V/G510G/Y560Y/Y610F

<400> SEQUENCE: 4

```
Met Arg Phe Thr Leu Ile Glu Ala Val Ala Leu Thr Ala Val Ser Leu
 1               5                  10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Cys Gly Tyr Lys Tyr Tyr
        355                 360                 365

Tyr Val Ser Glu Gly Pro Phe Glu Lys Val Asn Gln Tyr Val Asn Val
370                 375                 380
```

```
Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
                420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
        450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
                500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
            565                 570                 575

Glu Ser Gly Asn Ser Leu Ala Asp Val Leu Tyr Gly Arg Val Asn Pro
        580                 585                 590

Gly Ala Lys Ser Pro Phe Thr Trp Gly Lys Thr Arg Glu Ala Tyr Gln
        595                 600                 605

Asp Phe Leu Val Thr Glu Pro Asn Asn Gly Asn Gly Ala Pro Gln Glu
            610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
        690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
            725                 730                 735

Ala Thr Asp Gly Ser Ala Gln Pro Ile Leu Pro Ala Gly Gly Gly Pro
        740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
        770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
```

```
                    805                 810                 815
Leu Thr Arg Arg Asp Leu Ala Asn Trp Asn Val Glu Lys Gln Asp Trp
        820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
        850                 855                 860

<210> SEQ ID NO 5
<211> LENGTH: 2580
<212> TYPE: DNA
<213> ORGANISM: Artificial Sequence
<220> FEATURE:
<223> OTHER INFORMATION: synthetic mutant beta-glucosidase (BG), BG Orf
      mutant #1, yEdQ890 -> L70S/I139F

<400> SEQUENCE: 5
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtactgg ttgggaatcg aattgtgtg ttggtcaaac tggtggtgtt      240
ccaagattgg gtgttccagg tatgtgtttg caagattctc cattgggtgt tagagattct     300
gattataatt ctgcttttcc agctggtatg aatgttgctg ctacttggga taaaaatttg     360
gcttatttga gaggtaaagc tatgggtcaa gaattttctg ataaaggtgc tgattttcaa     420
ttgggtccag ctgctggtcc attgggtaga tctccagatg gtagaaa ttgggaaggt       480 ttttctccag atccagcttt gtctggtgtt tgtttgctg aaactattaa aggtattcaa       540
gatgctggtg ttgttgctac tgctaaacat tatattgctt atgaacaaga acattttaga     600
caagctccag aagctcaagg ttttggtttt aatatttctg aatctggttc tgctaatttg     660
gatgataaaa ctatgcatga attgtatttg tggccatttg ctgatgctat tagagctggt     720
gctggtgctg ttatgtgttc ttataatcaa attaataatt cttatggttg tcaaaattct     780
tatactttga ataaattgtt gaaagctgaa ttgggttttc aaggttttgt tatgtctgat     840
tgggctgctc atcatgctgg tgtttctggt gctttggctg gtttggatat gtctatgcca     900
ggtgatgttg attatgattc tggtacttct tattggggta ctaatttgac tatttctgtt     960
ttgaatggta ctgttccaca atggagagtt gatgatatgg ctgttagaat tatggctgct    1020
tattataaag ttggtagaga tagattgtgg actccaccaa ttttttcttc ttggactaga    1080
gatgaatatg gttataaata ttattatgtt tctgaaggtc catatgaaaa agttaatcaa    1140
tatgttaatg ttcaaagaaa tcattctgaa ttgattagaa gaattggtgc tgattctact    1200
gttttgttga aaaatgatgg tgctttgcca ttgactggta agaaagatt ggttgctttg      1260 attggtgaag atgctggttc taatccatat ggtgctaatg ttgttctga tagaggttgt     1320 gataatggta ctttggctat gggttggggt tctggtactg ctaattttcc atatttggtt    1380
actccagaac aagctatttc taatgaagtt ttgaaacata aaaatggtgt ttttactgct    1440
actgataatt gggctattga tcaaattgaa gctttggcta aaactgcttc tgtttctttg    1500 gttttttgtta atgctgattc tggtgaaggt tatattaatg ttgatggtaa tttgggtgat    1560
agaagaaatt tgactttgtg gagaaatggt gataatgtta ttaaagctgc tgcttctaat    1620
tgtaataata ctattgttgt tattcattct gttggtccag ttttggttaa tgaatggtat    1680
gataatccaa atgttactgc tatttttgtgg ggtggtttgc aggtcaaga atctggtaat    1740
```

```
tctttggctg atgttttgta tggtagagtt aatccaggtg ctaaatctcc atttacttgg    1800
ggtaaaacta gagaagctta tcaagattat ttggttactg aaccaaataa tggtaatggt    1860
gctccacaag aagattttgt tgaaggtgtt tttattgatt atagaggttt tgataaagaa    1920
aatgaaactc caatttatga atttggttat ggtttgtctt atactacttt taattattct    1980
aatttggaag ttcaagtttt gtctgctcca gcttatgaac cagcttctgg tgaaactgaa    2040
gctgctccaa cttttggtga agttggtaat gcttctgatt atttgtatcc atctggtttg    2100
caaagaatta ctaaatttat ttatccatgg ttgaatggta ctgatttgga agcttcttct    2160
ggtgatgctt cttatggtca agattcttct gattattttgc cagaaggtgc tactgatggt    2220
tctgctcaac caattttgcc agctggtggt ggtccaggtg gtaatccaag attgtatgat    2280
gaattgatta gagtttctgt tactattaaa aatactggta agttgctggg tgatgaagtt    2340
ccacaattgt atgtttcttt gggtggtcca atgaaccaa aaattgtttt gagacaattt    2400
gaaagaatta ctttgcaacc atctgaagaa actaaatggt ctactacttt gactagaaga    2460
gatttggcta attggaatgt tgaaaaacaa gattgggaaa ttacttctta tccaaaaatg    2520 gttttgttg ttcttcttc tagaaaattg ccattgagag cttctttgcc aactgttcat    2580
```

<210> SEQ ID NO 6
<211> LENGTH: 860
<212> TYPE: PRT
<213> ORGANISM: Artificial Sequence
<220> FEATURE:
<223> OTHER INFORMATION: synthetic mutant beta-glucosidase (BG), BG Orf
      mutant #1, yEdQ890 -> L70S/I139F

<400> SEQUENCE: 6

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Ser Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Phe Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205
```

```
Gly Phe Asn Ile Ser Glu Ser Gly Ser Ala Asn Leu Asp Asp Lys Thr
    210                 215                 220
Met His Glu Leu Tyr Leu Trp Pro Phe Ala Asp Ala Ile Arg Ala Gly
225                 230                 235                 240
Ala Gly Ala Val Met Cys Ser Tyr Asn Gln Ile Asn Asn Ser Tyr Gly
                245                 250                 255
Cys Gln Asn Ser Tyr Thr Leu Asn Lys Leu Leu Lys Ala Glu Leu Gly
            260                 265                 270
Phe Gln Gly Phe Val Met Ser Asp Trp Ala Ala His His Ala Gly Val
            275                 280                 285
Ser Gly Ala Leu Ala Gly Leu Asp Met Ser Met Pro Gly Asp Val Asp
    290                 295                 300
Tyr Asp Ser Gly Thr Ser Tyr Trp Gly Thr Asn Leu Thr Ile Ser Val
305                 310                 315                 320
Leu Asn Gly Thr Val Pro Gln Trp Arg Val Asp Met Ala Val Arg
                325                 330                 335
Ile Met Ala Ala Tyr Tyr Lys Val Gly Arg Asp Arg Leu Trp Thr Pro
            340                 345                 350
Pro Asn Phe Ser Ser Trp Thr Arg Asp Glu Tyr Gly Tyr Lys Tyr Tyr
            355                 360                 365
Tyr Val Ser Glu Gly Pro Tyr Glu Lys Val Asn Gln Tyr Val Asn Val
370                 375                 380
Gln Arg Asn His Ser Glu Leu Ile Arg Arg Ile Gly Ala Asp Ser Thr
385                 390                 395                 400
Val Leu Leu Lys Asn Asp Gly Ala Leu Pro Leu Thr Gly Lys Glu Arg
                405                 410                 415
Leu Val Ala Leu Ile Gly Glu Asp Ala Gly Ser Asn Pro Tyr Gly Ala
                420                 425                 430
Asn Gly Cys Ser Asp Arg Gly Cys Asp Asn Gly Thr Leu Ala Met Gly
            435                 440                 445
Trp Gly Ser Gly Thr Ala Asn Phe Pro Tyr Leu Val Thr Pro Glu Gln
    450                 455                 460
Ala Ile Ser Asn Glu Val Leu Lys His Lys Asn Gly Val Phe Thr Ala
465                 470                 475                 480
Thr Asp Asn Trp Ala Ile Asp Gln Ile Glu Ala Leu Ala Lys Thr Ala
                485                 490                 495
Ser Val Ser Leu Val Phe Val Asn Ala Asp Ser Gly Glu Gly Tyr Ile
            500                 505                 510
Asn Val Asp Gly Asn Leu Gly Asp Arg Arg Asn Leu Thr Leu Trp Arg
            515                 520                 525
Asn Gly Asp Asn Val Ile Lys Ala Ala Ala Ser Asn Cys Asn Asn Thr
    530                 535                 540
Ile Val Val Ile His Ser Val Gly Pro Val Leu Val Asn Glu Trp Tyr
545                 550                 555                 560
Asp Asn Pro Asn Val Thr Ala Ile Leu Trp Gly Gly Leu Pro Gly Gln
                565                 570                 575
Glu Ser Gly Asn Ser Leu Ala Asp Val Leu Tyr Gly Arg Val Asn Pro
            580                 585                 590
Gly Ala Lys Ser Pro Phe Thr Trp Gly Lys Thr Arg Glu Ala Tyr Gln
            595                 600                 605
Asp Tyr Leu Val Thr Glu Pro Asn Asn Gly Asn Gly Ala Pro Gln Glu
    610                 615                 620
Asp Phe Val Glu Gly Val Phe Ile Asp Tyr Arg Gly Phe Asp Lys Arg
```

```
                625                 630                 635                 640
Asn Glu Thr Pro Ile Tyr Glu Phe Gly Tyr Gly Leu Ser Tyr Thr Thr
                    645                 650                 655
Phe Asn Tyr Ser Asn Leu Glu Val Gln Val Leu Ser Ala Pro Ala Tyr
                    660                 665                 670
Glu Pro Ala Ser Gly Glu Thr Glu Ala Ala Pro Thr Phe Gly Glu Val
                    675                 680                 685
Gly Asn Ala Ser Asp Tyr Leu Tyr Pro Ser Gly Leu Gln Arg Ile Thr
                    690                 695                 700
Lys Phe Ile Tyr Pro Trp Leu Asn Gly Thr Asp Leu Glu Ala Ser Ser
705                 710                 715                 720
Gly Asp Ala Ser Tyr Gly Gln Asp Ser Ser Asp Tyr Leu Pro Glu Gly
                    725                 730                 735
Ala Thr Asp Gly Ser Ala Gln Pro Ile Leu Pro Ala Gly Gly Gly Pro
                    740                 745                 750
Gly Gly Asn Pro Arg Leu Tyr Asp Glu Leu Ile Arg Val Ser Val Thr
                    755                 760                 765
Ile Lys Asn Thr Gly Lys Val Ala Gly Asp Glu Val Pro Gln Leu Tyr
770                 775                 780
Val Ser Leu Gly Gly Pro Asn Glu Pro Lys Ile Val Leu Arg Gln Phe
785                 790                 795                 800
Glu Arg Ile Thr Leu Gln Pro Ser Glu Glu Thr Lys Trp Ser Thr Thr
                    805                 810                 815
Leu Thr Arg Arg Asp Leu Ala Asn Trp Asn Val Glu Lys Gln Asp Trp
                    820                 825                 830
Glu Ile Thr Ser Tyr Pro Lys Met Val Phe Val Gly Ser Ser Ser Arg
                    835                 840                 845
Lys Leu Pro Leu Arg Ala Ser Leu Pro Thr Val His
    850                 855                 860

<210> SEQ ID NO 7
<211> LENGTH: 2580
<212> TYPE: DNA
<213> ORGANISM: Artificial Sequence
<220> FEATURE:
<223> OTHER INFORMATION: synthetic mutant beta-glucosidase (BG), BG Orf
      mutant #6, yEdQ891 -> P152P/L167M/A286D/T835T

<400> SEQUENCE: 7
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtactgg ttgggaattg aattgtgtg ttggtcaaac tggtggtgtt      240
ccaagattgg gtgttccagg tatgtgtttg caagattctc cattgggtgt tagagattct     300
gattataatt ctgcttttcc agctggtatg aatgttgctg ctacttggga taaaaatttg     360
gcttatttga gaggtaaagc tatgggtcaa gaattttctg ataaaggtgc tgatattcaa     420
ttgggtccag ctgctggtcc attgggtaga tctcctgatg gtggtagaaa ttgggaaggt     480
ttttctccaa atccagctat gtctggtgtt tgtttgctg aaactattaa aggtattcaa       540
gatgctggtg ttgttgctac tgctaaacat tatattgctt atgaacaaga acatttagaa    600
caagctccag aagctcaagg ttttggtttt aatatttctg aatctggttc tgctaatttg     660
gatgataaaa ctatgcatga attgtatttg tggccatttg ctgatgctat tagagctggt     720
```

```
gctggtgctg ttatgtgttc ttataatcaa attaataatt cttatggttg tcaaaattct    780
tatactttga ataaattgtt gaaagctgaa ttgggttttc aaggttttgt tatgtctgat    840
tgggctgctc atcatgatgg tgtttctggt gctttggctg gtttggatat gtctatgcca    900
ggtgatgttg attatgattc tggtacttct tattggggta ctaatttgac tatttctgtt    960
ttgaatggta ctgttccaca atggagagtt gatgatatgg ctgttagaat tatggctgct   1020
tattataaag ttggtagaga tagattgtgg actccaccaa ttttttcttc ttggactaga   1080
gatgaatatg gttataaata ttattatgtt tctgaaggtc catatgaaaa agttaatcaa   1140
tatgttaatg ttcaaagaaa tcattctgaa ttgattagaa gaattggtgc tgattctact   1200
gttttgttga aaaatgatgg tgctttgcca ttgactggta agaaagatt ggttgctttg    1260 attggtgaag atgctggttc taatccatat ggtgctaatg ttgttctga tagaggttgt    1320 gataatggta ctttggctat gggttggggt tctggtactg ctaattttcc atatttggtt   1380
actccagaac aagctatttc taatgaagtt ttgaaacata aaaatggtgt ttttactgct   1440
actgataatt gggctattga tcaaattgaa gctttggcta aaactgcttc tgtttctttg   1500 gttttttgtta atgctgattc tggtgaaggt tatattaatg ttgatggtaa tttgggtgat   1560
agaagaaatt tgactttgtg gagaaatggt gataatgtta ttaaagctgc tgcttctaat   1620
tgtaataata ctattgttgt tattcattct gttggtccag ttttggttaa tgaatggtat   1680
gataatccaa atgttactgc tatttttgtgg ggtggtttgc caggtcaaga atctggtaat   1740 tcttttggctg atgttttgta tggtagagtt aatccaggtg ctaaatctcc atttacttgg   1800
ggtaaaacta gagaagctta tcaagattat ttggttactg aaccaaataa tggtaatggt   1860
gctccacaag aagatttgt tgaaggtgtt tttattgatt atagaggttt tgataaaaga   1920
aatgaaactc caattatga atttggttat ggtttgtctt atactacttt taattattct   1980
aatttggaag ttcaagtttt gtctgctcca gcttatgaac cagcttctgg tgaaactgaa   2040
gctgctccaa cttttggtga agttggtaat gcttctgatt atttgtatcc atctggtttg   2100
caaagaatta ctaaatttat ttatccatgg ttgaatggta ctgatttgga agcttcttct   2160
ggtgatgctt cttatggtca agattcttct gattatttgc cagaaggtgc tactgatggt   2220
tctgctcaac caatttttgcc agctggtggt ggtccaggtg gtaatccaag attgtatgat   2280
gaattgatta gagtttctgt tactattaaa aatactggta agttgctgg tgatgaagtt   2340 ccacaattgt atgtttcttt gggtggtcca aatgaaccaa aaattgtttt gagacaattt   2400
gaaagaatta ctttgcaacc atctgaagaa actaaatggt ctactacttt gactagaaga   2460
gatttggcta attggaatgt tgaaaaacaa gattgggaaa ttacatctta tccaaaaatg   2520 gttttttgttg gttcttcttc tagaaaattg ccattgagag cttctttgcc aactgttcat   2580
```

<210> SEQ ID NO 8
<211> LENGTH: 860
<212> TYPE: PRT
<213> ORGANISM: Artificial Sequence
<220> FEATURE:
<223> OTHER INFORMATION: synthetic mutant beta-glucosidase (BG), BG Orf
      mutant #6, yEdQ891 -> P152P/L167M/A286D/T835T

<400> SEQUENCE: 8

Met Arg Phe Thr Leu Ile Glu Ala Val Ala Leu Thr Ala Val Ser Leu
1               5                  10                  15

Ala Ser Ala Asp Glu Leu Ala Tyr Ser Pro Pro Tyr Tyr Pro Ser Pro
            20                  25                  30

-continued

```
Trp Ala Asn Gly Gln Gly Asp Trp Ala Gln Ala Tyr Gln Arg Ala Val
             35                  40                  45

Asp Ile Val Ser Gln Met Thr Leu Asp Glu Lys Val Asn Leu Thr Thr
 50                  55                  60

Gly Thr Gly Trp Glu Leu Glu Leu Cys Val Gly Gln Thr Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Met Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Asp Gly Val
        275                 280                 285

Ser Gly Ala Leu Ala Gly Leu Asp Met Ser Met Pro Gly Asp Val Asp
290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365

Tyr Val Ser Glu Gly Pro Tyr Glu Lys Val Asn Gln Tyr Val Asn Val
370                 375                 380

Gln Arg Asn His Ser Glu Leu Ile Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
```

```
                450             455             460
Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860

<210> SEQ ID NO 9
```

<211> LENGTH: 2580
<212> TYPE: DNA
<213> ORGANISM: Artificial Sequence
<220> FEATURE:
<223> OTHER INFORMATION: synthetic mutant beta-glucosidase (BG), BG Orf
      mutant #A, yEdQ892 -> G136C/E376K/A606A/N791I

<400> SEQUENCE: 9

```
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtactgg ttgggaattg aattgtgtg ttggtcaaac tggtggtgtt      240
ccaagattgg gtgttccagg tatgtgtttg caagattctc cattgggtgt tagagattct     300
gattataatt ctgcttttcc agctggtatg aatgttgctg ctacttggga taaaaatttg     360
gcttatttga gaggtaaagc tatgggtcaa gaattttctg ataaatgtgc tgatattcaa     420
ttgggtccag ctgctggtcc attgggtaga tctccagatg gtggtagaaa ttgggaaggt     480
ttttctccag atccagcttt gtctggtgtt ttgtttgctg aaactattaa aggtattcaa     540
gatgctggtt tgttgctac tgctaaacat tatattgctt atgaacaaga cattttttaga    600
caagctccag aagctcaagg ttttggtttt aatatttctg aatctggttc tgctaatttg     660
gatgataaaa ctatgcatga attgtatttg tggccatttg ctgatgctat tagagctggt     720
gctggtgctg ttatgtgttc ttataatcaa attaataatt cttatggttg tcaaaattct     780
tatactttga ataaattgtt gaaagctgaa ttgggttttc aaggttttgt tatgtctgat     840
tgggctgctc atcatgctgg tgtttctggt gctttggctg gtttggatat gtctatgcca     900
ggtgatgttg attatgattc tggtacttct tattggggta ctaatttgac tatttctgtt     960
ttgaatggta ctgttccaca atggagagtt gatgatatgg ctgttagaat tatggctgct    1020
tattataaag ttggtagaga tagattgtgg actccaccaa atttttcttc ttggactaga    1080
gatgaatatg gttataaata ttattatgtt tctgaaggtc catataaaaa agttaatcaa    1140
tatgttaatg ttcaaagaaa tcattctgaa ttgattagaa gaattggtgc tgattctact    1200
gttttgttga aaaatgatgg tgctttgcca ttgactggta agaaagatt ggttgctttg      1260
attggtgaag atgctggttc taatccatat ggtgctaatg ttgttctga tagaggttgt     1320
gataatggta ctttggctat gggttggggt tctggtactg ctaattttcc atatttggtt    1380
actccagaac aagctatttc taatgaagtt tgaaacata aaaatggtgt ttttactgct    1440
actgataatt gggctattga tcaaattgaa gctttggcta aaactgcttc tgtttctttg    1500
gttttttgtta atgctgattc tggtgaaggt tatattaatg ttgatggtaa tttgggtgat    1560
agaagaaatt tgacttttgtg agaaatggt gataatgtta ttaaagctgc tgcttctaat    1620
tgtaataata ctattgttgt tattcattct gttggtccag ttttggttaa tgaatggtat    1680
gataatccaa atgttactgc tattttgtgg ggtggtttgc aggtcaaga atctggtaat     1740
tctttggctg atgttttgta tggtagagtt aatccaggtg ctaaatctcc atttacttgg    1800
ggtaaaacta gaagcata tcaagattat ttggttactg aaccaaataa tggtaatggt      1860
gctccacaag aagattttgt tgaaggtgtt tttattgatt atagaggttt tgataaaaga    1920
aatgaaactc caatttatga atttggttat ggtttgtctt atactacttt taattattct    1980
aatttggaag ttcaagtttt gtctgctcca gcttatgaac cagcttctgg tgaaactgaa    2040
gctgctccaa cttttggtga agttggtaat gcttctgatt atttgtatcc atctggttttg   2100
```

```
caaagaatta ctaaatttat ttatccatgg ttgaatggta ctgatttgga agcttcttct    2160
ggtgatgctt cttatggtca agattcttct gattatttgc cagaaggtgc tactgatggt    2220
tctgctcaac caattttgcc agctggtggt ggtccaggtg gtaatccaag attgtatgat    2280
gaattgatta gagtttctgt tactattaaa aatactggta agttgctggt gatgaagtt    2340 ccacaattgt atgtttcttt gggtggtcca attgaaccaa aaattgtttt gagacaattt    2400
gaaagaatta ctttgcaacc atctgaagaa actaaatggt ctactacttt gactagaaga    2460
gatttggcta attggaatgt tgaaaaacaa gattgggaaa ttacttctta tccaaaaatg    2520 gttttttgttg gttcttcttc tagaaaattg ccattgagag cttctttgcc aactgttcat    2580
```

<210> SEQ ID NO 10
<211> LENGTH: 860
<212> TYPE: PRT
<213> ORGANISM: Artificial Sequence
<220> FEATURE:
<223> OTHER INFORMATION: synthetic mutant beta-glucosidase (BG), BG Orf
      mutant #A, yEdQ892 -> G136C/E376K/A606A/N791I

<400> SEQUENCE: 10

```
Met Arg Phe Thr Leu Ile Glu Ala Val Ala Leu Thr Ala Val Ser Leu
  1               5                  10                  15

Ala Ser Ala Asp Glu Leu Ala Tyr Ser Pro Pro Tyr Tyr Pro Ser Pro
                 20                  25                  30

Trp Ala Asn Gly Gln Gly Asp Trp Ala Gln Ala Tyr Gln Arg Ala Val
             35                  40                  45

Asp Ile Val Ser Gln Met Thr Leu Asp Glu Lys Val Asn Leu Thr Thr
 50                  55                  60

Gly Thr Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Cys Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
```

-continued

```
            275                 280                 285
Ser Gly Ala Leu Ala Gly Leu Asp Met Ser Met Pro Gly Asp Val Asp
            290                 295                 300
Tyr Asp Ser Gly Thr Ser Tyr Trp Gly Thr Asn Leu Thr Ile Ser Val
305                 310                 315                 320
Leu Asn Gly Thr Val Pro Gln Trp Arg Val Asp Asp Met Ala Val Arg
                325                 330                 335
Ile Met Ala Ala Tyr Tyr Lys Val Gly Arg Asp Arg Leu Trp Thr Pro
            340                 345                 350
Pro Asn Phe Ser Ser Trp Thr Arg Asp Glu Tyr Gly Tyr Lys Tyr Tyr
                355                 360                 365
Tyr Val Ser Glu Gly Pro Tyr Lys Lys Val Asn Gln Tyr Val Asn Val
            370                 375                 380
Gln Arg Asn His Ser Glu Leu Ile Arg Arg Ile Gly Ala Asp Ser Thr
385                 390                 395                 400
Val Leu Leu Lys Asn Asp Gly Ala Leu Pro Leu Thr Gly Lys Glu Arg
                405                 410                 415
Leu Val Ala Leu Ile Gly Glu Asp Ala Gly Ser Asn Pro Tyr Gly Ala
            420                 425                 430
Asn Gly Cys Ser Asp Arg Gly Cys Asp Asn Gly Thr Leu Ala Met Gly
                435                 440                 445
Trp Gly Ser Gly Thr Ala Asn Phe Pro Tyr Leu Val Thr Pro Glu Gln
            450                 455                 460
Ala Ile Ser Asn Glu Val Leu Lys His Lys Asn Gly Val Phe Thr Ala
465                 470                 475                 480
Thr Asp Asn Trp Ala Ile Asp Gln Ile Glu Ala Leu Ala Lys Thr Ala
                485                 490                 495
Ser Val Ser Leu Val Phe Val Asn Ala Asp Ser Gly Glu Gly Tyr Ile
            500                 505                 510
Asn Val Asp Gly Asn Leu Gly Asp Arg Arg Asn Leu Thr Leu Trp Arg
            515                 520                 525
Asn Gly Asp Asn Val Ile Lys Ala Ala Ala Ser Asn Cys Asn Asn Thr
            530                 535                 540
Ile Val Val Ile His Ser Val Gly Pro Val Leu Val Asn Glu Trp Tyr
545                 550                 555                 560
Asp Asn Pro Asn Val Thr Ala Ile Leu Trp Gly Gly Leu Pro Gly Gln
                565                 570                 575
Glu Ser Gly Asn Ser Leu Ala Asp Val Leu Tyr Gly Arg Val Asn Pro
                580                 585                 590
Gly Ala Lys Ser Pro Phe Thr Trp Gly Lys Thr Arg Glu Ala Tyr Gln
            595                 600                 605
Asp Tyr Leu Val Thr Glu Pro Asn Asn Gly Asn Gly Ala Pro Gln Glu
            610                 615                 620
Asp Phe Val Glu Gly Val Phe Ile Asp Tyr Arg Gly Phe Asp Lys Arg
625                 630                 635                 640
Asn Glu Thr Pro Ile Tyr Glu Phe Gly Tyr Gly Leu Ser Tyr Thr Thr
                645                 650                 655
Phe Asn Tyr Ser Asn Leu Glu Val Gln Val Leu Ser Ala Pro Ala Tyr
                660                 665                 670
Glu Pro Ala Ser Gly Glu Thr Glu Ala Ala Pro Thr Phe Gly Glu Val
            675                 680                 685
Gly Asn Ala Ser Asp Tyr Leu Tyr Pro Ser Gly Leu Gln Arg Ile Thr
            690                 695                 700
```

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Asp Tyr Leu Pro Glu Gly
            725                 730                 735

Ala Thr Asp Gly Ser Ala Gln Pro Ile Leu Pro Ala Gly Gly Pro
            740                 745                 750

Gly Gly Asn Pro Arg Leu Tyr Asp Glu Leu Ile Arg Val Ser Val Thr
            755                 760                 765

Ile Lys Asn Thr Gly Lys Val Ala Gly Asp Glu Val Pro Gln Leu Tyr
            770                 775                 780

Val Ser Leu Gly Gly Pro Ile Glu Pro Lys Ile Val Leu Arg Gln Phe
785                 790                 795                 800

Glu Arg Ile Thr Leu Gln Pro Ser Glu Glu Thr Lys Trp Ser Thr Thr
            805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
    850                 855                 860

<210> SEQ ID NO 11
<211> LENGTH: 2580
<212> TYPE: DNA
<213> ORGANISM: Artificial Sequence
<220> FEATURE:
<223> OTHER INFORMATION: synthetic mutant beta-glucosidase (BG), BG Orf
      mutant #B, yEdQ893 -> T66I

<400> SEQUENCE: 11

```
atgagattta ctttgattga agctgttgct ttgactgctg tttctttggc ttctgctgat      60
gaattggctt attctccacc atattatcca tctccatggg ctaatggtca aggtgattgg     120
gctcaagctt atcaaagagc tgttgatatt gtttctcaaa tgactttgga tgaaaaagtt     180
aatttgacta ctggtattgg ttgggaattg gaattgtgtg ttggtcaaac tggtggtgtt     240
ccaagattgg gtgttccagg tatgtgtttg caagattctc cattgggtgt tagagattct     300
gattataatt ctgcttttcc agctggtatg aatgttgctg ctacttggga taaaaatttg     360
gcttatttga gaggtaaagc tatgggtcaa gaattttctg ataaaggtgc tgatattcaa     420
ttgggtccag ctgctggtcc attgggtaga tctccagatg gtagaaaa ttgggaaggt      480 ttttctccag atccagcttt gtctggtgtt tgtttgctg aaactattaa aggtattcaa      540
gatgctggtg ttgttgctac tgctaaacat tatattgctt atgaacaaga acattttaga     600
caagctccag aagctcaagg ttttggtttt aatatttctg aatctggttc tgctaatttg     660
gatgataaaa ctatgcatga attgtatttg tggccatttg ctgatgctat tagagctggt     720
gctggtgctg ttatgtgttc ttataatcaa attaataatt cttatggttg tcaaaattct     780
tatactttga ataaattgtt gaaagctgaa ttgggttttc aaggttttgt tatgtctgat     840
tgggctgctc atcatgctgg tgtttctggt gcttggctg tttggatat gtctatgcca      900 ggtgatgttg attatgattc tggtacttct tattggggta ctaatttgac tatttctgtt     960
ttgaatggta ctgttccaca atggagagtt gatgatatgg ctgttagaat atggctgct    1020 tattataaag ttggtagaga tagattgtgg actccaccaa attttctctt ttggactaga    1080
gatgaatatg gttataaata ttattatgtt tctgaaggtc catatgaaaa agttaatcaa    1140
```

```
tatgttaatg ttcaaagaaa tcattctgaa ttgattagaa gaattggtgc tgattctact   1200
gttttgttga aaatgatgg tgctttgcca ttgactggta agaaagatt ggttgctttg     1260 attggtgaag atgctggttc taatccatat ggtgctaatg ttgttctga tagaggttgt    1320 gataatggta ctttggctat gggttggggt tctggtactg ctaattttcc atatttggtt   1380
actccagaac aagctatttc taatgaagtt tgaaacata aaaatggtgt ttttactgct    1440
actgataatt gggctattga tcaaattgaa gctttggcta aaactgcttc tgtttctttg   1500 gttttgtta atgctgattc tggtgaaggt tatattaatg ttgatggtaa tttgggtgat    1560
agaagaaatt tgactttgtg gagaaatggt gataatgtta ttaaagctgc tgcttctaat   1620
tgtaataata ctattgttgt tattcattct gttggtccag ttttggttaa tgaatggtat   1680
gataatccaa atgttactgc tatttttgtgg ggtggttgc caggtcaaga atctggtaat   1740
tctttggctg atgttttgta tggtagagtt aatccaggtg ctaaatctcc atttacttgg   1800
ggtaaaacta gagaagctta tcaagattat ttggttactg aaccaaataa tggtaatggt   1860
gctccacaag aagattttgt tgaaggtgtt tttattgatt atagaggttt tgataaaaga   1920
aatgaaactc caatttatga atttggttat ggtttgtctt atactacttt taattattct   1980
aatttggaag ttcaagtttt gtctgctcca gcttatgaac cagcttctgg tgaaactgaa   2040
gctgctccaa cttttggtga agttggtaat gcttctgatt atttgtatcc atctggtttg   2100
caaagaatta ctaaatttat ttatccatgg ttgaatggta ctgatttgga agcttcttct   2160
ggtgatgctt cttatggtca agattcttct gattattttgc cagaaggtgc tactgatggt   2220
tctgctcaac caattttgcc agctggtggt ggtccaggtg taatccaag attgtatgat   2280 gaattgatta gagtttctgt tactattaaa aatactggta agttgctgg tgatgaagtt   2340 ccacaattgt atgtttcttt gggtggtcca aatgaaccaa aaattgtttt gagacaattt   2400
gaaagaatta ctttgcaacc atctgaagaa actaaatggt ctactacttt gactagaaga   2460
gatttggcta attggaatgt tgaaaaacaa gattgggaaa ttacttctta tccaaaaatg   2520
gtttttgttg gttcttcttc tagaaaattg ccattgagag cttcttttgcc aactgttcat   2580
```

<210> SEQ ID NO 12
<211> LENGTH: 860
<212> TYPE: PRT
<213> ORGANISM: Artificial Sequence
<220> FEATURE:
<223> OTHER INFORMATION: synthetic mutant beta-glucosidase (BG), BG Orf
      mutant #B, yEdQ893 -> T66I

<400> SEQUENCE: 12

```
Met Arg Phe Thr Leu Ile Glu Ala Val Ala Leu Thr Ala Val Ser Leu
 1               5                  10                  15

Ala Ser Ala Asp Glu Leu Ala Tyr Ser Pro Tyr Tyr Pro Ser Pro
             20                  25                  30

Trp Ala Asn Gly Gln Gly Asp Trp Ala Gln Ala Tyr Gln Arg Ala Val
         35                  40                  45

Asp Ile Val Ser Gln Met Thr Leu Asp Glu Lys Val Asn Leu Thr Thr
     50                  55                  60

Gly Ile Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                 85                  90                  95

Val Arg Asp Ser Asp Tyr Asn Ser Ala Phe Pro Ala Gly Met Asn Val
```

-continued

```
               100                 105                 110
Ala Ala Thr Trp Asp Lys Asn Leu Ala Tyr Leu Arg Gly Lys Ala Met
            115                 120                 125
Gly Gln Glu Phe Ser Asp Lys Gly Ala Asp Ile Gln Leu Gly Pro Ala
        130                 135                 140
Ala Gly Pro Leu Gly Arg Ser Pro Asp Gly Arg Asn Trp Glu Gly
145                 150                 155                 160
Phe Ser Pro Asp Pro Ala Leu Ser Gly Val Leu Phe Ala Glu Thr Ile
                165                 170                 175
Lys Gly Ile Gln Asp Ala Gly Val Val Ala Thr Ala Lys His Tyr Ile
            180                 185                 190
Ala Tyr Glu Gln Glu His Phe Arg Gln Ala Pro Glu Ala Gln Gly Phe
        195                 200                 205
Gly Phe Asn Ile Ser Glu Ser Gly Ser Ala Asn Leu Asp Asp Lys Thr
    210                 215                 220
Met His Glu Leu Tyr Leu Trp Pro Phe Ala Asp Ala Ile Arg Ala Gly
225                 230                 235                 240
Ala Gly Ala Val Met Cys Ser Tyr Asn Gln Ile Asn Asn Ser Tyr Gly
                245                 250                 255
Cys Gln Asn Ser Tyr Thr Leu Asn Lys Leu Leu Lys Ala Glu Leu Gly
            260                 265                 270
Phe Gln Gly Phe Val Met Ser Asp Trp Ala Ala His His Ala Gly Val
        275                 280                 285
Ser Gly Ala Leu Ala Gly Leu Asp Met Ser Met Pro Gly Asp Val Asp
    290                 295                 300
Tyr Asp Ser Gly Thr Ser Tyr Trp Gly Thr Asn Leu Thr Ile Ser Val
305                 310                 315                 320
Leu Asn Gly Thr Val Pro Gln Trp Arg Val Asp Met Ala Val Arg
                325                 330                 335
Ile Met Ala Ala Tyr Tyr Lys Val Gly Arg Asp Arg Leu Trp Thr Pro
            340                 345                 350
Pro Asn Phe Ser Ser Trp Thr Arg Asp Glu Tyr Gly Tyr Lys Tyr Tyr
        355                 360                 365
Tyr Val Ser Glu Gly Pro Tyr Glu Lys Val Asn Gln Tyr Val Asn Val
    370                 375                 380
Gln Arg Asn His Ser Glu Leu Ile Arg Ile Gly Ala Asp Ser Thr
385                 390                 395                 400
Val Leu Leu Lys Asn Asp Gly Ala Leu Pro Leu Thr Gly Lys Glu Arg
                405                 410                 415
Leu Val Ala Leu Ile Gly Glu Asp Ala Gly Ser Asn Pro Tyr Gly Ala
            420                 425                 430
Asn Gly Cys Ser Asp Arg Gly Cys Asp Asn Gly Thr Leu Ala Met Gly
        435                 440                 445
Trp Gly Ser Gly Thr Ala Asn Phe Pro Tyr Leu Val Thr Pro Glu Gln
    450                 455                 460
Ala Ile Ser Asn Glu Val Leu Lys His Lys Asn Gly Val Phe Thr Ala
465                 470                 475                 480
Thr Asp Asn Trp Ala Ile Asp Gln Ile Glu Ala Leu Ala Lys Thr Ala
                485                 490                 495
Ser Val Ser Leu Val Phe Val Asn Ala Asp Ser Gly Glu Gly Tyr Ile
            500                 505                 510
Asn Val Asp Gly Asn Leu Gly Asp Arg Arg Asn Leu Thr Leu Trp Arg
        515                 520                 525
```

Asn Gly Asp Asn Val Ile Lys Ala Ala Ala Ser Asn Cys Asn Asn Thr
            530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Ser Gly Leu Gln Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Ser Arg
        835                 840                 845

Lys Leu Pro Leu Arg Ala Ser Leu Pro Thr Val His
    850                 855                 860

<210> SEQ ID NO 13
<211> LENGTH: 2580
<212> TYPE: DNA
<213> ORGANISM: Artificial Sequence
<220> FEATURE:
<223> OTHER INFORMATION: synthetic mutant beta-glucosidase (BG), BG Orf
      mutant #16, yEdQ894 -> S247S/Q250L

<400> SEQUENCE: 13
atgagattta ctttgattga agctgttgct ttgactgctg tttctttggc ttctgctgat       60
gaattggctt attctccacc atattatcca tctccatggg ctaatggtca aggtgattgg      120

```
gctcaagctt atcaaagagc tgttgatatt gtttctcaaa tgactttgga tgaaaaagtt      180
aatttgacta ctggtactgg ttgggaattg gaattgtgtg ttggtcaaac tggtggtgtt      240
ccaagattgg gtgttccagg tatgtgtttg caagattctc cattgggtgt tagagattct      300
gattataatt ctgcttttcc agctggtatg aatgttgctg ctacttggga taaaaatttg      360
gcttatttga gaggtaaagc tatgggtcaa gaattttctg ataaaggtgc tgatattcaa      420
ttgggtccag ctgctggtcc attgggtaga tctccagatg gtggtagaaa ttgggaaggt      480
ttttctccag atccagcttt gtctggtgtt ttgtttgctg aaactattaa aggtattcaa      540
gatgctggtg ttgttgctac tgctaaacat tatattgctt atgaacaaga acattttaga      600
caagctccag aagctcaagg ttttggtttt aatatttctg aatctggttc tgctaatttg      660
gatgataaaa ctatgcatga attgtatttg tggccatttg ctgatgctat tagagctggt      720
gctggtgctg ttatgtgttc gtataatcta attaataatt cttatggttg tcaaaattct      780
tatactttga ataaattgtt gaaagctgaa ttgggttttc aaggttttgt tatgtctgat      840
tgggctgctc atcatgctgg tgtttctggt gctttggctg gtttggatat gtctatgcca      900
ggtgatgttg attatgattc tggtacttct tattggggta ctaatttgac tattctctgtt     960 ttgaatggta ctgttccaca atggagagtt gatgatatgg ctgttagaat tatggctgct     1020
tattataaag ttggtagaga tagattgtgg actccaccaa attttcttc ttggactaga      1080 gatgaatatg gttataaata ttattatgtt tctgaaggtc catatgaaaa agttaatcaa      1140
tatgttaatg ttcaaagaaa tcattctgaa ttgattagaa gaattggtgc tgattctact     1200
gttttgttga aaaatgatgg tgctttgcca ttgactggta agaaaagatt ggttgctttg     1260
attggtgaag atgctggttc taatccatat ggtgctaatg gttgttctga tagaggttgt     1320
gataatggta ctttggctat gggttggggt tctggtactg ctaattttcc atatttggtt     1380
actccagaac aagctatttc taatgaagtt ttgaaacata aaaatggtgt tttactgct      1440 actgataatt gggctattga tcaaattgaa gctttggcta aaactgcttc tgtttctttg     1500 gttttttgtta atgctgattc tggtgaaggt tatattaatg ttgatggtaa tttgggtgat     1560
agaagaaatt tgacttttgtg gagaaatggt gataatgtta ttaaagctgc tgcttctaat     1620
tgtaataata ctattgttgt tattcattct gttggtccag ttttggttaa tgaatggtat     1680
gataatccaa atgttactgc tatttttgtgg ggtggtttgc caggtcaaga atctggtaat     1740
tctttggctg atgttttgta tggtagagtt aatccaggtg ctaaatctcc atttacttgg     1800
ggtaaaacta gagaagctta tcaagattat ttggttactg aaccaaataa tggtaatggt     1860
gctccacaag aagatttgtg tgaaggtgtt tttattgatt atagaggttt tgataaaaga     1920
aatgaaactc caatttatga atttggttat ggtttgtctt atactacttt taattattct     1980
aatttggaag ttcaagtttt gtctgctcca gcttatgaac cagcttctgg tgaaactgaa     2040
gctgctccaa cttttggtga agttggtaat gcttctgatt atttgtatcc atctggtttg     2100
caaagaatta ctaaatttat ttatccatgg ttgaatggta ctgatttgga agcttcttct     2160
ggtgatgctt cttatggtca agattcttct gattatttgc cagaaggtgc tactgatggt     2220
tctgctcaac caatttttgcc agctggtggt ggtccaggtg gtaatccaag attgtatgat     2280
gaattgatta gagtttctgt tactattaaa aatactggta agttgctgg tgatgaagtt      2340 ccacaattgt atgtttcttt gggtggtcca aatgaaccaa aaattgtttt gagacaattt     2400
gaaagaatta ctttgcaacc atctgaagaa actaaatggt ctactacttt gactagaaga     2460
gatttggcta attggaatgt tgaaaaacaa gattgggaaa ttacttctta tccaaaaatg     2520
```
gtttttgttg gttcttcttc tagaaaattg ccattgagag cttctttgcc aactgttcat    2580

<210> SEQ ID NO 14
<211> LENGTH: 860
<212> TYPE: PRT
<213> ORGANISM: Artificial Sequence
<220> FEATURE:
<223> OTHER INFORMATION: synthetic mutant beta-glucosidase (BG), BG Orf
      mutant #16, yEdQ894 -> S247S/Q250L

<400> SEQUENCE: 14

```
Met Arg Phe Thr Leu Ile Glu Ala Val Ala Leu Thr Ala Val Ser Leu
 1               5                  10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
 50                  55                  60

Gly Thr Gly Trp Glu Leu Glu Leu Cys Val Gly Gln Thr Gly Gly Val
 65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Leu Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350
```

```
Pro Asn Phe Ser Ser Trp Thr Arg Asp Glu Tyr Gly Tyr Lys Tyr Tyr
    355                 360                 365

Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
            450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
            530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
            595                 600                 605

Asp Tyr Leu Val Thr Glu Pro Asn Asn Gly Asn Gly Ala Pro Gln Glu
            610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
            660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Gln Arg Ile Thr
            690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
            725                 730                 735

Ala Thr Asp Gly Ser Ala Gln Pro Ile Leu Pro Ala Gly Gly Gly Pro
            740                 745                 750

Gly Gly Asn Pro Arg Leu Tyr Asp Glu Leu Ile Arg Val Ser Val Thr
            755                 760                 765
```

```
Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
    785                 790                 795                 800

Glu Arg Ile Thr Leu Gln Pro Ser Glu Thr Lys Trp Ser Thr Thr
                805                 810                 815

Leu Thr Arg Arg Asp Leu Ala Asn Trp Asn Val Glu Lys Gln Asp Trp
            820                 825                 830

Glu Ile Thr Ser Tyr Pro Lys Met Val Phe Val Gly Ser Ser Arg
                835                 840                 845

Lys Leu Pro Leu Arg Ala Ser Leu Pro Thr Val His
    850                 855                 860
```

<210> SEQ ID NO 15
<211> LENGTH: 5
<212> TYPE: PRT
<213> ORGANISM: Artificial Sequence
<220> FEATURE:
<223> OTHER INFORMATION: synthetic beta-glucosidase (BG) highly
      conserved nucleophile site

<400> SEQUENCE: 15

```
Val Met Ser Asp Trp
1               5
```

<210> SEQ ID NO 16
<211> LENGTH: 27
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids 58-92
      of wild type beta-glucosidase (BG)

<400> SEQUENCE: 16

```
Glu Lys Val Asn Leu Thr Thr Gly Thr Gly Trp Glu Leu Glu Leu Cys
1               5                   10                  15

Val Gly Gln Thr Gly Gly Val Pro Arg Leu Gly
            20                  25
```

<210> SEQ ID NO 17
<211> LENGTH: 31
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      127-157 of wild type beta-glucosidase (BG)

<400> SEQUENCE: 17

```
Ala Met Gly Gln Glu Phe Ser Asp Lys Gly Ala Asp Ile Gln Leu Gly
1               5                   10                  15

Pro Ala Ala Gly Pro Leu Gly Arg Ser Pro Asp Gly Gly Arg Asn
            20                  25                  30
```

<210> SEQ ID NO 18
<211> LENGTH: 22
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      159-180 of wild type beta-glucosidase (BG)

<400> SEQUENCE: 18

Glu Gly Phe Ser Pro Asp Pro Ala Leu Ser Gly Val Leu Phe Ala Glu
1               5                   10                  15

Thr Ile Lys Gly Ile Gln
            20

<210> SEQ ID NO 19
<211> LENGTH: 19
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      242-260 of wild type beta-glucosidase (BG)

<400> SEQUENCE: 19

Gly Ala Val Met Cys Ser Tyr Asn Gln Ile Asn Asn Ser Tyr Gly Cys
1               5                   10                  15

Gln Asn Ser

<210> SEQ ID NO 20
<211> LENGTH: 31
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      272-302 of wild type beta-glucosidase (BG)

<400> SEQUENCE: 20

Gly Phe Gln Gly Phe Val Met Ser Asp Trp Ala Ala His His Ala Gly
1               5                   10                  15

Val Ser Gly Ala Leu Ala Gly Leu Asp Met Ser Met Pro Gly Asp
            20                  25                  30

<210> SEQ ID NO 21
<211> LENGTH: 18
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      362-379 of wild type beta-glucosidase (BG)

<400> SEQUENCE: 21

Glu Tyr Gly Tyr Lys Tyr Tyr Val Ser Glu Gly Pro Tyr Glu Lys
1               5                   10                  15

Val Asn

<210> SEQ ID NO 22
<211> LENGTH: 27
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      597-623 of wild type beta-glucosidase (BG)

<400> SEQUENCE: 22

Pro Phe Thr Trp Gly Lys Thr Arg Glu Ala Tyr Gln Asp Tyr Leu Val
1               5                   10                  15

Thr Glu Pro Asn Asn Gly Asn Gly Ala Pro Gln
            20                  25

<210> SEQ ID NO 23

```
<211> LENGTH: 24
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      780-803 of wild type beta-glucosidase (BG)

<400> SEQUENCE: 23

Val Pro Gln Leu Tyr Val Ser Leu Gly Gly Pro Asn Glu Pro Lys Ile
1               5                   10                  15

Val Leu Arg Gln Phe Glu Arg Ile
            20

<210> SEQ ID NO 24
<211> LENGTH: 26
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      272-297 of wild type beta-glucosidase (BG)
<220> FEATURE:
<221> NAME/KEY: VARIANT
<222> LOCATION: (11)...(11)
<223> OTHER INFORMATION: Xaa = Ala, Thr or Trp
<220> FEATURE:
<221> NAME/KEY: VARIANT
<222> LOCATION: (13)...(13)
<223> OTHER INFORMATION: Xaa = His or Gln
<220> FEATURE:
<221> NAME/KEY: VARIANT
<222> LOCATION: (15)...(15)
<223> OTHER INFORMATION: Xaa = Ala, Ser or Thr
<220> FEATURE:
<221> NAME/KEY: VARIANT
<222> LOCATION: (18)...(18)
<223> OTHER INFORMATION: Xaa = Ser, Gly or Ala
<220> FEATURE:
<221> NAME/KEY: VARIANT
<222> LOCATION: (19)...(19)
<223> OTHER INFORMATION: Xaa = Gly, Ala or Ser
<220> FEATURE:
<221> NAME/KEY: VARIANT
<222> LOCATION: (21)...(21)
<223> OTHER INFORMATION: Xaa = Leu or Val

<400> SEQUENCE: 24

Gly Phe Gln Gly Phe Val Met Ser Asp Trp Xaa Ala Xaa His Xaa Gly
1               5                   10                  15

Val Xaa Xaa Ala Xaa Ala Gly Leu Asp Met
            20                  25

<210> SEQ ID NO 25
<211> LENGTH: 26
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      272-297 of wild type beta-glucosidase (BG)
<220> FEATURE:
<221> NAME/KEY: VARIANT
<222> LOCATION: (11)...(11)
<223> OTHER INFORMATION: Xaa = Ala, Thr or Trp
<220> FEATURE:
<221> NAME/KEY: VARIANT
<222> LOCATION: (13)...(13)
<223> OTHER INFORMATION: Xaa = His or Gln
<220> FEATURE:
<221> NAME/KEY: VARIANT
<222> LOCATION: (15)...(15)
<223> OTHER INFORMATION: Xaa = Arg, Asn, Cys, Ile, Leu, Lys, Met, Phe,
```

```
              Pro, Trp, Tyr, Val, Asp, His, Gly, Gln or Glu
<220> FEATURE:
<221> NAME/KEY: VARIANT
<222> LOCATION: (18)...(18)
<223> OTHER INFORMATION: Xaa = Ser, Gly or Ala
<220> FEATURE:
<221> NAME/KEY: VARIANT
<222> LOCATION: (19)...(19)
<223> OTHER INFORMATION: Xaa = Gly, Ala or Ser
<220> FEATURE:
<221> NAME/KEY: VARIANT
<222> LOCATION: (21)...(21)
<223> OTHER INFORMATION: Xaa = Leu or Val

<400> SEQUENCE: 25

Gly Phe Gln Gly Phe Val Met Ser Asp Trp Xaa Ala Xaa His Xaa Gly
1               5                   10                  15

Val Xaa Xaa Ala Xaa Ala Gly Leu Asp Met
            20                  25

<210> SEQ ID NO 26
<211> LENGTH: 26
<212> TYPE: PRT
<213> ORGANISM: Artificial Sequence
<220> FEATURE:
<223> OTHER INFORMATION: synthetic genus Aspergillus beta-glucosidase
      (BG) conserved motif corresponding to amino acids
      272-297 of wild type beta-glucosidase (BG)
<220> FEATURE:
<221> NAME/KEY: VARIANT
<222> LOCATION: (11)...(11)
<223> OTHER INFORMATION: Xaa - Ala, Thr or Trp
<220> FEATURE:
<221> NAME/KEY: VARIANT
<222> LOCATION: (13)...(13)
<223> OTHER INFORMATION: Xaa = His or Gln
<220> FEATURE:
<221> NAME/KEY: VARIANT
<222> LOCATION: (18)...(18)
<223> OTHER INFORMATION: Xaa = Ser, Gly or Ala
<220> FEATURE:
<221> NAME/KEY: VARIANT
<222> LOCATION: (19)...(19)
<223> OTHER INFORMATION: Xaa = Gly, Ala or Ser
<220> FEATURE:
<221> NAME/KEY: VARIANT
<222> LOCATION: (21)...(21)
<223> OTHER INFORMATION: Xaa = Leu or Val

<400> SEQUENCE: 26

Gly Phe Gln Gly Phe Val Met Ser Asp Trp Xaa Ala Xaa His Asp Gly
1               5                   10                  15

Val Xaa Xaa Ala Xaa Ala Gly Leu Asp Met
            20                  25

<210> SEQ ID NO 27
<211> LENGTH: 25
<212> TYPE: DNA
<213> ORGANISM: Artificial Sequence
<220> FEATURE:
<223> OTHER INFORMATION: synthetic primer BG Orf FWD directed to
      beta-glucosidase (BG) ORF

<400> SEQUENCE: 27
atgagattta ctttgattga agctg                                         25

<210> SEQ ID NO 28
<211> LENGTH: 23
<212> TYPE: DNA
<213> ORGANISM: Artificial Sequence
<220> FEATURE:
```

<223> OTHER INFORMATION: synthetic primer BG Orf REV directed to
    beta-glucosidase (BG) ORF

<400> SEQUENCE: 28
ctaatgaaca gttggcaaag aag                                        23

<210> SEQ ID NO 29
<211> LENGTH: 20
<212> TYPE: DNA
<213> ORGANISM: Artificial Sequence
<220> FEATURE:
<223> OTHER INFORMATION: synthetic primer BG Cat FWD directed to
    beta-glucosidase (BG) nucleophile region

<400> SEQUENCE: 29
ggccatttgc tgatgctatt                                            20

<210> SEQ ID NO 30
<211> LENGTH: 21
<212> TYPE: DNA
<213> ORGANISM: Artificial Sequence
<220> FEATURE:
<223> OTHER INFORMATION: synthetic primer BG Cat REV directed to
    beta-glucosidase (BG) nucleophile region

<400> SEQUENCE: 30
caactctcca ttgtggaaca g                                          21

<210> SEQ ID NO 31
<211> LENGTH: 21
<212> TYPE: DNA
<213> ORGANISM: Artificial Sequence
<220> FEATURE:
<223> OTHER INFORMATION: synthetic primer BG Acid-Base FWD directed to
    beta-glucosidase (BG) enzyme substrate hydrolysis region

<400> SEQUENCE: 31
ctgttccaca atggagagtt g                                          21

<210> SEQ ID NO 32
<211> LENGTH: 23
<212> TYPE: DNA
<213> ORGANISM: Artificial Sequence
<220> FEATURE:
<223> OTHER INFORMATION: synthetic primer BG Orf REV directed to
    beta-glucosidase (BG) enzyme substrate hydrolysis region

<400> SEQUENCE: 32
ctaatgaaca gttggcaaag aag                                        23

<210> SEQ ID NO 33
<211> LENGTH: 55
<212> TYPE: DNA
<213> ORGANISM: Artificial Sequence
<220> FEATURE:
<223> OTHER INFORMATION: synthetic primer EDQ.JHV.054 used for
    integration into plasmid

<400> SEQUENCE: 33
agcgatagac ctttggtccc cggatcccca atgagattta ctttgattga agctg      55

<210> SEQ ID NO 34
<211> LENGTH: 53
<212> TYPE: DNA
<213> ORGANISM: Artificial Sequence
<220> FEATURE:
<223> OTHER INFORMATION: synthetic primer EDQ.JHV.095 used for -continued

```
       integration into plasmid

<400> SEQUENCE: 34
gacggtatcg ataagcttga tatcgaattc ctaatgaaca gttggcaaag aag            53

<210> SEQ ID NO 35
<211> LENGTH: 29
<212> TYPE: DNA
<213> ORGANISM: Artificial Sequence
<220> FEATURE:
<223> OTHER INFORMATION: synthetic primer Tau3up F1 used for integration
      into genome

<400> SEQUENCE: 35
gatcaagatc gctgcgttgt tgttgatgg                                       29

<210> SEQ ID NO 36
<211> LENGTH: 32
<212> TYPE: DNA
<213> ORGANISM: Artificial Sequence
<220> FEATURE:
<223> OTHER INFORMATION: synthetic primer Tau3down R1 used for
      integration into genome

<400> SEQUENCE: 36
gatcttgatc gagcccgtaa tacaacagtg ag                                   32
```